United States Patent
Sano

(10) Patent No.: US 11,495,335 B2
(45) Date of Patent: Nov. 8, 2022

(54) HEALTH CARE SYSTEM

(71) Applicant: NOMURA RESEARCH INSTITUTE, LTD., Tokyo (JP)

(72) Inventor: Noriko Sano, Tokyo (JP)

(73) Assignee: NOMURA RESEARCH INSTITUTE, LTD., Tokyo (JP)

( * ) Notice: Subject to any disclaimer, the term of this patent is extended or adjusted under 35 U.S.C. 154(b) by 713 days.

(21) Appl. No.: 15/821,112

(22) Filed: Nov. 22, 2017

(65) Prior Publication Data

US 2018/0096739 A1 Apr. 5, 2018

Related U.S. Application Data

(63) Continuation of application No. PCT/JP2016/064855, filed on May 19, 2016.

(30) Foreign Application Priority Data

May 26, 2015 (JP) .............................. JP2015-106353

(51) Int. Cl.
*G16H 10/60* (2018.01)
*G16H 40/63* (2018.01)
(Continued)

(52) U.S. Cl.
CPC ............... *G16H 10/60* (2018.01); *A61B 5/01* (2013.01); *A61B 10/0012* (2013.01);
(Continued)

(58) Field of Classification Search
CPC ........ G16H 10/60; G16H 40/67; G16H 40/20; G16H 40/63; G06F 16/9038;
(Continued)

(56) References Cited

U.S. PATENT DOCUMENTS

2004/0030586 A1* 2/2004 Cucchiara .............. G06Q 10/10
705/3
2007/0082329 A1* 4/2007 Williams ........... G01N 33/5044
705/2
(Continued)

FOREIGN PATENT DOCUMENTS

JP 3577972 B2 * 10/2004
JP 2008-262504 10/2008
(Continued)

OTHER PUBLICATIONS

English translation of Written Opinion of the International Searching Authority dated Jul. 19, 2016 in corresponding International Patent Application No. PCT/JP2016/064855.
(Continued)

*Primary Examiner* — Robert A Sorey
*Assistant Examiner* — Kristine K Rapillo
(74) *Attorney, Agent, or Firm* — Staas & Halsey LLP

(57) ABSTRACT

A health care system includes a server to provide a service to care for a health state of each user, and a terminal of each user. The server registers and manages user information containing at least attribute information of the user, health information, or action information as share information of a group of users in response to an operation from the terminal of the user, checks similarity between the users in the share information, determines a similar user of each of the users, and outputs share information of the similar user of the user to the terminal of the user on the basis of the check information. The health information contains time series data of one element of measurement items containing a body temperature of the user, menstruation, examination results, medication, or symptoms. The action information contains time series data of one of actions or arbitrary texts.

3 Claims, 33 Drawing Sheets

(51) Int. Cl.
| | |
|---|---|
| *G16H 40/20* | (2018.01) |
| *G16H 40/67* | (2018.01) |
| *G06F 16/31* | (2019.01) |
| *G06F 16/9535* | (2019.01) |
| *G06F 16/9038* | (2019.01) |
| *G16H 20/10* | (2018.01) |
| *G16H 70/60* | (2018.01) |
| *A61B 5/01* | (2006.01) |
| *A61B 10/00* | (2006.01) |
| *A61B 5/00* | (2006.01) |

(52) U.S. Cl.
CPC ........ *G06F 16/316* (2019.01); *G06F 16/9038* (2019.01); *G06F 16/9535* (2019.01); *G16H 20/10* (2018.01); *G16H 40/20* (2018.01); *G16H 40/63* (2018.01); *G16H 40/67* (2018.01); *G16H 70/60* (2018.01); *A61B 5/4343* (2013.01)

(58) Field of Classification Search
CPC ... G06F 16/9535; G06F 16/316; G06Q 50/22; A61B 10/0012; A61B 5/01; A61B 5/4343
See application file for complete search history.

(56) References Cited

U.S. PATENT DOCUMENTS

| | | | |
|---|---|---|---|
| 2009/0125333 A1 | 5/2009 | Heywood et al. | |
| 2009/0131758 A1 | 5/2009 | Heywood et al. | |
| 2009/0138281 A1* | 5/2009 | Hacker | G06Q 10/10 |
| | | | 705/3 |
| 2009/0144089 A1 | 6/2009 | Heywood et al. | |
| 2011/0246565 A1* | 10/2011 | Irwin | H04L 67/02 |
| | | | 709/203 |
| 2013/0066652 A1 | 3/2013 | Heywood et al. | |
| 2013/0231953 A1* | 9/2013 | Ebadollahi | G16H 50/70 |
| | | | 705/7.29 |
| 2013/0268547 A1 | 10/2013 | Boroczky et al. | |
| 2014/0365238 A1* | 12/2014 | Kono | G16H 10/60 |
| | | | 705/2 |
| 2015/0227714 A1* | 8/2015 | Hayakawa | G16H 10/60 |
| | | | 705/3 |
| 2015/0324530 A1* | 11/2015 | Heywood | G16H 15/00 |
| | | | 705/3 |
| 2016/0188807 A1 | 6/2016 | Heywood et al. | |
| 2016/0246790 A1* | 8/2016 | Cowdrey | G06F 16/24578 |
| 2017/0206327 A1 | 7/2017 | Heywood et al. | |

FOREIGN PATENT DOCUMENTS

| | | |
|---|---|---|
| JP | 2009-205456 | 9/2009 |
| JP | 2011-501844 | 1/2011 |
| JP | 2011-164670 | 8/2011 |
| JP | 2014-503894 | 2/2014 |
| WO | WO 2014/076777 A1 | 5/2014 |

OTHER PUBLICATIONS

Human Holdings Co., Ltd., VEAUTY, Mar. 15, 2015, Retrieved from <URL:https://web.archive.org/web/20150315022549/http://veauty.jp/>, on Jul. 5, 2016.

Yokyama Shigeki, "Medical Data Mining", General Healthcare company (SPP Publishing), Feb. 14, 2014, First edition, pp. 87-88**.

Japanese Office Action dated Aug. 27, 2019 in corresponding Japanese Patent Application No. 2015-106353.

International Search Report dated Jul. 19, 2016 in corresponding International Patent Application No. PCT/JP2016/064855.

* cited by examiner

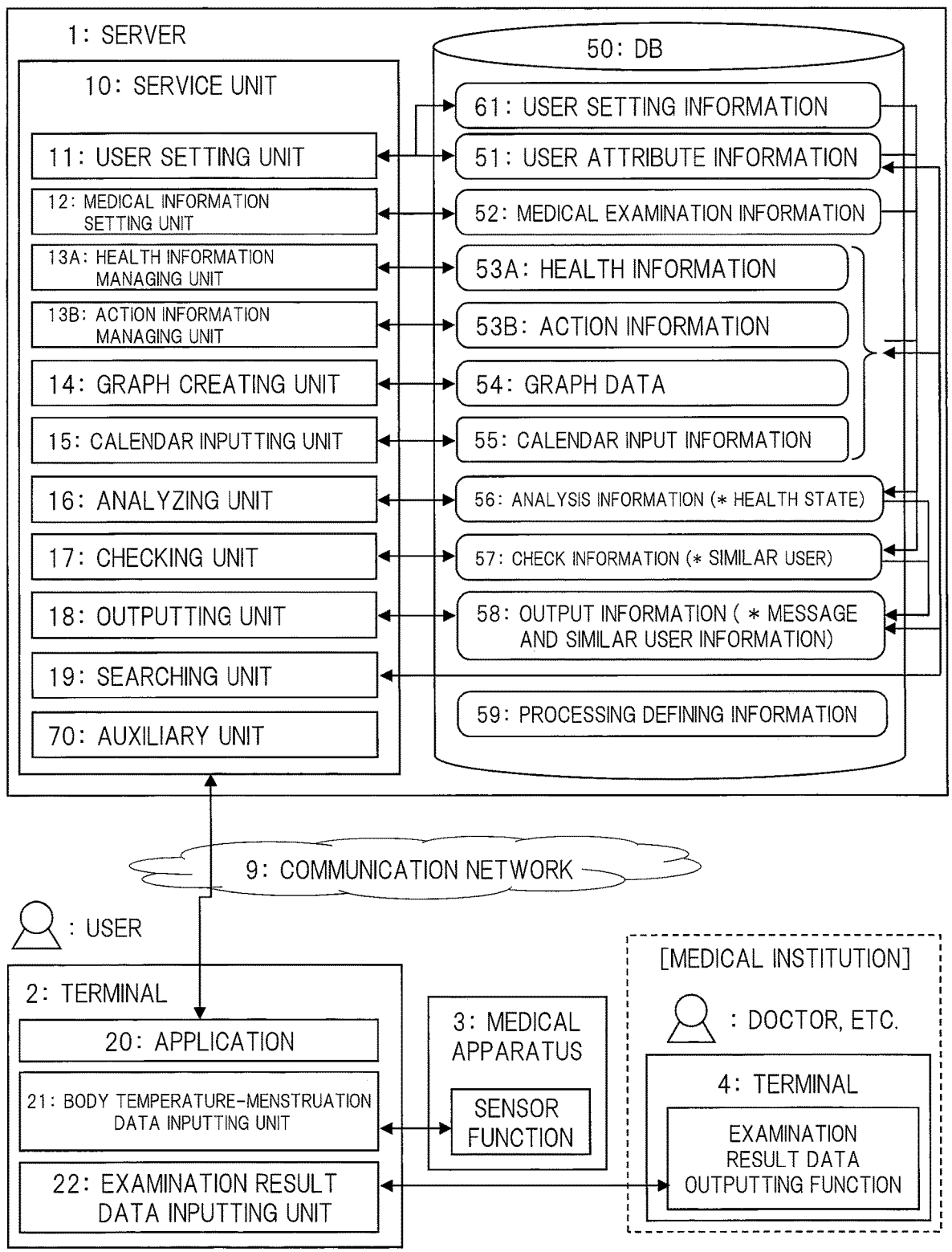

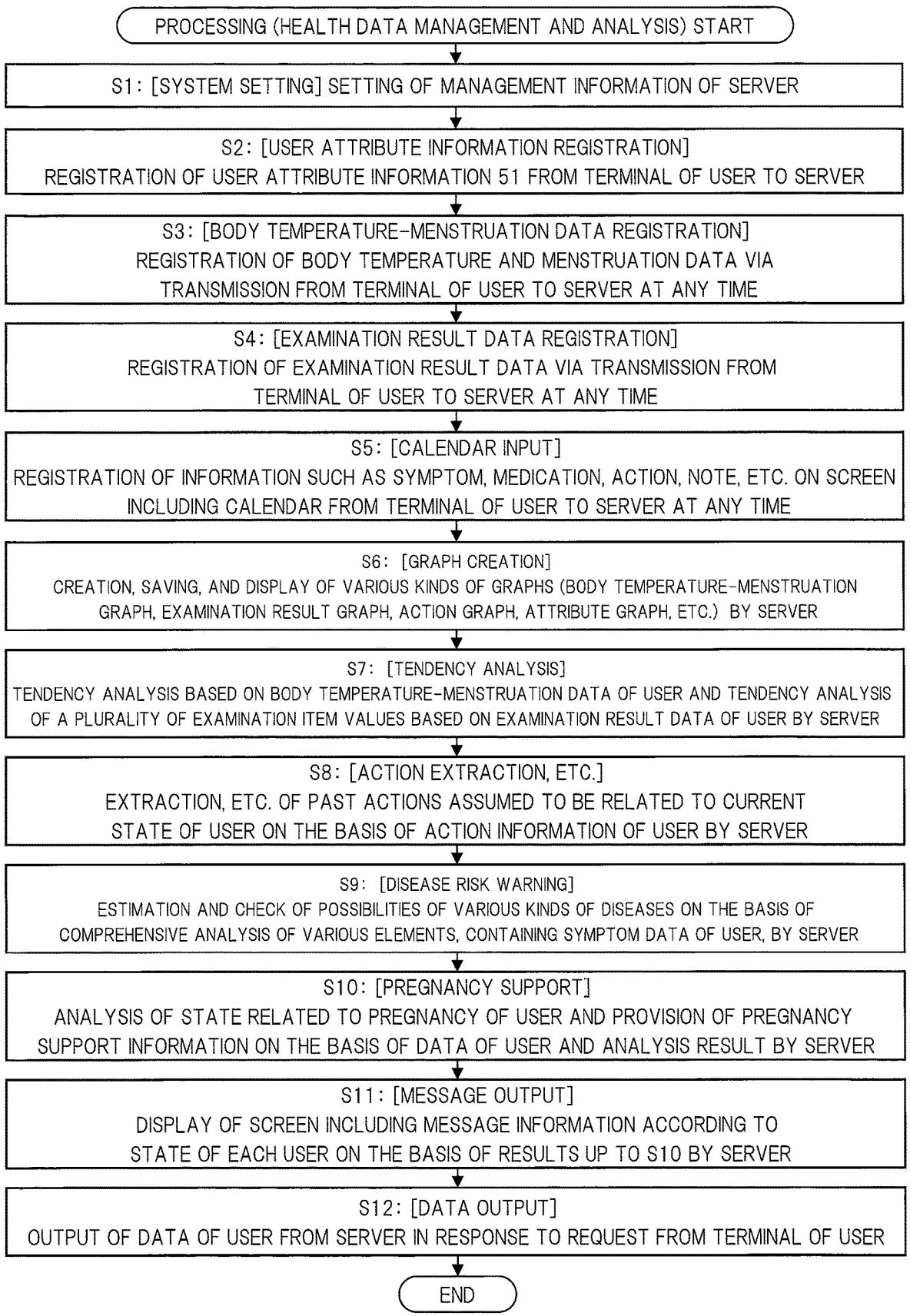

FIG. 5A

51: USER ATTRIBUTE INFORMATION

| ITEM (ATTRIBUTE) | DESCRIPTION | SPECIFIC EXAMPLE | SHARE (DISCLOSURE) |
|---|---|---|---|
| USER ID | USER IDENTIFICATION INFORMATION | 01234567 | — |
| PASSWORD | FOR USER AUTHENTICATION | ****** | — |
| TERMINAL ADDRESS | COMMUNICATION ADDRESS OF USER TERMINAL | ... | — |
| USER NAME | ANONYMOUS, NICKNAME | USER A | ○ |
| SEX | FEMALE/MALE | FEMALE/MALE | ○ |
| AGE | AGE OR AGE GROUP | 35 YEARS OLD | ○ |
| MEDICAL INSTITUTION | HOSPITAL AND EXAMINATION INSTITUTION THAT USER CURRENTLY VISITS. HISTORY OF CHANGING HOSPITALS, ETC. IS INCLUDED. | PRESENT: HOSPITAL A JANUARY TO DECEMBER, 2012: HOSPITAL B JANUARY, 2013 TO PRESENT: HOSPITAL A | ○ |
| TREATMENT PERIOD | STARTING DATE TO ENDING DATE OF TREATMENT, NUMBER OF YEARS, ETC. | 2011 TO 2013 (TWO YEARS) | ○ |
| TREATMENT | TREATMENT STATUS BY MEDICAL INSTITUTION. TREATMENT HISTORY IS INCLUDED. | PRESENT: TREATMENT X (E.G., IN-VITRO FERTILIZATION) 2011: TIMING METHOD MARCH, 2012: ARTIFICIAL INSEMINATION JUNE, 2013: IN-VITRO FERTILIZATION | ○ |
| DISEASE | MAIN DISEASE CONCERNED WITH TREATMENT ITEM. HISTORY IS INCLUDED. | PRESENT: DISEASE X (E.G., INFERTILITY) | ○ |
| ANAMNESIS | SECONDARY DISEASE OTHER THAN MAIN DISEASE, ANAMNESIS, SURGICAL HISTORY, ETC., CONCERNED WITH TREATMENT ITEM | 2009: DISEASE Y 2009: TREATMENT Y | ○ |
| PREGNANCY | STATUS OF PREGNANCY AND CHILDBIRTH (SUCCESS/FAILURE, NUMBER OF TIMES, PERIOD OF TIME, ETC.) | PREGNANCY: 0 TIMES | ○ |
| PARTNER | INFORMATION ON PARTNER SUCH AS HUSBAND OR THE LIKE (CONTAINING STATUS OF TREATMENT AND DISEASE) | HUSBAND: 38 YEARS OLD DISEASE Z | × |
| MEMBERSHIP TYPE | INFORMATION INDICATING USE RANGE OF SERVICE | ..... | — |
| ..... | ..... | ..... | ... |

501: SHARE ATTRIBUTE SETTING ITEM
* ○(1): SHARE   ×(0): NOT SHARE

FIG. 5B

53A: HEALTH INFORMATION

| CLASSIFICATION | ITEM | DESCRIPTION | SPECIFIC EXAMPLE |
|---|---|---|---|
| (a) BODY TEMPERATURE | BASAL BODY TEMPERATURE | TEMPERATURE MEASURING DATE, BODY TEMPERATURE, ETC. | 3/3/2014, 36.5°C |
| (b) MENSTRUATION | MENSTRUATION | START DATE OF THIS TIME, END DATE OF THIS TIME, START DATE OF PREVIOUS TIME, END DATE OF PREVIOUS TIME, MENSTRUAL CYCLE, ESTIMATED OVULATION DATE | 4/1/2014 TO 4/5 3/3/2014 TO 3/7 28 DAYS, 4/15/2014 |
| (c) EXAMINATION RESULT | ...... | ...... | ...... |
| (d) SYMPTOM | SYMPTOM | SYMPTOM REGARDING PHYSICAL CONDITION | HEADACHE, FEELING OF FATIGUE, STRESS |
| (e) MEDICATION | MEDICATION | NAME OF MEDICINE, START DATE OF TAKING MEDICINE, END DATE OF TAKING MEDICINE, SIDE EFFECTS, STOP OR NOT OF TAKING MEDICINE, SYMPTOM OF SIDE EFFECTS | CLOMID, 3/3/2014 TO 3/7, PRESENCE OF SIDE EFFECTS, PRESENCE OF STOP OF TAKING MEDICINE, STOMACHACHE |
| (f) OTHERS | SELF MEASUREMENT ITEM (EXAMPLE) BLOOD PRESSURE, PULSE, BREATHING, HEART RATE | MEASURING DATE, MEASURED VALUE | ...... |
| ...... | ...... | ...... | ...... |

FIG. 5C

53A: HEALTH INFORMATION

| CLASSIFICATION | ITEM | DESCRIPTION | SPECIFIC EXAMPLE |
|---|---|---|---|
| (c) EXAMINATION RESULT | PREGNANCY SUPPORT (MALE COMMON EXAMINATION ITEMS) | SPERM COLLECTION DATE, SEMEN VOLUME, TOTAL SPERM NUMBER, SPERM DENSITY, FORWARD MOTILITY, HIGH-SPEED STRAIGHT MOTILITY, SURVIVAL RATE, NORMAL MORPHOLOGY RATE | 3/3/2014, 2 ml, 40 × 10^6 /ml, 20 × 10^6 /ml, 50%, 25%, 50%, 50% |
| | PREGNANCY SUPPORT (FEMALE COMMON EXAMINATION ITEMS) | EXAMINATION DATE, LH, FSH, E2, P4, AMH, SIZE OF FOLLICLE, ENDOMETRIAL THICKNESS | 3/3/2014, 2.2 mIU/mL, 6 mIU/mL, 80 pg/mL, 6.5 ng/m, 11 pM, 20 mm, 8 mm |
| | PREGNANCY SUPPORT (TIMING METHODS) | METRORRHAGIA, OVULATION INDUCTION, WIDTH OF WHITE VAGINAL DISCHARGE | ABSENCE OF METRORRHAGIA, PRESENCE OF OVULATION INDUCTION, WIDTH OF WHITE VAGINAL DISCHARGE OF 7cm |
| | PREGNANCY SUPPORT (ARTIFICIAL INSEMINATION) | LH IN URINE, PRESENCE OR ABSENCE OF ARTIFICIAL INSEMINATION | POSITIVE, PRESENCE OF ARTIFICIAL INSEMINATION |
| | PREGNANCY SUPPORT (IN-VITRO FERTILIZATION: EGG COLLECTION) | ANESTHESIA METHOD, COLLECTION DATE OF EGGS, EGG COLLECTION NUMBER, FROZEN EMBRYO No-GRADE | INTRAVENOUS ANESTHESIA, 3/21/2014, 5, {No1-A, No2-A, No3-B, No4-B} |
| | PREGNANCY SUPPORT (IN-VITRO FERTILIZATION: TRANSPLANT) | TRANSPLANT DATE, TRANSPLANTED EMBRYO No-GRADE-SIZE, PRESENCE OR ABSENCE OF ASSISTED HATCHING, TRANSPLANT METHOD | 3/22/2014, No1-A-48mm, PRESENCE, MICROINSEMINATION |
| | PREGNANCY SUPPORT (IN-VITRO FERTILIZATION: PREGNANCY) | DETERMINATION DATE OF PREGNANCY, POSITIVE DETERMINATION OF PREGNANCY, CONFIRMATION DATE OF FETAL SAC, CONFIRMATION OR NOT OF FETAL SAC, CONFIRMATION DATE OF HEART RATE | 3/31/2014, POSITIVE, BLANK, BLANK, BLANK |
| | OTHER MEDICAL INSTITUTION EXAMINATION ITEMS | ...... | ...... |
| | SELF MEASURING ITEMS (SELF EXAMINATION ITEMS) | BLOOD PRESSURE (HIGH), BLOOD PRESSURE (LOW), PULSE RATE, BREATHING RATE PER MINUTE, OVULATION TEST RESULT, PREGNANCY TEST RESULT, AMOUNT OF SECRETION | 110, 60, 70, 20, ...... |

FIG. 5D

53B: ACTION INFORMATION

| CLASSIFICATION | ITEM | DESCRIPTION | SPECIFIC EXAMPLE |
|---|---|---|---|
| ACTION | EXERCISE THERAPY | IMPLEMENTATION PERIOD OF EXERCISE THERAPY, EXERCISE THERAPY | 1/10/2014 TO 4/30, SWIMMING |
| ACTION | DIET THERAPY | IMPLEMENTATION PERIOD OF DIET THERAPY, DIET THERAPY | 1/10/2014 TO 4/30, FOLIC ACID |
| ACTION | ...... | ...... | ...... |
| TIMING | TIMING | SEXUAL INTERCOURSE DATE, PRESENCE OR ABSENCE OF SEXUAL INTERCOURSE | 3/3/2014, PRESENCE |
| NOTE | NOTE | ARBITRARY AND FREE TEXT AND CHARACTER STRING CONTAINING COMMENT, MEMO, FEELING AND THE LIKE | FEEL STRONG STRESS |
| AUTOMATIC MEASUREMENT ITEM | EXAMPLE: EXERCISE TIME AND AMOUNT, SLEEP TIME AND AMOUNT, USED CALORIES, ETC. | AUTOMATIC MEASUREMENT RELATED TO ACTION AND MEASUREMENT ITEM THAT CAN BE REGISTERED AUTOMATICALLY | ...... |
| ...... | ...... | ...... | ...... |

FIG. 6

| 61: USER SETTING INFORMATION (∗ SETTING BY PRESENT SYSTEM) ||||
|---|---|---|---|
| SERVICE A SETTING INFORMATION (↔ USER GROUP A) ||||
| (61a) SHARE ITEM || ATTRIBUTE | ALL |
| || ELEMENT | ALL |
| || ANALYSIS | ALL |
| (61b) DETERMINING ITEM || ATTRIBUTE | {SEX, AGE, DISEASE, TREATMENT} |
| || ELEMENT | — (∗ NOTHING) |
| || ANALYSIS | — |
| (61c) PRIORITY OUTPUT ITEM || ATTRIBUTE | — |
| || ELEMENT | — |
| || ANALYSIS | — |
| SERVICE B SETTING INFORMATION (↔ USER GROUP B) ||||
| (61a) SHARE ITEM || ATTRIBUTE | ALL |
| || ELEMENT | ALL |
| || ANALYSIS | ALL |
| (61b) DETERMINING ITEM || ATTRIBUTE | — |
| || ELEMENT | {BODY TEMPERATURE, MENSTRUATION, EXAMINATION RESULT} |
| || ANALYSIS | — |
| SERVICE C SETTING INFORMATION (↔ USER GROUP C) ||||
| (61a) SHARE ITEM || ATTRIBUTE | ALL |
| || ELEMENT | ALL |
| || ANALYSIS | ALL |
| (61b) DETERMINING ITEM || ATTRIBUTE | — |
| || ELEMENT | — |
| || ANALYSIS | TENDENCY ANALYSIS |

FIG. 7

| 61: USER SETTING INFORMATION (* SETTING BY INDIVIDUAL USER) |||
|---|---|---|
| USER A SETTING INFORMATION |||
| (61a) SHARE ITEM | ALL ||
| (61b) DETERMINING ITEM | ATTRIBUTE | {SEX, AGE, DISEASE, TREATMENT} + {MEDICAL INSTITUTION, EXAMINATION INSTITUTION} |
| | ELEMENT | — |
| | ANALYSIS | — |
| (61c) PRIORITY OUTPUT ITEM | ATTRIBUTE | — |
| | ELEMENT | {EXAMINATION RESULT, MENSTRUATION} |
| | ANALYSIS | {TENDENCY ANALYSIS, DISEASE RISK WARNING} |
| USER B SETTING INFORMATION |||
| (61a) SHARE ITEM | ALL ||
| (61b) DETERMINING ITEM | ATTRIBUTE | — |
| | ELEMENT | {BODY TEMPERATURE, MENSTRUATION, EXAMINATION RESULT} + {ACTION} |
| | ANALYSIS | — |
| (61c) PRIORITY OUTPUT ITEM | ATTRIBUTE | {PREGNANCY, PARTNER} |
| | ELEMENT | — |
| | ANALYSIS | {ACTION EXTRACTION, PREGNANCY SUPPORT} |
| USER C SETTING INFORMATION |||
| (61a) SHARE ITEM | ATTRIBUTE | ALL |
| | ELEMENT | {BODY TEMPERATURE, MENSTRUATION, EXAMINATION RESULT} |
| | ANALYSIS | {TENDENCY ANALYSIS, DISEASE RISK WARNING} |
| (61b) DETERMINING ITEM | ATTRIBUTE | {SEX, AGE} |
| | ELEMENT | {BODY TEMPERATURE, MENSTRUATION, EXAMINATION RESULT} |
| | ANALYSIS | {TENDENCY ANALYSIS, DISEASE RISK WARNING} |
| (61c) PRIORITY OUTPUT ITEM | ATTRIBUTE | {DISEASE, TREATMENT} |
| | ELEMENT | {EXAMINATION RESULT} |
| | ANALYSIS | {TENDENCY ANALYSIS, DISEASE RISK WARNING} |

FIG. 8

| 61: USER SETTING INFORMATION ( * SETTING BY INDIVIDUAL USER) | | | |
|---|---|---|---|
| USER D SETTING INFORMATION | | | |
| (61a) SHARE ITEM | | ATTRIBUTE | ALL EXCEPT FOR {PREGNANCY, PARTNER} |
| | | ELEMENT | ALL EXCEPT FOR {NOTE} |
| | | ANALYSIS | ALL EXCEPT FOR {PREGNANCY SUPPORT} |
| (61b) DETERMINING ITEM | | ATTRIBUTE | {SEX, AGE, ANAMNESIS} |
| | | ELEMENT | {ACTION} |
| | | ANALYSIS | {TENDENCY ANALYSIS, ACTION EXTRACTION} |
| (61c) PRIORITY OUTPUT ITEM | | ATTRIBUTE | — |
| | | ELEMENT | — |
| | | ANALYSIS | {ACTION EXTRACTION} |
| USER E SETTING INFORMATION | | | |
| (61a) SHARE ITEM | | ALL | |
| (61b) DETERMINING ITEM | | ATTRIBUTE | {SEX, AGE, PREGNANCY, PARTNER} |
| | | ELEMENT | {EXAMINATION RESULT} |
| | | ANALYSIS | {PREGNANCY SUPPORT} |
| (61c) PRIORITY OUTPUT ITEM | | ATTRIBUTE | {DISEASE, TREATMENT, MEDICAL INSTITUTION} |
| | | ELEMENT | {SYMPTOM, NOTE} |
| | | ANALYSIS | {PREGNANCY SUPPORT} |
| USER F SETTING INFORMATION | | | |
| (61a) SHARE ITEM | | ALL | |
| (61b) DETERMINING ITEM | | ATTRIBUTE | {SEX, AGE, DISEASE, TREATMENT} + {PREGNANCY = SUCCESS} |
| | | ELEMENT | — |
| | | ANALYSIS | — |

FIG. 9

52: MEDICAL EXAMINATION INFORMATION

| ITEM | DESCRIPTION | SPECIFIC EXAMPLE |
|---|---|---|
| MEDICAL INSTITUTION | IDENTIFICATION INFORMATION OF MEDICAL INSTITUTION | MEDICAL INSTITUTION A (HOSPITAL A) |
| TREATMENT | IDENTIFICATION INFORMATION OF MEDICAL TREATMENT | TREATMENT A |
| TREATMENT METHOD | MEDICAL TREATMENT METHOD AND TREATMENT TYPE | TREATMENT METHOD A |
| ACHIEVEMENT | NUMBER OF TREATMENT CASES, NUMBER OF SURGERY CASES, ETC. | ANNUAL NUMBER OF CASES FOR TIMING METHOD, ANNUAL NUMBER OF CASES FOR ARTIFICIAL INSEMINATION, ANNUAL NUMBER OF CASES FOR IN-VITRO FERTILIZATION, ANNUAL NUMBER OF CASES FOR MICROINSEMINATION, PARAMETER, NUMBER OF PREGNANCY, PREGNANCY RATE |
| EXAMINATION INSTITUTION | IDENTIFICATION INFORMATION OF EXAMINATION INSTITUTION (MAY BE CONDUCTED AT MEDICAL INSTITUTION) | EXAMINATION COMPANY A MEDICAL INSTITUTION A |
| EXAMINATION | IDENTIFICATION INFORMATION OF MEDICAL EXAMINATION | EXAMINATION A |
| EXAMINATION TYPE | TYPE SUCH AS BLOOD TEST, URINALYSIS, ULTRASOUND EXAMINATION, PALPATION, ETC. | BLOOD TEST |
| EXAMINATION ITEM | SUBJECT ITEM OF EXAMINATION AND MEASUREMENT | LH (LUTEINIZING HORMONE) |
| EXAMINATION METHOD | MEDICAL EXAMINATION METHOD | EXAMINATION METHOD A = EIA METHOD EXAMINATION METHOD B = CLIA METHOD |
| REFERENCE INFORMATION | VALUE AND RANGE THAT ARE CRITERIA FOR DETERMINATION | VALUES A1, A2 RANGE A = A1 TO A2 |
| ... | ... | ... |

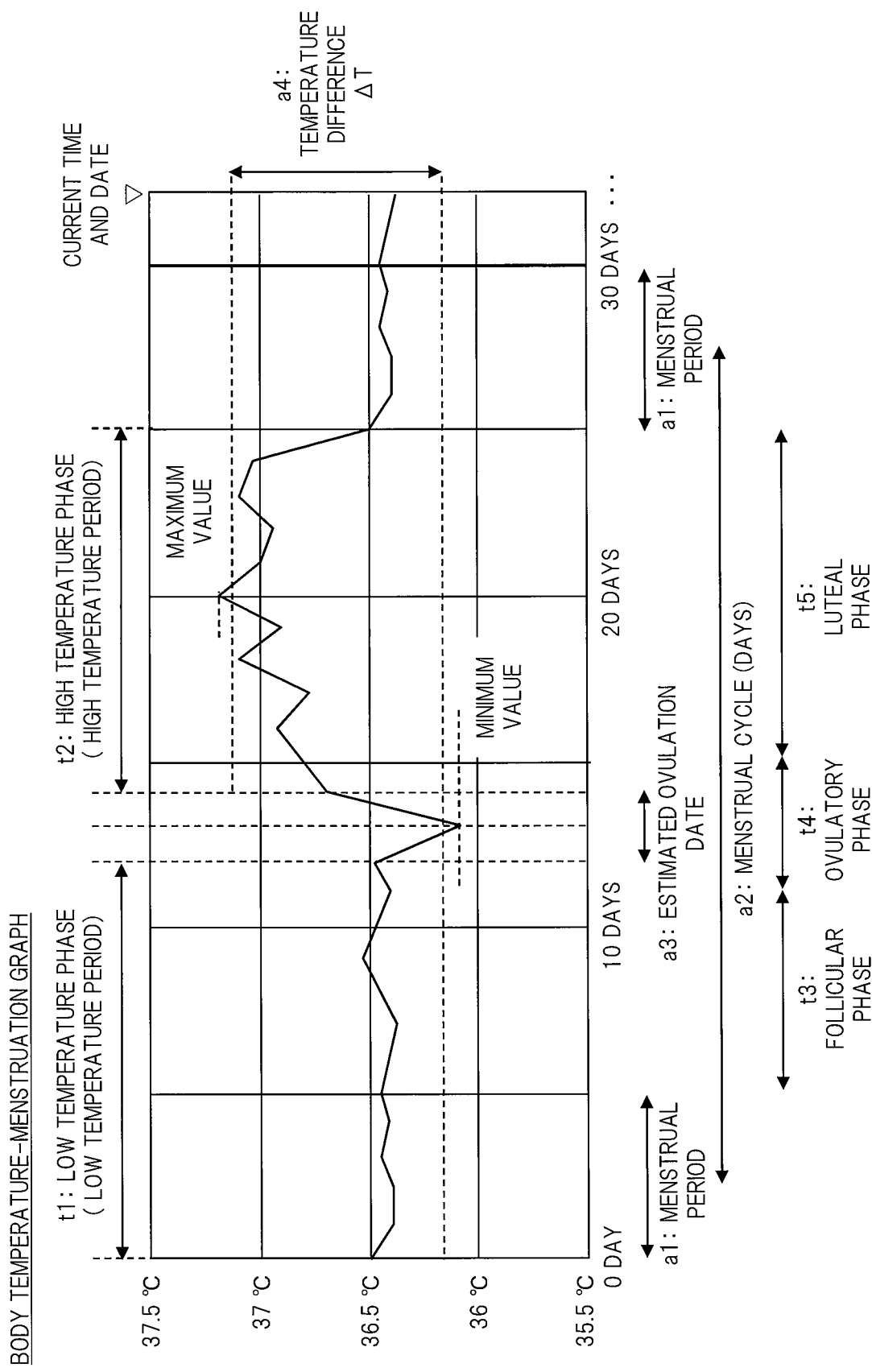

FIG. 11

EXAMINATION RESULT DATA

| USER | MEDICAL INSTITUTION | EXAMINATION INSTITUTION | EXAMINATION METHOD | EXAMINATION DATE | TYPE | ITEM | UNIT | VALUE |
|---|---|---|---|---|---|---|---|---|
| USER A | HOSPITAL A | EXAMINATION COMPANY A | EXAMINATION METHOD A | 07/01/2013 | BLOOD | LH | mIU/mL | n1 |
| | | | | | BLOOD | FSH | mIU/mL | n2 |
| | | | | | BLOOD | E2 | pg/mL | ... |
| | | | | | BLOOD | P4 | ·mol/L ·ng/mL | ... |
| | | | | | BLOOD | AMH | ·pM ·ng/mL | ... |
| | | | | | ... | ... | ... | ... |
| USER B | HOSPITAL B | EXAMINATION COMPANY B | EXAMINATION METHOD B | 07/02/2013 | BLOOD | LH | ~ | ~ |
| | | | | | BLOOD | FSH | ~ | ~ |
| | | | | | BLOOD | ... | ... | ... |
| ... | ... | ... | ... | | ... | ... | ... | ... |

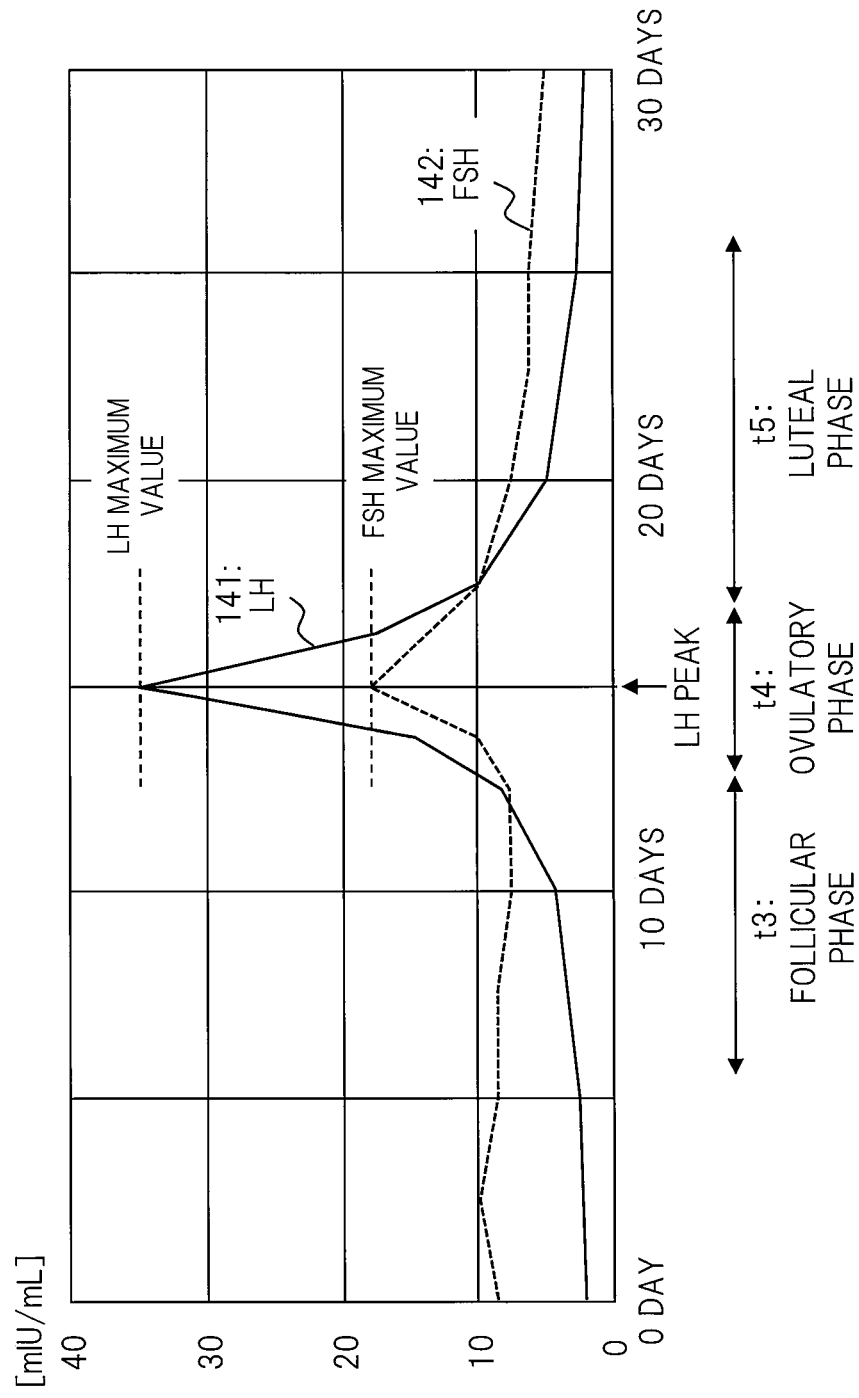

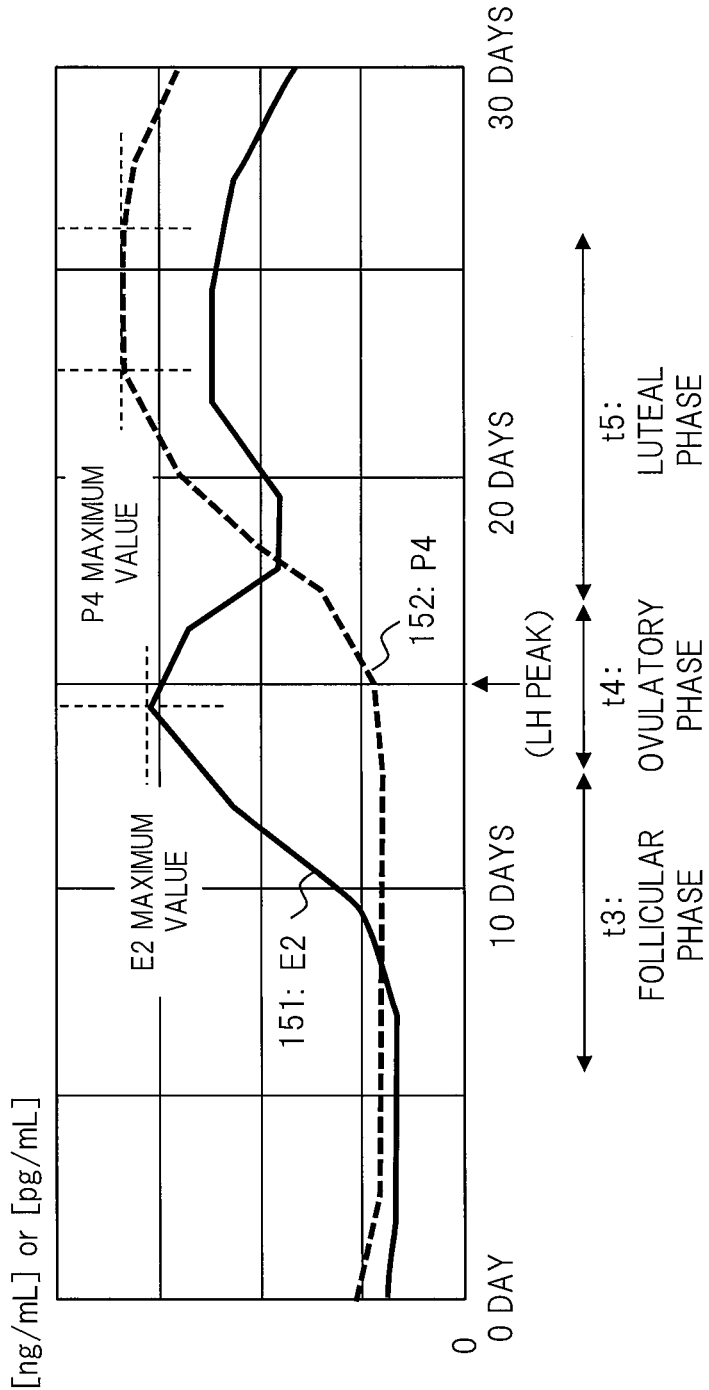

FIG. 14

<u>55: CALENDAR INPUT INFORMATION</u>

| DATE | TYPE | USER INPUT INFORMATION (* TEXT/CHOICE) |
|---|---|---|
| 11/01/2013 | MENSTRUATION | MENSTRUATION PERIOD (HAVING MENSTRUATION) |
| 11/02/2013 | NOTE | "FEEL GOOD", FACE MARK A |
| 11/03/2013 | NOTE | "FEEL GOOD", FACE MARK B |
| 11/04/2013 | SYMPTOM | HAVING STOMACHACHE, SEVERE |
| 11/05/2013 | SYMPTOM | HAVING DEPRESSION, MILD |
| 11/06/2013 | ACTION (EXERCISE THERAPY) | EXERCISE A |
| 11/07/2013 | ACTION (DIET THERAPY) | DIET A |
| 11/08/2013 | ... | ... |
| 11/09/2013 | EXAMINATION RESULT | EXAMINATION ITEM, EXAMINATION VALUE, EXAMINATION COMPANY A, ETC. |
| 11/10/2013 | MEDICATION | MEDICINE A, PERIOD, AMOUNT |
| 11/11/2013 | TREATMENT (HOSPITAL VISIT) | HOSPITAL A, TREATMENT A |
| 11/11/2013 | NOTE | "I got treatment A in hospital A. Dealing was kind. Waiting time was long." |
| ... | ... | ... |

FIG. 15

57: CHECK INFORMATION (∗ USER ATTRIBUTE COMPARISON)

(a) LIST OF SIMILAR USERS FOR EACH USER

| LIST OF SIMILAR USERS REGARDING USER X | | | | | |
|---|---|---|---|---|---|
| # SIMILARITY ORDER | DEGREE OF SIMILARITY (R, L) | USER | SIMILAR ATTRIBUTE | DISSIMILAR ATTRIBUTE | ... |
| 1 | R1, L1 | USER A | A, B, C, D | E, F, G, H | ... |
| 2 | R2, L2 | USER B | A, B, C | D, E, F, G, H | ... |
| 3 | R3, L3 | USER C | A, B | C, D, E, F, G, H | ... |
| ... | ... | ... | ... | ... | ... |

R: degree of similarity (∗ value) (R1 > R2 > R3)
L: degree of similarity (∗ level) (L1 > L2 > L3)

(b) INFORMATION OF COMPARISON OF ATTRIBUTES BETWEEN USERS

| COMPARISON OF ATTRIBUTES BETWEEN USER X AND USER A | | | | |
|---|---|---|---|---|
| ATTRIBUTE | USER X ATTRIBUTE VALUE | USER A ATTRIBUTE VALUE | ATTRIBUTE DEGREE OF SIMILARITY (r) | ... |
| ATTRIBUTE A | a1 | a2 | r1 | ... |
| ATTRIBUTE B | b1 | b2 | r2 | ... |
| ATTRIBUTE C | c1 | c2 | r3 | ... |
| ... | ... | ... | ... | ... |

| COMPREHENSIVE DEGREE OF SIMILARITY REGARDING USER ATTRIBUTE: R1, L1 |
|---|

(c) INFORMATION ON ATTRIBUTE UNITS

| LIST OF SIMILAR USERS REGARDING ATTRIBUTES A | | | | |
|---|---|---|---|---|
| # PERSON NUMBER ORDER | ATTRIBUTE VALUE | USER | NUMBER OF PERSONS | ... |
| 1 | a1 | USER A, D, G, J, M, P, ... | N1 | ... |
| 2 | a2 | USER B, E, H, K, N, ... | N2 | ... |
| 3 | a3 | USER C, F, I, L, ... | N3 | ... |
| ... | ... | ... | | ... |

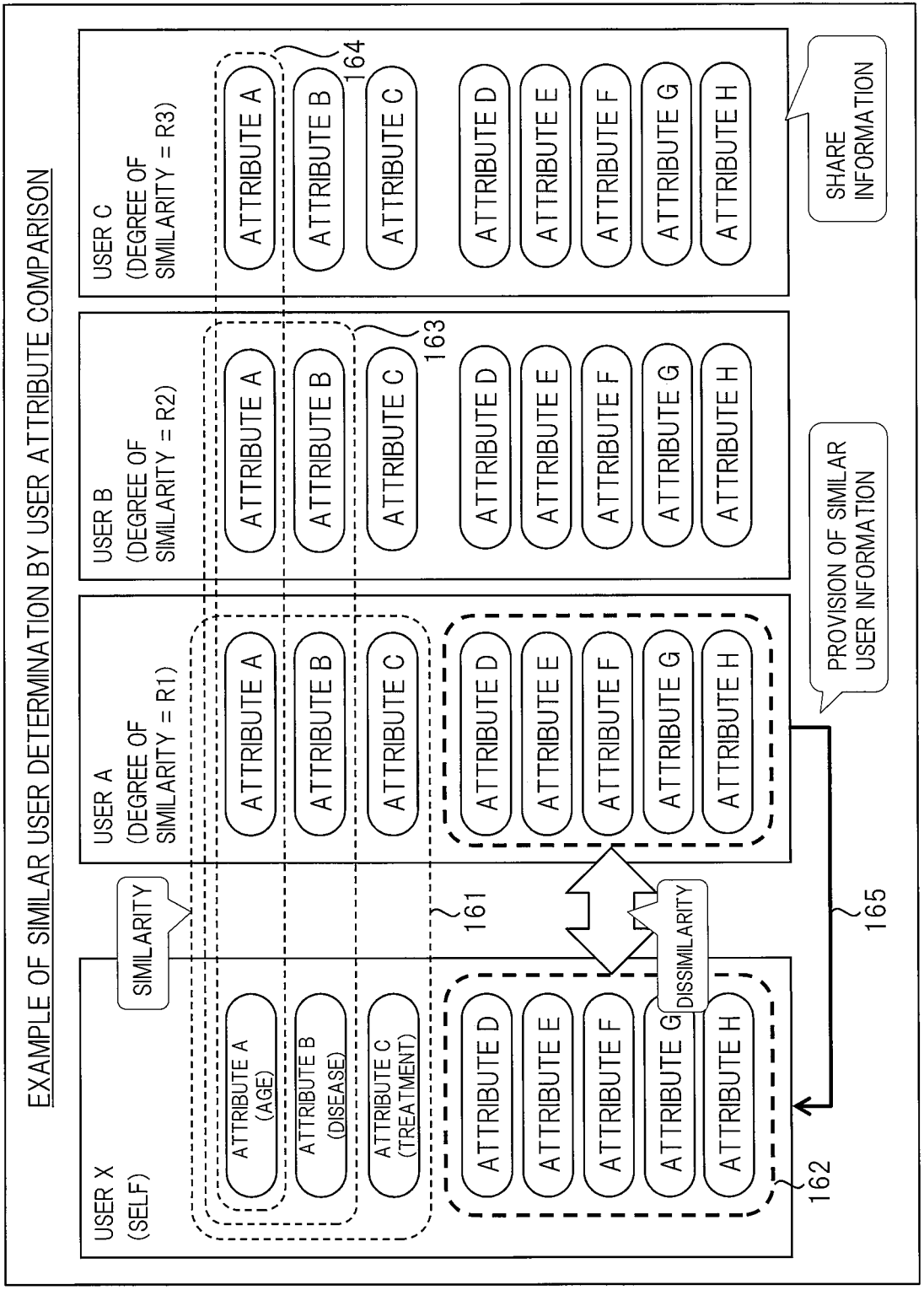

FIG. 17
SIMILAR USER DETERMINATION BY GRAPH COMPARISON EXAMPLE
(a) EXAMINATION RESULT GRAPH OF USER X (EXAMINATION ITEM: P4)
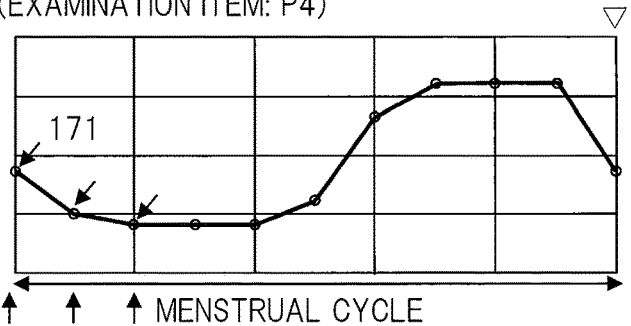
EXAMINATION DATE (REGISTRATION DATE)
(b) EXAMINATION RESULT GRAPH OF USER A (EXAMINATION ITEM: P4)
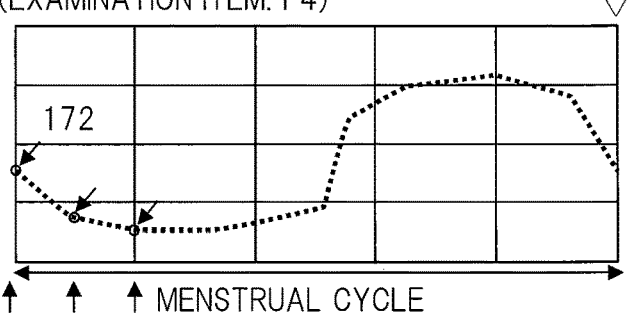
(c) COMPARISON OF GRAPHS BETWEEN USER X AND USER A
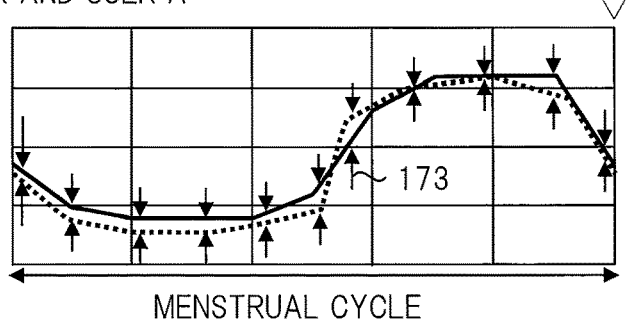
MENSTRUAL CYCLE
(d) REFERENCE GRAPH (EXAMINATION ITEM: P4)
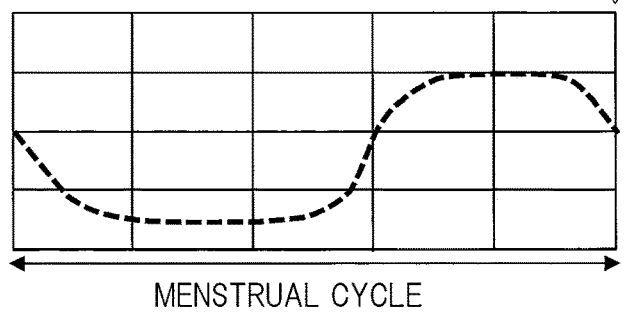
MENSTRUAL CYCLE

FIG. 18

SIMILAR USER DETERMINATION BY ACTION COMPARISON AND SYMPTOM COMPARISON EXAMPLE (a) EXAMINATION RESULT GRAPH OF USER X

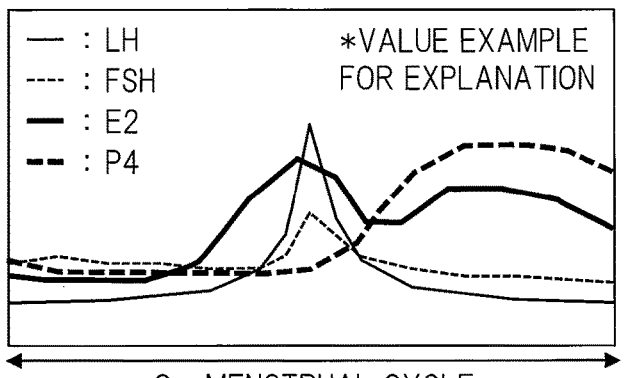

— : LH
---- : FSH
▬ : E2
▬ ▬ : P4

*VALUE EXAMPLE FOR EXPLANATION

Ga: MENSTRUAL CYCLE

REGISTRATION DATA OF USER X
- ACTION: {EXERCISE a, EXERCISE b, DIET a, DIET b, ⋯}
- SYMPTOM: {SYMPTOM a, SYMPTOM b, SYMPTOM c, SYMPTOM d, ⋯}

COMPARISON (b) EXAMINATION RESULT GRAPH OF USER A

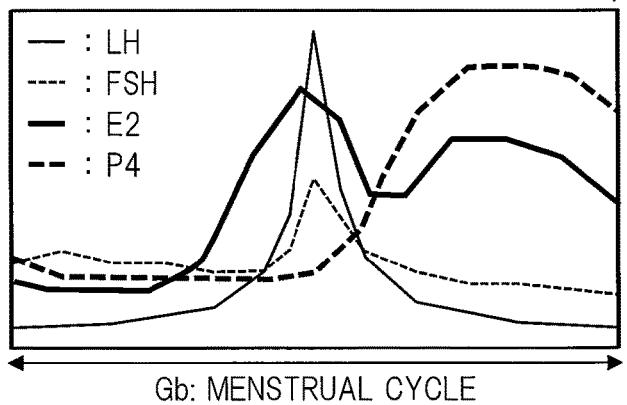

— : LH
---- : FSH
▬ : E2
▬ ▬ : P4

Gb: MENSTRUAL CYCLE

REGISTRATION DATA OF USER A
- ACTION: {EXERCISE a, EXERCISE c, DIET a, DIET c, ⋯}
- SYMPTOM: {SYMPTOM a, SYMPTOM b, SYMPTOM e, SYMPTOM f, ⋯}

FIG. 19

58: OUTPUT INFORMATION

(a) 58a: MESSAGE INFORMATION

| DATE | OUTPUT ID | USER (DESTINATION) | MESSAGE |
|---|---|---|---|
| 11/1/2013 | 001 | USER A | NOTICE MESSAGE (TENDENCY ANALYSIS MESSAGE) "Temperature difference has become 0.3 degree or more." |
| 11/2/2013 | 002 | USER B | NOTICE MESSAGE (TENDENCY ANALYSIS MESSAGE) "LH value has been improved in this examination result compared with last examination result." |
| 11/3/2013 | 003 | USER C | NOTICE MESSAGE (DISEASE RISK WARNING/CONSULTATION RECOMMENDATION MESSAGE) "There is a possibility of disease A. Consultation is recommended." |
| 11/4/2013 | 004 | USER D | NOTICE MESSAGE (DATA ANALYSIS MESSAGE) "LH value has been improved compared with previous menstrual cycle. Past action likely to be relevant to this improvement is action A." |
| 11/5/2013 | 005 | USER E | NOTICE MESSAGE (DATA ANALYSIS MESSAGE) "Exercise A had been done for xx days last month. Diet A has been done for yy days this month." |
| 11/6/2013 | 006 | USER F | NOTICE MESSAGE (DATA ANALYSIS MESSAGE) "Symptom A had appeared for xx days last month. Symptom B has appeared for yy days this month." |
| 11/7/2013 | 007 | USER G | NOTICE MESSAGE (DATA ANALYSIS MESSAGE) "Ease of pregnancy is xx. Yy is recommended to partner." |
| ... | ... | ... | ... |

(b) 58b: SIMILAR USER INFORMATION

| DATE | OUTPUT ID | USER (DESTINATION) | SIMILAR USER | PROVIDED INFORMATION |
|---|---|---|---|---|
| 12/01/2013 | 1001 | USER X | USER A | ALL |
| 12/02/2013 | 1002 | USER Y | USER D | USER ATTRIBUTE |
| 12/03/2013 | 1003 | USER Z | USER G | HEALTH INFORMATION |
| ... | ... | ... | ... | ... |

FIG. 20

```
┌─────────────────────────────────────────────────────────────────────┐
│ HEALTH CARE SERVICE                                                 │
```

◆ MY MEDICAL RECORD

101

| | |
|---|---|
| USER NAME: USER X<br>USER ID: 01234567<br>AGE: 35<br>START OF TREATMENT: 2011<br>NUMBER OF YEARS FOR TREATMENT: TWO YEARS<br>CURRENT TREATMENT: IN-VITRO FERTILIZATION<br>CURRENT MEDICAL CONDITION: INFERTILITY<br>ANAMNESIS AND SURGICAL HISTORY: NONE<br>CURRENT MEDICAL INSTITUTION: HOSPITAL A<br>...... | [TREATMENT HISTORY]<br>· AGE 33 (2011): TIMING METHOD<br>· AGE 34 (2012): ARTIFICIAL INSEMINATION ONCE<br>· AGE 35 (2013): IN-VITRO FERTILIZATION TWICE<br>......<br><br>[ACTION]<br>EXERCISE: EXERCISE A<br>DIET: DIET A<br>...... |

102 BODY TEMPERATURE-MENSTRUATION GRAPH  [REGISTRATION OF BODY TEMPERATURE]

(ANALYSIS RESULT) MENSTRUAL CYCLE: XX DAYS······  [REGISTRATION OF MENSTRUATION]

*[graph showing body temperature over DAY]*

103 EXAMINATION RESULT GRAPH (BLOOD TEST: LH)  [LH ▽]

(ANALYSIS RESULT) LH PEAK: YY DAY······  [REGISTRATION OF EXAMINATION RESULT]

*[graph showing LH peak over DAY]*

104 CALENDAR

| DATE | NOVEMBER 2013 | | | | | | | | | DECEMBER 2013 | | | | | | | |
|---|---|---|---|---|---|---|---|---|---|---|---|---|---|---|---|---|---|
| | 1 | 2 | 3 | 4 | 5 | 6 | 7 | ··· | 30 | 1 | 2 | 3 | 4 | 5 | 6 | 7 | ·· |
| MENSTRUATION | | | | | | | | | | | | | | | | | |
| ...... | | | | | | | | | | | | | | | | | |

105 OUTPUT MESSAGES OF ANALYSIS RESULTS
· (TENDENCY ANALYSIS OF BODY TEMPERATURE AND MENSTRUATION) "The temperature difference has become 0.3 degree or more."
· (TENDENCY ANALYSIS OF EXAMINATION RESULTS) "The LH value has been improved."
· (ACTION EXTRACTION) "Exercise A had been done last month."
· (DISEASE RISK WARNING) "There is a possibility of disease X."
· (PREGNANCY SUPPORT) "Ease of pregnancy is xx."

FIG. 22
INPUT EXAMPLE OF ONE DAY

DECEMBER 1, 2013 (SUN)

HEALTH DATA RECORDATION

◇OVULATION TEST ( POSITIVE): ✓
◇PREGNANCY TEST ( POSITIVE): ☐
◇TIMING METHOD ( SEXUAL INTERCOURSE): ✓
◇AMOUNT OF SECRETION:  ○SMALL  ○MEDIUM  ○LARGE

[EXAMINATION RESULTS]

- AMH              pM
- LH               mIU/mL
                   mIU/mL
- FSH              mIU/mL
                   mIU/mL
- P2               mIU/mL
- E4
- ENDOMETRIAL      mm
  THICKNESS
- FOLLICLE   LEFT ____ mm   RIGHT ____ mm

REGISTER

| HOME | GRAPH | CALENDAR | PARTNER | SETTINGS |

FIG. 23
INPUT EXAMPLE OF ONE DAY

DECEMBER 1, 2013 (SUN)

HEALTH DATA RECORDATION

◇ABOUT SYMPTOM  (DEGREE)

- HAVING A HEADACHE  ☑  LIGHT ▽
- HAVING A STOMACHACHE  ☐  ▽
- HAVING A BACKACHE  ☐  ▽
- ......  ☐  ▽

- BLUE FEELING  ☑  HEAVY ▽
- IRRITABILITY  ☐  ▽
- LETHARGY  ☐  ▽
- ......  ☐  ▽

◇ABOUT STRESS
○NO  ○LOW  ○MIDDLE  ◉HIGH

◇Please arbitrarily input other symptom, feeling or the like.

......

[ REGISTER ]

[HOME]  [GRAPH]  [CALENDAR]  [PARTNER]  [SETTINGS]

FIG. 24

SCREEN EXAMPLE INCLUDING SIMILAR USER INFORMATION

◆INFORMATION ON OTHER USERS SIMILAR TO YOU (USER X)

241 — CONDITIONS: PERSON OF (AGE) ABOUT 35, (* SIMILAR ATTRIBUTE)
( DISEASE) INFERTILITY, ( TREATMENT) IN-VITRO FERTILIZATION, SIMILAR TO YOU

242 —
| 1 ☆☆☆ | USER A ···(OMITTED)··· |
| 2 ☆☆ | USER B ···(OMITTED)··· |
| 3 ☆☆ | USER C ···(OMITTED)··· |
| 4 | ······ |

·DISPLAY OF LIST OF SIMILAR USERS
·DISPLAY OF SIMILAR USER INFORMATION
  (OVERVIEW / PART / DETAILS)

EXAMPLE OF DISPLAY OF COMPARISON BETWEEN USER AND SIMILAR USER

243 —
REGARDING TREATMENT

[YOU (USER X)]
·AGE 33 (2011): TIMING METHOD
·AGE 34 (2012): ARTIFICIAL INSEMINATION ONCE
·AGE 35 (2013): IN-VITRO FERTILIZATION TWICE
EGG COLLECTION THREE TIMES
           (AVERAGE 1.2 PIECES)

[USER C]
·AGE 33 (2011): TIMING METHOD
·AGE 34 (2012): ARTIFICIAL INSEMINATION ONCE
·AGE 35 (2013): IN-VITRO FERTILIZATION FIVE TIMES
EGG COLLECTION TWICE
(AVERAGE 3.5 PIECES)

244 ~ DISPLAY ORDER: [DEGREE OF SIMILARITY ▽]

[ADVANCED SEARCH] ~ 245  [STATISTICAL INFORMATION] ~ 246

FIG. 25
SCREEN EXAMPLE OF USE SETTINGS

251 — ◆SETTINGS OF SHARE ITEMS
......

252 — ◆SETTINGS OF CONDITIONS FOR DETERMINING SIMILAR USER

252a —
- [✓] USER ATTRIBUTE
- [✓] HEALTH INFORMATION ELEMENT
- [✓] ACTION INFORMATION ELEMENT
- [✓] ANALYSIS RESULT
- [✓] GRAPH

252b — ○USER ATTRIBUTE:
- (1) [AGE ▽]
- (2) [DISEASE ▽]
- (3) [TREATMENT ▽]
- (4) [ANAMNESIS ▽]
- (5) [··· ▽]
- (6) [··· ▽]

252c — ○HEALTH INFORMATION ELEMENT:
- [✓] BODY TEMPERATURE
- [✓] MENSTRUATION
- [✓] EXAMINATION RESULT (HORMONE)
- [ ] EXAMINATION RESULT (···)
- [ ] SYMPTOM
- [ ] MEDICATION
- [ ] ....

252d — ○ACTION INFORMATION ELEMENT:
- [ ] ACTION (EXERCISE)
- [ ] ACTION (DIET)
- [ ] ACTION (MUSIC)
- [ ] NOTE
- [ ] ....

252e — ○ANALYSIS TYPE:
- [✓] TENDENCY ANALYSIS
- [ ] ACTION EXTRACTION
- [ ] DISEASE RISK WARNING
- [ ] PREGNANCY SUPPORT

[ SET TO THESE CONDITIONS ]

253 — ◆SETTINGS OF PRIORITY OUTPUT ITEM
- (1) [USER ATTRIBUTE ▽]
- (2) [BODY TEMPERATURE-MENSTRUATION GRAPH AND ANALYSIS RESULT ▽]
- (3) [······ ▽]

FIG. 26
SCREEN EXAMPLE OF SEARCHING FUNCTION

◆ ADVANCED SEARCH  (∗ ALL USER TARGET)

261 — [SEARCHING CONDITIONS]

| | | | |
|---|---|---|---|
| USER NAME | — | SEX | FEMALE |
| AGE | 35 | MEDICAL INSTITUTION | HOSPITAL A |
| TREATMENT | IN-VITRO FERTILIZATION | EXAMINATION INSTITUTION | EXAMINATION COMPANY A |
| DISEASE | INFERTILITY | EXAMINATION | EXAMINATION A |
| ANAMNESIS | — | PREGNANCY | — |
| TREATMENT PERIOD | — | PARTNER | ...... |

261a

| | |
|---|---|
| BODY TEMPERATURE | TEMPERATURE DIFFERENCE ΔT ≥ 0.3 °C |
| MENSTRUATION | Menstrual cycle is xx days. |
| EXAMINATION RESULT | LH value is good. |
| SYMPTOM | HAVING A BACKACHE |
| MEDICATION | ...... |
| EXERCISE | EXERCISE A |
| DIET | DIET A |
| ... | ... |

261b

261c — KEYWORD [          ]

[ SEARCH WITH THESE CONDITIONS ]

- - - - - - - - - - - - - - - - - - - - - - - - - - - - -

262 — [SEARCH RESULT]

| 1 | USER E<br>··· (OMITTED) ··· |
|---|---|
| 2 | USER F<br>··· (OMITTED) ··· |

······  (∗ SIMILARITY ORDER)

FIG. 27

SCREEN EXAMPLE OF STATISTICAL INFORMATION

271 — ◆STATISTICAL INFORMATION
(∗ AGGREGATE RESULT OF SHARE INFORMATION OF SIMILAR USER)

271a — ITEM: ABOUT ACTION (EXERCISE) ▽

271b —

| 1 | EXERCISE A | USERS A, B, C, ⋯ |
|---|---|---|
| 2 | EXERCISE B | USERS D, E, ⋯ |
| 3 | EXERCISE C | USERS F, ⋯ |
| ⋯ | ⋯ | ⋯ |

DISPLAY ORDER: NUMBER ORDER ▽

272 — ◆STATISTICAL INFORMATION
(∗ AGGREGATE RESULT OF SHARE INFORMATION OF ALL USERS)

272a — ITEM: ABOUT MEDICAL INSTITUTION (HOSPITAL VISIT) ▽

272b —

| 1 | HOSPITAL A | ·TREATMENT A, B, C<br>·EXAMINATION A | (NOTE COMMENT)<br>·POLITE<br>·Waiting time was long. |
|---|---|---|---|
| 2 | HOSPITAL B | ·TREATMENT B, C, D<br>·EXAMINATION B | ⋯ |
| ⋯ | ⋯ | ⋯ | ⋯ |

272d — ITEM: ABOUT AGE WHEN TO UNDERGO TREATMENT, STATUS OF PREGNANCY ▽

272e —

AGE AND NUMBER OF PERSONS WHO HAVE UNDERGONE TREATMENT

·AVERAGE AGE: XX AGE

SUCCESS RATE OF PREGNANCY

SUCCESS 60%

SCREEN EXAMPLE

HEALTH CARE SYSTEM

CROSS-REFERENCE TO RELATED APPLICATION

This application is a continuation of International Application No. PCT/JP2016/064855, filed on May 19, 2016, which claims the foreign priority benefit under 35 U.S.C. § 119 of Japanese Patent Application No. 2015-106353, filed on May 26, 2015, the disclosures of which are expressly incorporated herein by reference in their entirety.

BACKGROUND OF THE INVENTION

1. Field of the Invention

The present invention relates to a technique of a service by information processing. The present invention relates to a technique of health care to care for physical and mental states (generically referred to as a "health state", including health, illness, symptom and the like of human beings. The present invention relates to a technique to support usage of medical care and examination of human beings (including a patient). The present invention relates to a technique of support to maintain and improve the health state. The present invention relates to a technique of obstetrics and gynecology department that deal with diseases, pregnancy, and childbirth peculiar to females and a technique of information processing related to reproductive medicine.

2. Description of the Related Art

Demand for an information processing service regarding support of health care and medical care user has been increasing. For example, a large number of males and females have problems regarding diseases peculiar to females, pregnancy and childbirth related to fertility of a couple. Since the number of eggs of a female decreases with her age and the eggs also age, a possibility of pregnancy becomes lower and the pregnancy carries a higher risk at older ages. Further, it has been studied that motility of sperm of a male also decreases with age. It is effective and important to consciously work on pregnancy, which is a result of joint activity of a male and a female, from young age. Early treatment and the like are effective and important for infertility. In addition to infertility, there are premenstrual syndrome (PMS), menopausal disorder, corpus luteum insufficiency, endometriosis, and the like as the diseases peculiar to females. As diseases specific to males, there are oligozoospermia and the like that influence on infertility.

As a technique to care for health states of females described above, there is service in which data on a basal body temperature of a user is inputted and recorded to a server from an application of a terminal, the data on the body temperature is displayed on a screen, general medical knowledge regarding a menstrual cycle and the like and advice on daily life are provided to the user.

As an example of prior art regarding management of an individual medical condition, Japanese Patent Application Publication No. 2011-501844 (hereinafter, referred to as "Patent Document 1") is recited. Patent Document 1 discloses that a patient who is an individual user inputs medical condition evaluation indexes and information on interventions such as administration of medicine via a screen and they are displayed on the screen with line graphs. The medical condition evaluation indexes indicate qualitative values such as mood and the like, and quantitative values such as a blood pressure, a body temperature and the like. The interventions indicate activities related to a medical condition such as treatment, medicine, diet, exercise, and the like. Patent Document 1 is a technique for observing a state of influence on the medical condition by actions of the patient such as taking medicine on his or her medical condition.

SUMMARY OF THE INVENTION

Conventional technique regarding pregnancy support and diseases peculiar to females have the following problems. (1) The provided medical information is general commentary, enlightenment information, or the like and is thus insufficient, and it is difficult to interpret medical information regarding the health state and of the user. (2) It takes time and effort to input data of the health state of the user, and it is difficult to keep a regular history, and it is thus difficult to analyze his or her own health information. In particular, the conventional service is functionally insufficient for health care in a field including pregnancy and infertility of females.

(1) The information provided by the conventional service is information on illness, drugs, perspective on basal body temperature, and explanation of an ovulation day, and is information uniformly enlightening all users. Further, conventionally, the user merely receives an examination result paper regarding examination results. There has been no service that the user can know details of examination items, relationships among the examination items, information appropriate for female hormone values and the like of the examination results, his or her current health state based on the medical information thereof, and the like.

For that reason, it is difficult for the user to understand how to interpret and determine the values of the body temperature and the examination results and other relevant medical information, which relate to his or her health state and the contents of the treatment and the examinations. Further, it is difficult for the user to determine what kind of treatment and examinations should be taken and what kind of actions, such as exercise and diet, should be taken in order to maintain or improve his or her health state. For example, regarding limited information contacted from gynecology departments, obstetrics and gynecology departments, hospitals specialized in in-vitro fertilization, which have been contacted, the user hardly understands and is concerned about the health state including his or her body temperature and menstruation (referred to also as "menstrual period"), states of female hormones, a possibility of pregnancy or infertility, a situation and meaning of taking medicine, a possibility of peculiar diseases, and the like.

Regarding the above, the user conventionally exchanges body temperature, examination results, symptoms, medical information, and the like via a bulletin board or the like on the Internet. For example, topics are female hormone values of blood examination results, determination results of whether each value or result is normal or not, and the like. However, these pieces of information are prosaic, and it is thus difficult to determine or obtain information required for each of the users.

(2) Further, there has conventionally been needs that the user wants to view information regarding a health state, treatment, examinations and the like of other persons, and to make them a reference for his or her activities such as treatment. For example, in a case where the user is interested in pregnancy activities and infertility treatment, the user wants to obtain information of other persons who have already tackled the pregnancy activities and the infertility treatment, and to make them a reference. In that case, the user has to search information of the other persons that are related to his or her interest, situations, and the like from much information via the Internet or the like. However, it may take much time and effort to search the information, and the user cannot obtain useful information of the other persons well frequently. Further, there is a possibility that the user cannot utilize it well even though the user obtains information of other person whose situation and the like are different from those of the user.

(3) Input of data such as body temperature by the user generally takes time and effort and is troublesome. For that reason, it is difficult for the user to have motivation and a willingness to continuously register the data. Further, it is difficult for the user to recognize and grasp influences and results of the treatment and the actions that have actually been taken in order to improve the health state of the user, recover his or her medical condition, and the like. This point also relates to the difficulty having the motivation and a willingness described above. Further, in a case where the user regularly visits a hospital for pregnancy, the examination content is often kept by a paper medium. However, it is difficult to regularly accumulate and search the information.

It is an object of the present invention to provide techniques capable of realizing, regarding techniques of the health care and the like described above, support of obtainment regarding a health state and medical information of a user, enhancement and advancement of provided information regarding the health state and the medical information of the user, reduction of time and effort to input data by the user, thereby comprehensively allowing care of the health state of the user and support of treatment and examination.

A representative embodiment of the present invention relates to a health care system configured to provide an information processing service to care for a health state of a user, and to include the following configuration.

A health care system according to one embodiment includes:
  a server apparatus configured to provide service for caring for a health state of each of users; and
  terminals of the users,
  wherein the server apparatus includes:
    a data managing unit configured to register and manage user information containing at least one of attribute information, health information, or action information as share information of a group of users on the basis of an operation from the terminal of the user, the attribute information containing at least one of sex, age, diseases, treatment, medical institutions, examination institutions, or anamneses of the user, the health information containing time series data of at least one element containing measurement items that include a body temperature of the user, menstruation, examination results, medication, or symptoms, the action information containing time series data of actions or arbitrary texts;
    a checking unit configured to check similarity between the users in the share information, determine a similar user of each of the users, and store a determination result as check information; and
    an outputting unit configured to output share information of the similar user of the user to the terminal of the user on the basis of the check information.

According to the representative embodiment of the present invention, regarding techniques of the health care and the like described above, it is possible to support of obtainment regarding a health state and medical information of a user, enhance and advance provided information regarding the health state and the medical information of the user, reduce time and effort to input data by the user, thereby comprehensively allowing care of the health state of the user and support of treatment and examination.

BRIEF DESCRIPTION OF THE DRAWINGS

FIG. 1 is a view showing a configuration of a health care system according to one embodiment of the present invention.

FIG. 3 is a view showing a processing flow of management and analysis of health data among major processing of the health care system.

FIG. 5A is a view showing a configuration example of user attribute information.

FIG. 5B is a view showing a configuration example of health information.

FIG. 5C is a view showing a configuration example of a portion of an examination result in the health information.

FIG. 5D is a view showing a configuration example of action information.

FIG. 6 is a view showing a first configuration example of user setting information.

FIG. 7 is a view showing a second configuration example of the user setting information.

FIG. 8 is a view showing a third configuration example of the user setting information.

FIG. 9 is a view showing a configuration example of medical examination information.

FIG. 10 is a view showing an example of a body temperature-menstruation graph.

FIG. 11 is a view showing a configuration example of examination result data.

FIG. 12 is a view showing a first example of an examination result graph.

FIG. 13 is a view showing a second example of the examination result graph.

FIG. 14 is a view showing a configuration example of calendar input information.

FIG. 15 is a view showing a configuration example of check information.

FIG. 16 is a view showing an example of determination of a similar user by user attribute comparison of check processing.

FIG. 17 is a view showing an example of graph comparison of the check processing.

FIG. 18 is a view showing an example of action comparison and symptom comparison of the check processing.

FIG. 19 is a view showing a configuration example of output information.

FIG. 20 is a view showing a screen example including medical record information.

FIG. 22 is a view showing a case where an examination result and the like are recorded as the screen example of the input for unit of one day.

FIG. 23 is a view showing a case where a symptom and the like are recorded as the screen example of the input for unit of one day.

FIG. 24 is a view showing a screen example including display of the similar user information.

FIG. 25 is a view showing a screen example of user setting.

FIG. 26 is a view showing a screen example of a searching function.

FIG. 27 is a view showing a screen example of display of statistical information.

DETAILED DESCRIPTION OF THE INVENTION

Figure 2A:
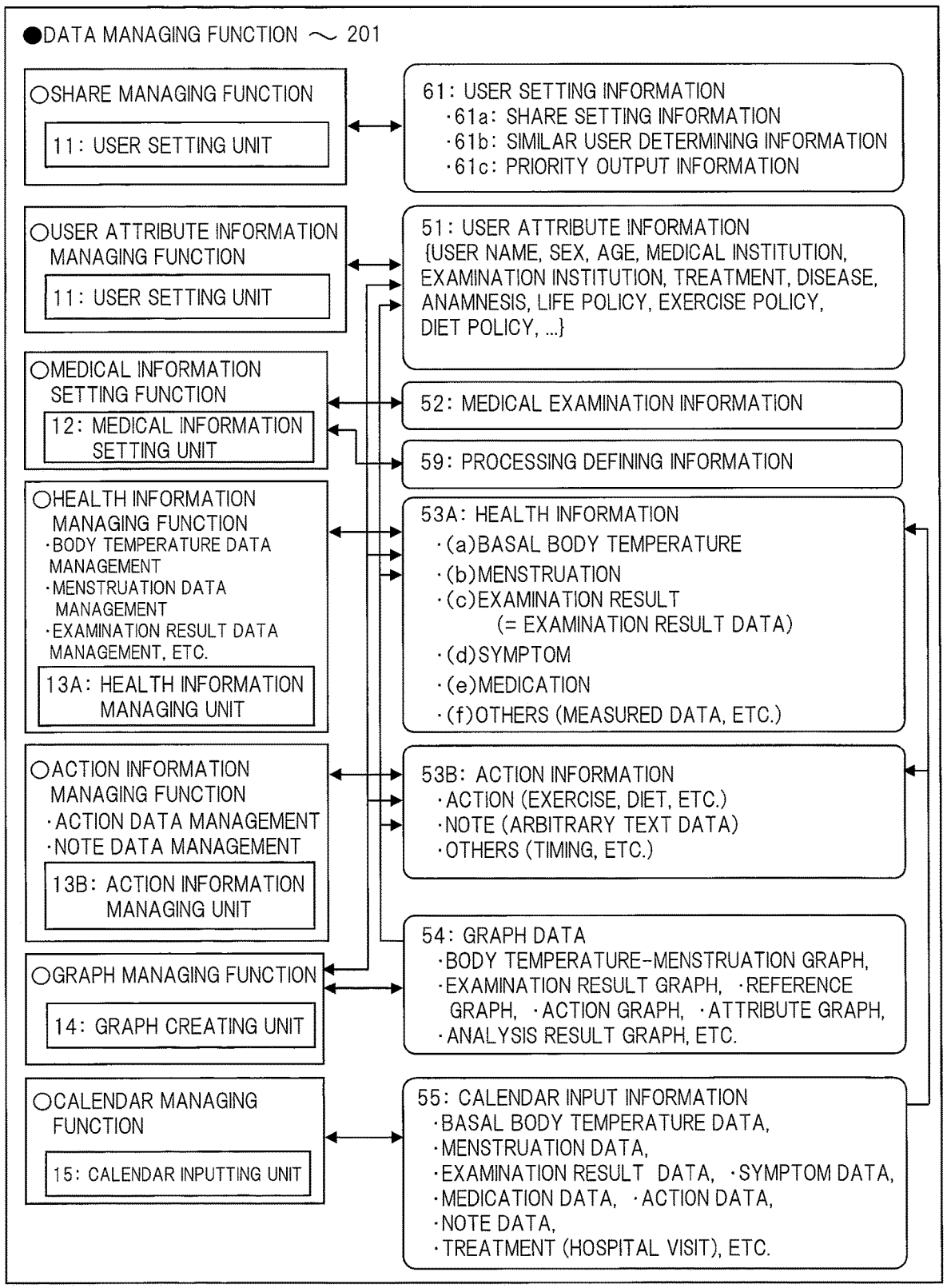
FIG. 2A is a view showing functions of the health care system and an outline of data.

Hereinafter, a health care system according to one embodiment of the present invention will be described in detail with reference to the drawings. As for definitions of the terms used in the present specification, disease is a generic term that contains so-called sickness, illness, disease, syndrome, disorder, and the others. The disease is managed while containing a name, a type, a degree, a stage, transition, details, and the like. The disease is managed while containing a state where a disease is suspected, a state of currently having a disease, a state where a disease is recovered, and the like. The disease includes one based on a diagnosis by a doctor or the like, and one based on self-recognition and subjectivity of a user. The disease especially contains diseases concerned with the fields of obstetrics and gynecology department and reproductive medicine. However, the disease may also contain diseases of other medical fields.

Treatment is a generic term that contains clinical examination, treatment, medical activities, prescription and the like by a medical institution, therapy and the like adopted by the user according to permission by the medical institution. The treatment is managed while containing a name, a type, a stage, transition, details, and the like. As examples of the treatment, there are counseling, a timing method (which is a method in which sexual intercourse is carried out so as to coincide with an ovulation day of the user), artificial insemination, in-vitro fertilization, microinsemination, surgery of an ovary or a uterus, injection of medicine, and the like.

An examination is a medical examination, and is a generic term that contains a test and the like. As examples of the examination, there are a blood examination, a urine examination, a semen examination, a physiological function examination by ultrasonic waves or an endoscope, an imaging examination, and the like. The examination contains an examination for each specific disease such as sexually transmitted diseases. The examination also contains a general health examination.

A symptom is a generic term that contains an actual state of exercise, diet, sleep, excretion, and the like, a mood, a physical condition, and the like, and may contain stress. The symptoms and stress include various kinds of physical and mental symptoms and stress that are subjectively recognized by the user. An action is a generic term for exercise, diet, sleep, excretion, sexual intercourse, other various activities on a daily life, which are subjectively planed by the user for the purpose of improving the disease.

The health care system according to the present embodiment is configured to care for a health state of the user, which includes an event of diseases peculiar to females (containing symptoms with increase or decrease in female hormones), pregnancy, infertility, and the like, in a field including obstetrics and gynecology departments and reproductive medicines (including urology departments in case of males), and to provide service to support activities containing treatment and examinations of the user. In the present service, health information of each individual user is registered and managed, a health state of each individual user is analyzed, and information such as a message according to a state of each individual user is provided.

In the present service, management to share information among users is carried out on the basis of management of information that contains health information of each user. In the present service, while referring to the share information, users whose situation and the like are similar to the user is checked, and similar user or similar users is determined for each user. In the present service, similar user information, that is, share information of other similar user based on a situation and the like of the user is automatically provided to each user on the basis of the check.

The service described above allows the user to easily browse (or read) and obtain useful information, which contains attributes, a health state, and the like of other user who is similar to the user with respect to attributes of disease and treatment, situations of a health state and pregnancy, and the like, and this makes it possible for the user to consult activities of the user such as treatment and pregnancy and its determination.

[System]

FIG. 1 shows an overall configuration of a health care system according to the present embodiment. In the health care system according to the embodiment, a server 1 by a service provider and a plurality of terminals 2 of respective users are connected via the communication network 9. Each of the users is a person including a patient and the like, and possesses the terminal 2 and a medical apparatus 3. A terminal 4 of the medical institution or examination institution may be connected to the terminal 2 of the user via a communication network 9. The terminal 4 of the medical institution or examination institution may be connected to the server 1 via the communication network 9. A server of other provider may be connected to the server 1 to provide the service by cooperating with the server 1.

Hospitals and the like are recited as the medical institution. An examination company, an examination department in the medical institution, and the like are recited as the examination institution. A server on a Web site for providing medical information and hospital information, a server of a communication carrier for providing management of user information and settlement service, and the like are recited as the server of the other provider.

The server 1 has a service unit 10 and a DB (database) 50. On the basis of processing of a server program of a server computer, the service unit 10 provide, to the terminal 2 of the user that accesses via the communication network 9, a screen and a process for service of health care while using information of the DB 50. The DB 50 is configured by a storage or the like, stores data and information for the service therein, and is managed securely. The server 1 may be a cloud computing system or the like.

The terminal 2 of the user may be various kinds of computers such as a PC, a smartphone, a tablet terminal, and a wearable terminal, and includes known elements such as a CPU, a ROM, a RAM, an inputting unit, an outputting unit, and a communication unit. The terminal of the user includes an application 20, a body temperature-menstruation data inputting unit 21, and an examination result data inputting unit 22.

The application 20 is a program for executing processing to communicate with the service unit 10 of the server 1 and receive the service of the health care, and provides a user interface containing a screen of the service. The application 20 includes implementation of functions corresponding to the body temperature-menstruation data inputting unit 21 and the examination result data inputting unit 22.

The body temperature-menstruation data inputting unit 21 is configured to input body temperature data and menstruation data of the user. The body temperature data are time series data that contain a date of measurement, a numerical value, and the like of basal body temperature. The menstruation data are time series data that contain information such as a menstruation date. The examination result data inputting unit 22 is configured to input examination result data of the user. The examination result data are time series data that contain a date of an examination, an examination item, a numerical value thereof, and the like. The examination item includes an endocrinological examination and the like of female hormones. The body temperature-menstruation data inputting unit 21 and the examination result data inputting unit 22 may be automatically transferred in addition to a manual input, and include a wireless communication interface, for example, to input data from the outside via wireless communication.

The medical apparatus 3 includes a thermometer, an examination checker, and the like that are used to measure the basal body temperature by the user. The medical apparatus 3 includes, as sensor functions, a measuring function for body temperature and the like. The medical apparatus 3 is allowed to store data on the body temperature measured by the sensor function, and the like, and display and output to the outside. The body temperature-menstruation data inputting unit 21 of the terminal 2 of the user is configured to input the data such as the body temperature from the medical apparatus 3 by communication.

The terminal 2 of the user and the medical apparatus 3 may be provided with functions to measure other items in addition to the body temperature. The terminal 2 of the user may measure numerical values of the body temperature and the other items, and register time series data of these items to the server 1 as measured data (referred to also as "vital data"). As examples of items of the measured data, there are the body temperature, a heart rate, a pulse, a blood pressure, breathing, and the like.

The measurement items and the measured data can be registered either in a case of measuring them by the user himself or herself or in a case of measuring them in the medical institution or the examination institution. The examination item and the examination result data can be registered either in a case of an examination by the user himself or herself or in a case of an examination by the medical institution or the examination institution.

Each of the terminal 2 of the user and the medical apparatus 3 may be a wearable terminal with sensor functions. In that case, a wearable terminal is configured to automatically measure or examine body temperature and numerical values of predetermined other items related to the health state of the user, and record the data. The terminal 2 and the medical apparatus 3 may be integrated into one element. A plurality of the medical apparatuses 3 may be provided in accordance with measurement items or examination items.

A person such as a doctor of the medical institution or an examiner of the examination institution uses the terminal 4. Further, the user may use the terminal 4 at his or her own home. The terminal 4 may be a dedicated medical apparatus, a dedicated examination device, a hospital system, or the like in addition to various kinds of computers in the similar manner to the terminal 2 of the user. Alternatively, the terminal 4 may be dedicated pharmaceuticals, an examination checker, or the like. For example, the doctor, the examiner, or the user manually inputs information on treatment and the like of the user (so-called medical record information) and examination result information into the terminal 4. Further, in a case where the terminal 4 is any one of the medical apparatus, the examination device, and the hospital system, the terminal 4 automatically transfers the data. The terminal 4 may be provided with an examination result data outputting function to output the examination result data of the user to the outside. The examination result data inputting unit 22 allows the terminal 2 of the user to input the examination result data by communication from the examination result data outputting function of the terminal 4.

The service unit 10 includes a user setting unit 11, a medical information setting unit 12, a health information managing unit 13A, an action information managing unit 13B, a graph creating unit 14, a calendar inputting unit 15, an analyzing unit 16, a checking unit 17, an outputting unit 18, a searching unit 19, and an auxiliary unit 70. Each unit is realized by software program processing. The DB 50 stores user setting information 61, user attribute information 51, medical examination information 52, health information 53A, action information 53B, graph data 54, calendar input information 55, analysis information 56, check information 57, output information 58, processing defining information 59, and the like.

The service unit 10 includes a function to provide basic service to the terminal 2 of the user in addition to the above functions, and manages information for the processing in the DB 50. The service unit 10 appropriately obtains or refers to necessary information from servers of other providers to carryout processing for the basic service. The basic service has a function to provide the latest medical information or the latest health information, a function to search the medical institution, pharmaceuticals (containing vitamins and Kampo medicines) and the like, and a function for bulletin boards (such as a community, media on which a plurality of persons reads and writes), blogs, and the like.

The user setting unit 11 includes a processing unit for the user settings and registration of the user attribute information. The user setting unit 11 carries out processing to provide a screen for the user settings in the terminal 2 of the user and register setting information of each user inputted by the user via the screen as the user setting information 61. Further, the user setting unit 11 carries out processing to provide a screen for registering the user attribute information to the terminal 2 of the user, and to register the attribute information of the user, which is inputted by the user via the screen, as the user attribute information 51.

In this regard, the user attribute information 51 and the user setting information 61 may be integrated into one element.

The medical information setting unit 12 carries out processing to set management information for the present system, which contains the medical examination information 52 and the processing defining information 59, on the basis of an input by a manager of the present system. The medical examination information 52 is a DB in which a plurality of medical institutions, a plurality of examination institutions, and management information regarding medical care and examinations are contained. In the processing defining information 59, definition information on individual processing logics, which is used when to carry out various kinds of analysis and checks, is set as the management information for the present system.

The health information managing unit 13A carries out processing to manage, in the DB 50, time series health data of each of various kinds of elements inputted by the user through the application 20 of the terminal 2 of the user, that is, the elements of the body temperature, the menstruation, the examination results, the symptoms, the medication and the like as the health information. In particular, the health information managing unit 13A receives the body temperature data and the menstruation data inputted and transmitted through the body temperature-menstruation data inputting unit 21 of the terminal 2, and stores them as part of the health information 53A. Further, the health information managing unit 13A receives the examination result data inputted and transmitted through the examination result data inputting unit 22 of the terminal 2, and stores them as part of the health information 53A.

The action information managing unit 13B carries out processing to manage, in the DB 50, arbitrary text data such as actions, notes (or tweet) and the like inputted by the user through the application 20 of the terminal 2 of the user as the action information 53B.

The graph creating unit 14 carries out processing to create various kinds of graphs by using various kinds of time series data in the user information, save the created graphs in the DB 50 as the graph data 54, and to display each of the graphs on the screen.

The graph creating unit 14 creates a body temperature-menstruation graph by using the body temperature data and the menstruation data of the health information 53A, for example, stores the graph as part of the graph data 54, and displays the body temperature-menstruation graph on the screen. Further, the graph creating unit 14 creates an examination result graph by using the examination result data of the health information 53A, stores the graph as part of the graph data 54, and displays the examination result graph on the screen. Further, the graph creating unit 14 creates an action graph by using the action information 53B, stores the graph as part of the graph data 54, and displays the action graph on the screen. Further, the graph creating unit 14 creates an attribute graph by using the attributes of the user attribute information 51, stores the graph as part of the graph data 54, and displays the attribute graph on the screen. Further, the graph creating unit 14 creates an analysis result graph by using the analysis information 56, stores the graph as part of the graph data 54, and displays the analysis result graph on the screen.

The graphs include a graph in which numerical values of a body temperature or the like are plotted as a vertical axis by using a time as a horizontal axis, for example. The body temperature-menstruation graph is a graph in which the body temperature graph and the menstruation graph are integrated, but may be managed so as to be separated from each other. The examination result graph contains a graph of numerical values of the examination item such as the endocrinological examination and the like.

The calendar inputting unit 15 is a processing unit configured to assist to input and manage the health information 53A of the health information managing unit 13A and the action information 53B of the action information managing unit 13B. The calendar inputting unit 15 carries out processing to provide a screen including the calendar to the terminal 2 of the user, and register, as the calendar input information 55, the user input information inputted by the user via the screen, which contains the basal body temperature, the menstruation, the examination results, the symptoms, the medication, the actions, the notes, the treatment (hospital visit), and the other information, regardless either a static method or a dynamic method. Various kinds of user input information can be registered for each date of the calendar in time series. Each piece of the user input information can be inputted by means of at least one of a dedicated screen, an input field or the calendar.

By using the user attribute information 51, the medical examination information 52, and the processing defining information 59, the analyzing unit 16 carries out processing of respective analyses including notice information extraction such as a tendency analysis and disease risk determination, action extraction, and pregnancy support. The analyzing unit 16 carries out processing of various kinds of tendency analyses in the health information 53A and the action information 53B of the user, and stores result information thereof in the analysis information 56. The analyzing unit 16 carries out action extraction processing in a health state by the analysis information 56 of the user and the action information 53B registered in the calendar input information 55, and stores result information thereof in the analysis information 56. The analyzing unit 16 carries out disease risk determination processing and pregnancy support processing by using a combination of the health state by the analysis information 56 of the user and the elements of the health information 53A and the action information 53B described above, and stores result information thereof in the analysis information 56.

The checking unit 17 carries out check processing regarding a similar user in the user attribute information 51, the health information 53A, the action information 53B, the graph data 54, the analysis information 56, and the like of the user on the basis of the user setting information 61. The checking unit 17 checks similarity among respective users in a group of users in accordance with a condition set to the user setting information 61; determines a similar user of each user; and stores a result of the check processing in the check information 57.

In the check processing, the checking unit 17 compares attribute values of the user attribute information 51, values of the elements of the health information 53A or the action information 53B, the graphs, values of analysis results, or the like between the users to calculate a degree of similarity, which is an index value indicating similarity between users. The checking unit 17 determines other user similar to the user as a similar user by using the degree of similarity, and stores information in which the user is associated with the other user in the check information 57.

The checking unit 17 determines similar user information to be outputted to each of the users on the basis of a result of the check processing, and stores the information in the check information 57 or the output information 58. The similar user information to be outputted contains various kinds of user information that are registered in the present system as the share information of the group of users, and are information on a predetermined attribute of the user attribute information 51, predetermined data on the elements of the health information 53A and the action information 53B, predetermined analysis result information and predetermined message information, and the like.

The outputting unit 18 carries out, on the basis of the analysis information 56, the check information 57, and the output information 58 described above, outputting processing of information, which contains a message according to the health state of each user and the similar user information of each user, on the screen of the terminal 2 of the user, and manages the information in the output information 58.

The auxiliary unit 70 carries out processing corresponding to an auxiliary function, which is other function of the present service while cooperating with the application 20, and manages information for them in the DB 50.

[Function and Data]

Figure 2B:
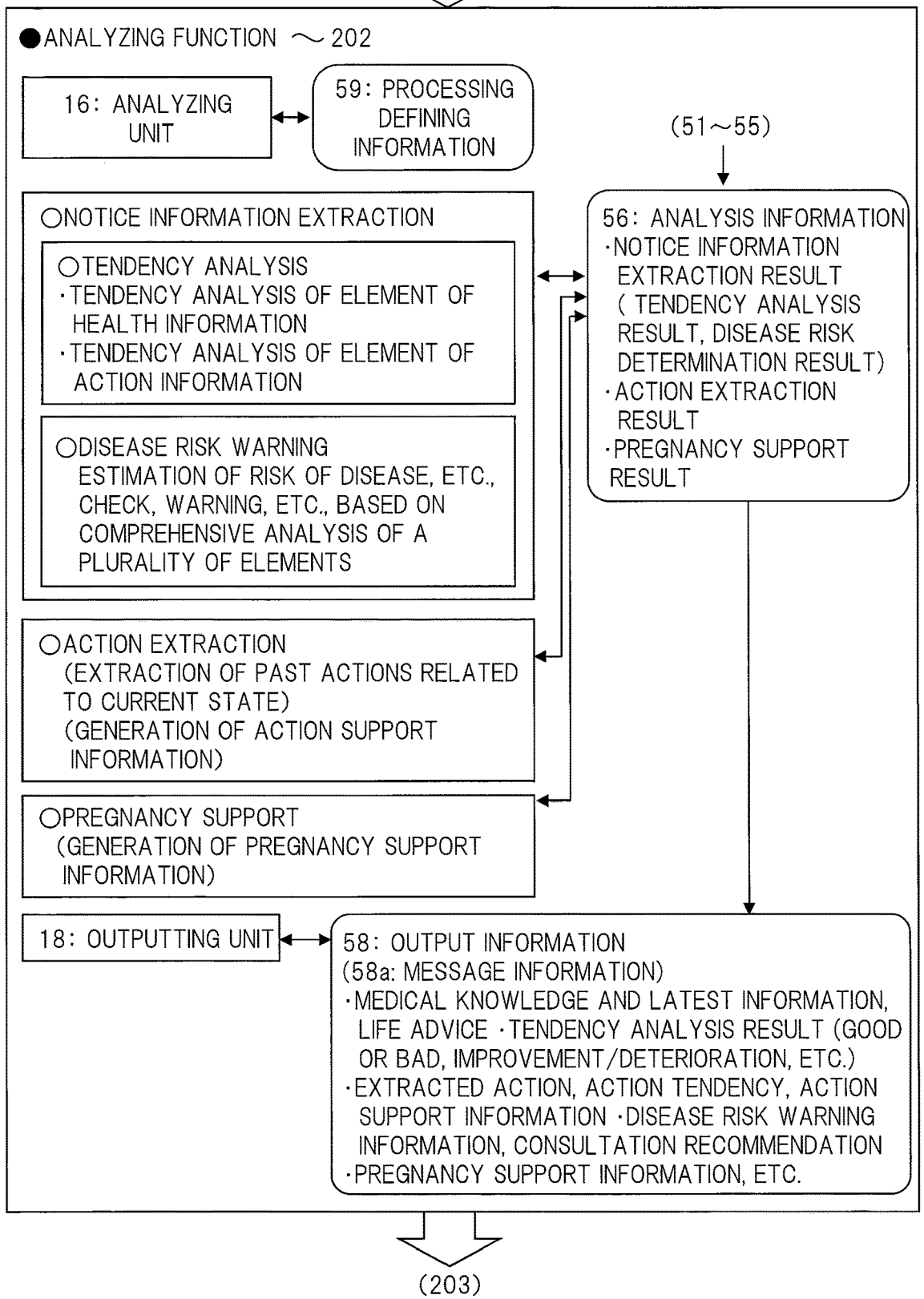
FIG. 2B is a view showing the functions of the health care system and the outline of the data.
Figure 2C:
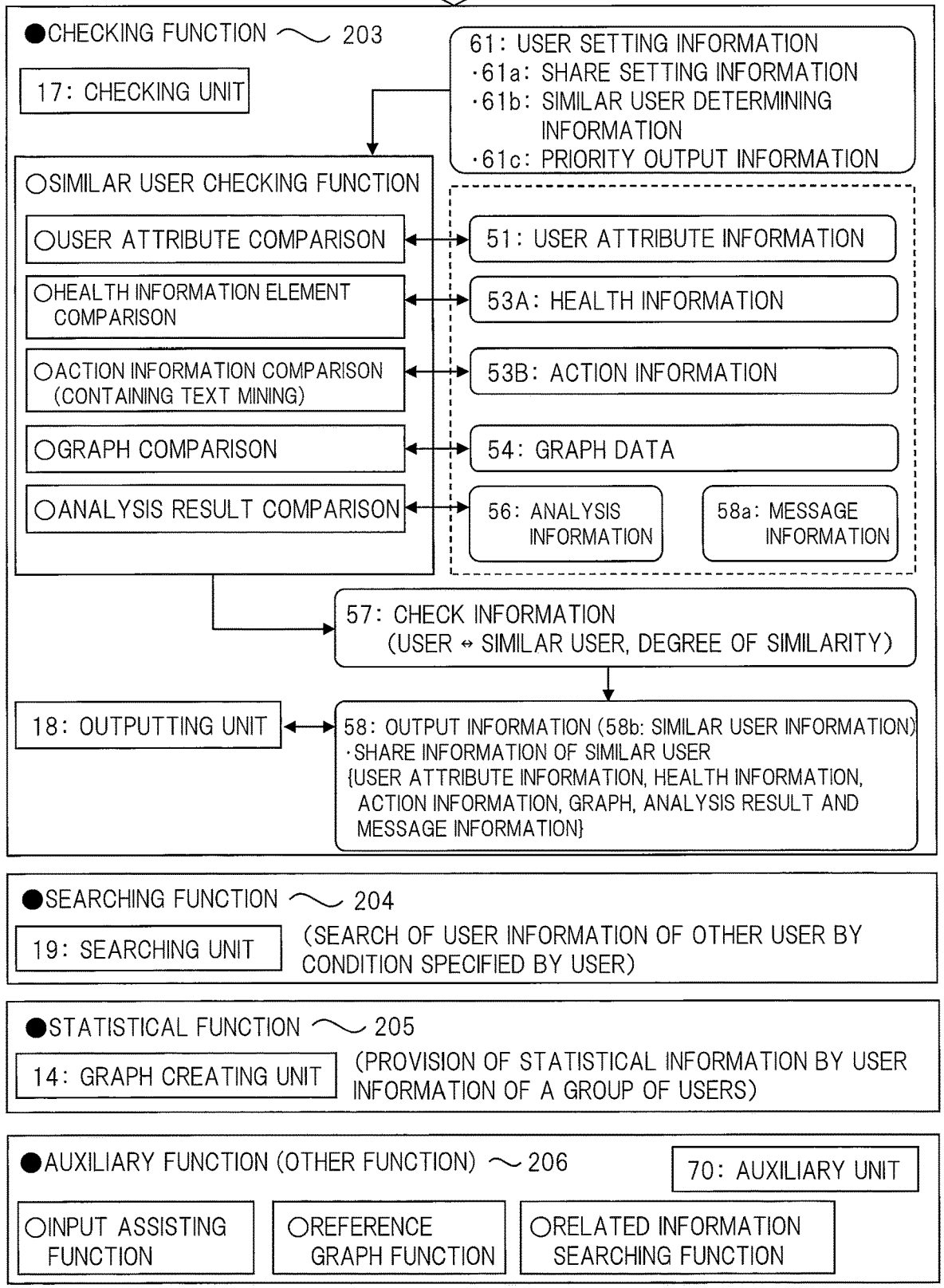
FIG. 2C is a view showing the functions of the health care system and the outline of the data.

FIG. 2A, FIG. 2B and FIG. 2C show service to be provided by the health care system according to the present embodiment and the corresponding functions, and an outline of data and information to be managed. This health care system includes, as major functions, (1) a data managing function 201, (2) an analyzing function 202, (3) a checking function 203, (4) a searching function 204, (5) a statistical function 205, and (6) an auxiliary function 206.

(1) As shown in FIG. 2A, the data managing function 201 includes a share managing function, a user attribute information managing function, a medical information setting function, a health information managing function, an action information managing function, a graph managing function, a calendar managing function, and the like to manage the user setting information 61, the user attribute information 51, the medical examination information 52, the processing defining information 59, the health information 53A, the action information 53B, the graph data 54, the calendar input information 55, and the like. The data managing function 201 includes a function to record and centrally manage data regarding a health state of each of individual users. The data managing function 201 registers, to the DB 50, user input information that is inputted by the user through the screen of the application 20 of the terminal 2 at any time.

(1-1) The share managing function is realized by using the user setting unit 11, and is a function that includes management of the user setting information 61 for each user by the manager of the present system or the individual user. The share managing function carries out, to the user setting information 61, settings related to share of data and information of the group of users and settings related to check of the similar user and provision of information. For further information, the user setting information 61 contains share setting information 61a, similar user determining information 61b, and priority output information 61C for each user.

(1-2) The user attribute information managing function is realized by using the user setting unit 11, and is a function that includes registration and management of the user attribute information 51 of each user. The user attribute information 51 contains, as items of the attribute, a user name, sex, age, medical institutions and examination institutions to be utilized, a state of treatment, disease, and anamnesis, life policy, exercise policy, diet policy, and the like.

(1-3) The medical information setting function is realized by using the medical information setting unit 12, and is a function to set and manage the medical examination information 52 and the processing defining information 59 on the basis of an operation of the manager.

Information regarding each of the plurality of medical institutions and examination institutions is set to the medical examination information 52 as the management information for the present system. The medical examination information 52 contains settings and management of reference information that are used at the time of the analysis and the check. The present system appropriately refers to the medical examination information 52, determines a medical institution, an examination and the like for each user, and carries out analysis and/or check according to them.

Definition information on individual processing logics, which are used when to carry out various kinds of analysis, check, and the like for an analysis function is set to the processing defining information 59. The processing defining information 59 contains management of information on criteria to be applied on the basis of the medical examination information 52.

(1-4) The health information managing function is realized by using the health information managing unit 13A, and includes a function to record and centrally manage data of each element in the health information of each individual user. The health information managing function includes, for each user, a function to manage basal body temperature data, a function to manage the menstruation data, a function to manage the examination result data, a function to manage symptom data, and the like.

The health information 53A contains, as the elements, (a) basal body temperature, (b) menstruation, (c) examination result, (d) symptom, (e) medication, and (f) others. The basal body temperature of (a) is an example of the measurement item and the measured data, and may include measured data of a plurality of other measurement items. The examination result of (c) is examination result data (will be described later), and contains numerical values of a plurality of examination items, numerical values of a plurality of types of endocrinological examination items, and the like. The symptom of (d) includes stress. Information on the medication of (e) contains information on prescription of medicine by the medical institution, information on taking of the medicine by the user, and information on history thereof.

(1-5) The action information managing function is realized by using the action information managing unit 13B, and includes a function to record and centrally manage data of each element of the action information of each individual user. The action information managing function includes a function to manage action data and a function to manage note data for each user.

The action information 53B contains action data and arbitrary text data, such as note data and the like. The action data contain data of each of various kinds of actions related to life habit, and contain exercise data and diet data, for example. The actions include exercise therapy, diet therapy, music therapy, and the like. The note includes an arbitrary text indicating a feeling, a memo, and the like.

(1-6) The graph managing function is realized by using the graph creating unit 14, and manages various kinds of the graph data and information related to them, which contain the body temperature-menstruation graph, the examination result graph, the action graph, the attribute graph, the analysis result graph, and the like that indicate the health state of the user. The graph managing function sets and manages information related to a reference graph (will be described later) in addition to the graphs of each user.

(1-7) The calendar managing function is realized by using the calendar inputting unit 15, and manages the screen including the calendar for registering and displaying the user input information, and the calendar input information 55. The calendar managing function displays the calendar on the screen of the application 20 of the terminal 2 of the user, and controls registration and display of various kinds of information with respect to dates of the calendar (basal body temperature, menstruation, examination results, symptoms, medication, actions, notes, treatment, and the others). The user input information is recorded and centrally managed in time series in form of the calendar. Input and/or display of a current date, past dates and future dates are possible in the calendar.

(2) In FIG. 2B, the analyzing function 202 is realized by using the analyzing unit 16 and the outputting unit 18, and includes an analysis function and a message outputting function. The analysis function includes a notice information extracting function, an action extracting function, and a pregnancy support function, and manages the analysis information 56. The message outputting function manages the output information 58. The output information 58 contains message information 58a. The analyzing function 202 carries out advanced analysis regarding the health state of each user on the basis of the medical examination information 52 and/or the processing defining information 59 by using each of the data by the data managing function 201 of (1) described above, that is, the user attribute information 51, the health information 53A, the action information 53B, and the like of each user. The analyzing function 202 then outputs information containing an advanced message according to the health state of each user, which is a result of the analysis.

(2-1) A tendency analyzing function includes a function of tendency analysis regarding each element of the health information 53A and the action information 53B, that is, a function of tendency analysis of body temperature and menstruation, a function of tendency analysis of examination results, a function of tendency analysis of actions, a function of tendency analysis of symptoms, and the like. In processing for the tendency analysis, a state of the tendency such as absolute good or bad, relative improvement or deterioration, and the like in time series values of the elements such as the body temperature of the user is determined on the basis of a numerical value of a predetermined criterion. The tendency contains variation in a numerical value in time series. The tendency contains a change in each element for past fixed period of time, for example, and a change in quantity, frequency or continuity, for example.

The function of the tendency analysis of the body temperature and the menstruation analyzes the health state containing tendency of the body temperature and the menstruation of the user by using numerical values and graphs of the body temperature, the menstruation, and the like in the health information 53A for each user. This function includes calculation and determination of a difference in temperature and a value of a predetermined item such as a menstrual cycle (will be described later). The function of the tendency analysis of the examination result analyzes the health state containing tendency of the value of the examination result of the user by using numerical values and graphs of the examination result data and the like in the health information 53A for each user. This function includes calculation and determination of a value of a predetermined item regarding the examination result. The function of the tendency analysis of the action analyzes tendency of the action of the user by using values and graphs of the action in the action information 53B for each user. The function of the tendency analysis of the symptom analyzes tendency of the symptom by using values and graphs of the symptom in the health information 53A for each user. Tendency analysis of other elements is similar.

(2-2) The action extracting function extracts information on past actions that are estimated to be related to or influence on the health state of the user, such as current body temperature, menstruation, examination results, symptoms, and the like, by using the action information 53B for each user, and presents the information to the user. The health state of the user is determined by using the results of the tendency analysis. Further, the action extracting function generates action support information for each user by using the action information 53B of the user and the action information 53B of the similar user of the user, and presents the information to them. The action support information is information for proposing an action that has a possibility for useful to improvement of the health state of the user.

(2-3) A disease risk warning function estimates and checks the health state containing a possibility of a disease or the like of the user by means of comprehensive analysis using a combination of the attributes of the user, the health information, and the elements of the action information as described above. The disease risk warning function then provides a message according to the result by using the message outputting function. The disease risk warning function outputs the message for warning a possibility of a disease and risk in accordance with the result. A check target includes various kinds of diseases peculiar to females, and the like. In other words, the warning is an alert for suggesting a possibility or encouraging attention calling.

(2-4) The pregnancy support function analyzes and grasps the health state related to pregnancy and fertility of the user by using the attributes, the health information, the elements of the action information, the analysis result of the user as described above. The pregnancy support function generates pregnancy support information for heightening a possibility of the pregnancy according to the health state of the user, and provides it to the user. The pregnancy support information contains an advice on a pregnancy activity with a partner of the user, and the like.

The following is contained as an outline of the output information 58 by the functions of (2) described above. The message information 58a of the output information 58 contains general medical knowledge, the latest information, life advices, tendency analysis result information, extracted actions, action tendency, action support information, an alert indicating attention calling of a possibility of a disease by check results, consultation recommendation regarding treatment, examinations, hospitals and the like, the pregnancy support information, and the like. The tendency analysis result information contains numerical values of the health state of the user, good or bad thereof, information for communicating a state of tendency such as improvement or deterioration thereof, and information for explanation and interpretation of the state. The analysis result and the message information are reference information by the analysis peculiar to the present system, which is to be provided to each individual user.

(3) In FIG. 2C, the checking function 203 is realized by using the checking unit 17 and the outputting unit 18. The checking function 203 includes a similar user checking function; manages the check information 57 and the output information 58; and provide the similar user information to every user. The checking function 203 checks similarity of users on the basis of the user setting information 61 of each user in the user attribute information 51, the health information 53A, the action information 53B, the graph data 54, the analysis information 56, and the like for the group of users. The checking function 203 calculates the degree of similarity that is the index value indicating similarity between the users; determines a similar user of each of the users; and stores a check result in the check information 57. The check information 57 contains information in which each of the users is associated with the similar user who is other user by using the degree of similarity.

The checking function 203 determines the similar user information for provision and output to each user on the basis of the check information 57, and stores it as similar user information 58*b* in the check information 57 or the output information 58. The similar user information to be outputted is information on a predetermined item of the share information of the similar user, and contains data containing an attribute value of the user attribute information 51, a graph of the element of the health information and the action information, and the analysis result or the message information.

The checking function 203 automatically provides the similar user information to each of the terminals 2 of the users at predetermined timing on the basis of the check information 57 or the similar user information 58*b* in the output information 58. The user is allowed to browse the similar user information on the screen of the terminal 2. The predetermined timing is a time when to access to a predetermined screen, a set regular point of time, and the like, for example.

For further information, the checking function 203 includes, as functions regarding determination of similar users, (3A) user attribute comparison, (3B) health information element comparison, (3C) action information comparison, (3D) graph comparison, and (3E) analysis result comparison.

(3A) A user attribute comparing function compares attribute values of one or more attribute in the user attribute information 51 between the users, determines similarity of the attribute values, calculates the degree of similarity regarding the user attribute, and stores a result in the check information 57.

(3B) A health information element comparing function compares data of one or more element in the health information 53A between the users, determines similarity of the element, calculates the degree of similarity regarding the health information, and stores a result in the check information 57.

The health information element comparing function includes a body temperature comparing function, an examination result comparing function, a symptom comparing function, and the like.

(3C) An action information comparing function compares data of one or more element in the action information 53B between the users, determines similarity of the element, calculates the degree of similarity regarding the action information, and stores a result in the check information 57. The action information comparing function includes a text mining function. In a case where text data such as notes are compared between the users, the action information comparing function checks the text data by using the text mining function, analyzes and compares words extracted from a text, thereby calculating the degree of similarity regarding the content of the text.

(3D) A graph comparing function compares graphs of one or more corresponding element (containing an item such as an attribute) in the graph data 54 between the users, determines similarity of the element, calculates the degree of similarity regarding the graphs, and stores a result in the check information 57. The graph comparing function compares graph patterns between a graph of data on the element of the user and a graph of data on the corresponding element of other user, for example, and calculates the degree of similarity regarding the graphs of the element.

(3E) An analysis result comparing function compares analysis results or messages between the users by using the analysis information 56, which is the analysis result by the analyzing function 202, and the message information 58*a* of the output information 58, calculates the degree of similarity regarding the analysis results or the messages, and stores a result in the check information 57. The item of a comparison target is a numerical value of a predetermined item in the result of the tendency analysis for each element and a state of tendency thereof, information on the action that is the result of the action extraction, information on a possibility of a disease of a disease risk determination result, information on a state related to pregnancy that is the result of the pregnancy support, and the like.

The checking function 203 may determine a similar user by means of a single function of the above functions, or may comprehensively determine the similar user by using a combination of the plurality of functions. As an example of the latter, the checking function 203 uses the degree of similarity of the user attribute, the degree of similarity of the health information, the degree of similarity of the action information, the degree of similarity of the graphs, and the degree of similarity of the analysis results, and calculates the degree of comprehensive similarity between the users by means of predetermined total calculation including addition, multiplication and the like thereof.

(4) The searching function 204 is realized by using the searching unit 19 and the like, and is a function to search details of the user information (share information) of other user, which contains the similar user information, by means of a condition specified by the user. The present system provides the searching function 204 as a complementing function in addition to the function to automatically provide the similar user information by the checking function 203. The user inputs a condition for searching user information of other user on the screen of the terminal 2 at any time if necessary by using the searching function 204, and carries out searching. A search condition is a desired attribute of the user, a value of the element, a free keyword, or the like. The searching function 204 searches, in accordance with the search condition, the user information of the group of users and the check information 57, which are registered to the DB 50, extracts information of other user that meets the search condition to constitute search result information, and provides the same to the terminal 2 of the user. The user can obtain and browse information of other user who meets the desired condition on the screen of the terminal 2.

(5) The statistical function 205 is realized by using the graph creating unit 14, and is a function to provide statistical information of the group of users including the similar user to the user. The present system provides the statistical function 205 as a complementing function in addition to provision of the similar user information by the checking function 203.

The statistical function 205 carries out statistical processing containing aggregation regarding a predetermined item of the user attribute, the health information, the element of the action information, the analysis result, and the like, which are regarding the group of users including the similar user, configures statistical data on a result, and stores the statistical data in the DB 50. The statistical function 205 aggregates the data of the group of users with respect to a specific user attribute, for example, finds a statistical value such as an average and a dispersion, and configures the statistical data containing graphs thereof and the like by using the graph creating unit 14. The statistical function 205 uses the statistical data to provide a screen including the graphs and the like of the statistical information to the terminal 2 of each of the users in addition to the similar user information. The user can browse the statistical information regarding the desired item on the screen.

(6) The auxiliary function 206 is realized by using the auxiliary unit 70, and includes an input auxiliary function, a reference graph function, a related information searching function, and the like. The input auxiliary function is a function to assist the user to input data, and includes a medical apparatus cooperating function and a voice input function. The medical apparatus cooperating function is a function to input data while cooperating with the medical apparatus 3 and the terminal 4. The voice input function is a function to input data through voice of the user. The reference graph function includes a function to cause the terminal 2 of the user to display a reference graph regarding the element or the like in the health information to compare a graph of the user with the reference graph. The related information searching function automatically searches an attribute, a health state and an analysis result of each user and related information related to the similar user information from the Internet, and provides them to the terminal 2 of the user.

The present system provides the searching function 204, the statistical function 205, and the auxiliary function 206 in accordance with a type of the service to be provided to the user.

[Data Input]

A specific example when data are inputted and registered in the system of FIG. 1 is shown below. Input of body temperature and menstruation data is first carried out as follows. The user measures a basal body temperature by means of the medical apparatus 3 such as a thermometer every day. The user inputs the basal body temperature on a screen of the application 20 of the terminal 2, and inputs information on a menstruation date and the like in a case where the user undergoes menstruation. The user may manually input a numerical value of a basal body temperature table of paper on the screen of the application 20, or may convert the numerical value into data by means of scanning or photographing of the paper to input it. In a case of manually inputting it, an input field for the body temperature is displayed on the screen of the application 20, whereby the user can select and input the date and the numerical value. Further, a graph field for the body temperature is displayed on the screen of the application 20, whereby the user can input it by plotting the numerical value at a date portion.

Further, the user may input the body temperature data and the like with communication from the medical apparatus 3 through the body temperature-menstruation data inputting unit 21 of the terminal 2. The medical apparatus cooperating function of the input auxiliary function is realized by the application 20 of the terminal 2 and the auxiliary unit 70 of the service unit 10. For example, the user holds or connects the medical apparatus 3, which is the thermometer, to an interface unit by the body temperature-menstruation data inputting unit 21 of the terminal 2, whereby the body temperature data are transferred and inputted to the medical apparatus 3. The application 20 of the terminal 2 saves the inputted data such as the body temperature and the menstruation in the terminal 2, and transmits them to the server 1 so as to cause the server 1 to register them.

The input data such as the body temperature are appropriately converted into data in a predetermined form that the present system can deal with by the application 20 and the service unit 10. Further, in a case where the medical apparatus 3 holds the body temperature data in time series or with graphs, or in a case where the medical apparatus 3 holds information such as menstruation, body height, body weight, and BMI (physique index), the other measured data, the health information, the action information, and the like in addition to the body temperature together, these data may be inputted into the application 20 of the terminal 2 as a whole. Various kinds of the health information and the action information may be inputted to the medical apparatus 3. The measured data of the other measurement items may be inputted and registered in the similar manner.

Next, an input of examination result data is carried out as follows. It will be explained together with a usage example of medical institutions and examination institutions thus assumed. For example, a user who undergoes treatment and examination of infertility goes to the department of obstetrics and gynecology or the like at a hospital. A doctor examines the user who is a patient, orders an examination and a prescription, diagnoses the medical condition, and carries out treatment such as medical activities as necessary. The treatment includes a timing method, treatment of diseases causing infertility, artificial insemination, and the like.

An examiner, who belongs to an examination company that is an examination institution and received an order of the examination, an examination department in the hospital, or the like, conducts the ordered examination. The examination institution measures, as a blood test, values of female hormones and the like contained in the blood of the user, which is the specimen, by using an examination device, for example, and records examination result data of the user in the terminal 4 and the like.

The user inputs the examination result data into the terminal 2 by using a paper of examination results or the examination result data provided from the examination institution or the like. The application 20 of the terminal 2 displays a screen including an input field for the examination result data, whereby the user can input, through the screen, a date of the examination, the medical institution or the examination institution thus used, examination items, the values thereof, and the like. Further, in particular, the user can collectively input the examination result data transferred from the examination result data outputting function of the terminal 4 into the terminal 2 of the user. The terminal 2 saves the examination result data inputted through the examination result data inputting unit 22 in the terminal 2, and transmits and registers them to the server 1.

In this regard, among the user, the medical institution or the examination institution, and the company, data and information of the user may be provided on the basis of mutual consent from the terminal 4 to the terminal 2 of the user or the server 1. The subject to be provided is information on medical record of the medical institution, the measured data, the examination result data by the examination institution, and the like. In this case, it is possible to reduce time and effort of the user to register the data. Further, the paper or data on the examination results may be transmitted from the user or the examination institution to the company by mail or via the communication network 9, and a person in the company may convert the paper or the data into digital data as the examination result data. Further, in a case of an examination that the user performs using test drug or the like by himself or herself, the values measured by the user may be inputted into the terminal 2 and be registered as the examination result data.

The case where the voice input function is used is as follows. As an element that configures the voice input function, the terminal 2, the application 20 or the service unit 10 is provided with a known voice recognizing function. When the user inputs data such as a body temperature with the application 20 of the terminal 2, the user selects usage of the voice input function, and inputs a value of the body temperature with his or her voice, for example. For example, the voice recognizing function of the application 20 recognizes and converts the voice inputted from the user into voice data, checks the voice data, and extracts information such as the value of the body temperature or the like. The application 20 transmits the voice data or the extracted information to the server 1, and the server 1 registers body temperature data from the voice data or the extracted information. The same applies to the case where the server 1 carries out the analysis.

[Processing (1)]

FIG. 3 first shows, as main processing by the application 20 and the server 1, a flow regarding data processing that contains registration of health information and the like of each individual user and analysis of his or her health state. Reference numeral S1 and the like indicate processing steps.

(S1) In the server 1, the medical examination information 52 and the processing defining information 59, which are management information of the present system, are set in advance by the manager and the medical information setting unit 12. The content of settings is updated at any time in accordance with addition, revision or the like of information on medical care and examinations.

(S2) On the basis of an operation of the user, the application 20 of the terminal 2 accesses the service unit 10 of the server 1 when usage of the service is started or at any time, and a screen for registration of attribute information of the user and the like is provided to the terminal 2 as a screen of the service. The present screen includes an input field for an item of each attribute of the user, which corresponds to the user attribute information 51 in FIG. 5A (will be described later), by which information such as choices and texts, that is, attribute values can be registered for each of the items. The user setting unit 11 registers information inputted through the present screen to the user attribute information 51. In a case where the user underwent treatment or the like, the user can appropriately set confirm, or update the content of the user attribute information 51 for himself or herself through the present screen, for example.

(S3) At any time, the application 20 of the terminal 2 of the user accesses the service unit 10 of the server 1, and provides the screen screen including the input field for the body temperature and menstruation data by means of the health information managing unit 13A. The user inputs information on his or her body temperature and menstruation through the present screen on the basis of the body temperature data transferred from the medical apparatus 3, for example. The application 20 of the terminal 2 transmits the body temperature and menstruation data of the user to the server 1, and the health information managing unit 13A registers them as part of the health information 53A. Measured data of other measured items can similarly be registered.

(S4) Similarly, at any time, the terminal 2 of the user accesses the server 1, and a screen including an input field for examination result data is provided by the health information managing unit 13A. The user inputs his or her examination result data through the present screen on the basis of the examination result data transferred from the terminal 4, for example. The application 20 of the terminal 2 transmits information on the examination result data and units thereof of the user to the server 1, and the health information managing unit 13A registers them as part of the health information 53A.

(S5) At any time, the application 20 of the terminal 2 of the user accesses the service unit 10 of the server 1, and a screen including a calendar is provided by the calendar inputting unit 15. The user can input, into dates of the calendar, information on a body temperature, menstruation, an examination result, a symptom, medication, an action, a note, treatment (hospital visit), or various kinds of other elements of the user. The input can be carried out by text input, selection of a choice or a mark, or the like. The calendar inputting unit 15 registers user input information to the calendar input information 55. As described above at Steps S3 to S5, the user can input and register the health information and the like on a screen of the terminal 2 of the user at any time on a daily basis. Further, the user can confirm or revise the registered information. In this regard, the health information managing unit 13A registers the data corresponding to the health information in the calendar input information to the health information 53A, and the action information managing unit 13B registers the data corresponding to the action information in the calendar input information to the action information 53B.

(S6) The graph creating unit 14 of the server 1 creates or updates the body temperature-menstruation graph of each user (FIG. 10, which will be described later) by using the body temperature and menstruation data of the health information 53A at Step S3, and saves it as a part of the graph data 54. The body temperature-menstruation graph is a graph based on time series values of the basal body temperature, and is a graph in which information such as a menstruation date and a menstrual cycle is superimposed. The graph creating unit 14 provides a screen including the created body temperature-menstruation graph to the terminal 2 of the user.

Further, the graph creating unit 14 creates or updates an examination result graph of each user (FIG. 11 and the like, which will be described later) by using the examination result data in the health information 53A at Step S4, and saves it as part of the graph data 54. The examination result graph is a graph of time series values regarding a plurality of types of examination items, for example, a plurality of types of female hormones by a blood examination. The graph creating unit 14 provides a screen including the created examination result graph to the terminal 2 of the user.

Similarly, the graph creating unit 14 creates a graph of each of items of the attribute information and elements of the action information in the user information registered by the user, and stores them in the graph data 54.

(S7) The analyzing unit 16 of the server 1 carries out tendency analysis processing of the health state of each user on the basis of the user attribute information 51, the medical examination information 52, the processing defining information 59, and the like by using the data of each of the elements of the user, which were registered at Steps S3 to S6 described above, and stores a result thereof in the analysis information 56. The tendency analysis contains tendency analysis of the body temperature and the menstruation, tendency analysis of the examination result, and tendency analysis of the symptom obtained by using the health information 53A, tendency analysis of the action obtained by using the action information 53B, and the like.

The analyzing unit 16 compares, as the tendency analysis, a numerical value of data such as a graph of the user with a number range or a reference graph of the reference information based on the medical examination information 52 and the processing defining information 59, and determines and detects a state of good or bad by the absolute value and tendency of variation in relative values in time series, for example, a state of improvement, deterioration, maintenance and the like. Further, the analyzing unit 16 calculates and records a difference in temperature and a numerical value of a predetermined item such as a menstrual cycle (will be described later), calculates an amount of change of the numerical value of the item in time series, compares the calculated numerical value with a numerical value of the reference information, and determines the state of the tendency of the user.

(S8) The analyzing unit 16 carries out action extraction of each user and action tendency analysis by using the action information and the health information registered as described above, and stores results thereof in the analysis information 56. The analyzing unit 16 refers to and extracts a past action of the user, which is estimated to be related to or influence on the health state that includes current tendency of the user detected by the tendency analysis at Step S7, in the action extraction processing. The analyzing unit 16 determines the above action to be extracted from time series action data on the basis of the processing defining information 59 by using the user attribute information 51 of the user, the analysis information 56 regarding each of the elements, and the like. The analyzing unit 16 saves the extracted action as part of the analysis information 56. Similarly, the analyzing unit 16 carries out processing to extract a symptom at Step S8.

Processing for action extraction is peculiar processing in which a past action and the like that are likely to relate to a current health state of the user are estimated gently, and in which extracted information is accumulated in the DB 50 and it is provided to the user as reference information. The user can view information on the past action and symptom that are likely to relate to his or her current health state on the screen, and consult his or her actions or the like in the future.

The analyzing unit 16 determines tendency of actions of the user for the past period in tendency analysis processing for the actions. For example, the analyzing unit 16 calculates an amount, frequency, continuity and the like of each action type such as diet and exercise in values, and determines time series changes thereof. The analyzing unit 16 calculates the amount of various kinds of actions with the number of registered days, for example. Similarly, the analyzing unit 16 determines tendency of symptoms of the user for the past period in tendency analysis processing for the symptoms.

The analyzing unit 16 extracts an action, which is estimated to be useful to improve the health state of the user, from the action information of the user. Further, the analyzing unit 16 generates an action that is estimated to be useful to improve the health state of the user on the basis of the processing defining information 59. The analyzing unit 16 generates action support information containing the action, and stores it in the analysis information 56.

(S9) The analyzing unit 16 carries out comprehensive disease risk determination processing by using a combination of the user attribute information 51 and various kinds of elements in the health information containing the symptom data described above, and stores a result thereof in the analysis information 56. In the disease risk determination processing, the analyzing unit 16 compares the value of the element containing the symptom with a reference numerical value on the basis of the processing defining information 59 by using result information of symptom extraction and the tendency analysis of the symptoms, and gently estimates a possibility of each of the various kinds of diseases peculiar to females and the like.

(S10) The analyzing unit 16 analyzes a state of the user concerned with pregnancy or fertility by using the user attribute information 51, the elements in the health information 53A, the elements in the action information 53B, and the analysis information 56 of the user as described above, and calculates an index value indicating a state of ease of pregnancy and the like and an index value regarding a pregnancy activity with a partner, for example. The analyzing unit 16 generates pregnancy support information for heightening a possibility of pregnancy of the user in accordance with the state of the user concerned with the pregnancy or fertility, and stores it in the analysis information 56. The pregnancy support information contains a message of advice and the like for the pregnancy activity with the partner according to the state of the user concerned with the pregnancy, for example.

(S11) The analyzing unit 16 determines an output message according to the health state of each user on the basis of the analysis information 56 containing the results of S7 to S10 described above, and stores it in the message information 58a of the output information 58. The outputting unit 18 displays the message in a dedicated field of the screen of the terminal 2 of the user or a field in a graph or the like on the basis of the output information 58. The outputting unit 18 stores history information of the outputted message in the output information 58. Timing to output the message may be a point of time when the user accesses a predetermined screen, a point of time when a request of the user is received, a point of time when data of the user are analyzed, a point of regular time based on user setting, and the like.

The user can browse information such as his or her health information thus registered, the action information, the messages of the analysis result on the screen of the terminal 2 of the user at any time. The user can browse the selected individual information on the screen, browse a list of a plurality of types of information and the information in parallel, browse information on a daily basis, and browse information for a specified past period.

The graph creating unit 14 creates a graph for each item of the analysis results in the analysis information 56 of the user, and stores them in the graph data 54.

(S12) The server 1 reads out corresponding data saved in the DB 50 in response to a request by the user to output desired data from the application 20 of the terminal 2 of the user, and transmits them to the terminal 2. In the DB 50, the data of each user are organized and accumulated. The application 20 of the terminal 2 of the user saves the data received from the server 1 in a memory, and carries out displaying or printing of a screen. The data that can be outputted contain the user attribute information 51, the health information containing the graphs and the calendar input information 55, the action information, the messages of the analysis result, and the similar user information. As the outputted data, for example, a file of history information for the specified past period and list information is available. Further, when the examination result data are outputted at Step S12, the server 1 carries out unit conversion of the values of the examination items, and provides data after the unit conversion.

[Processing (2)]

Figure 4:
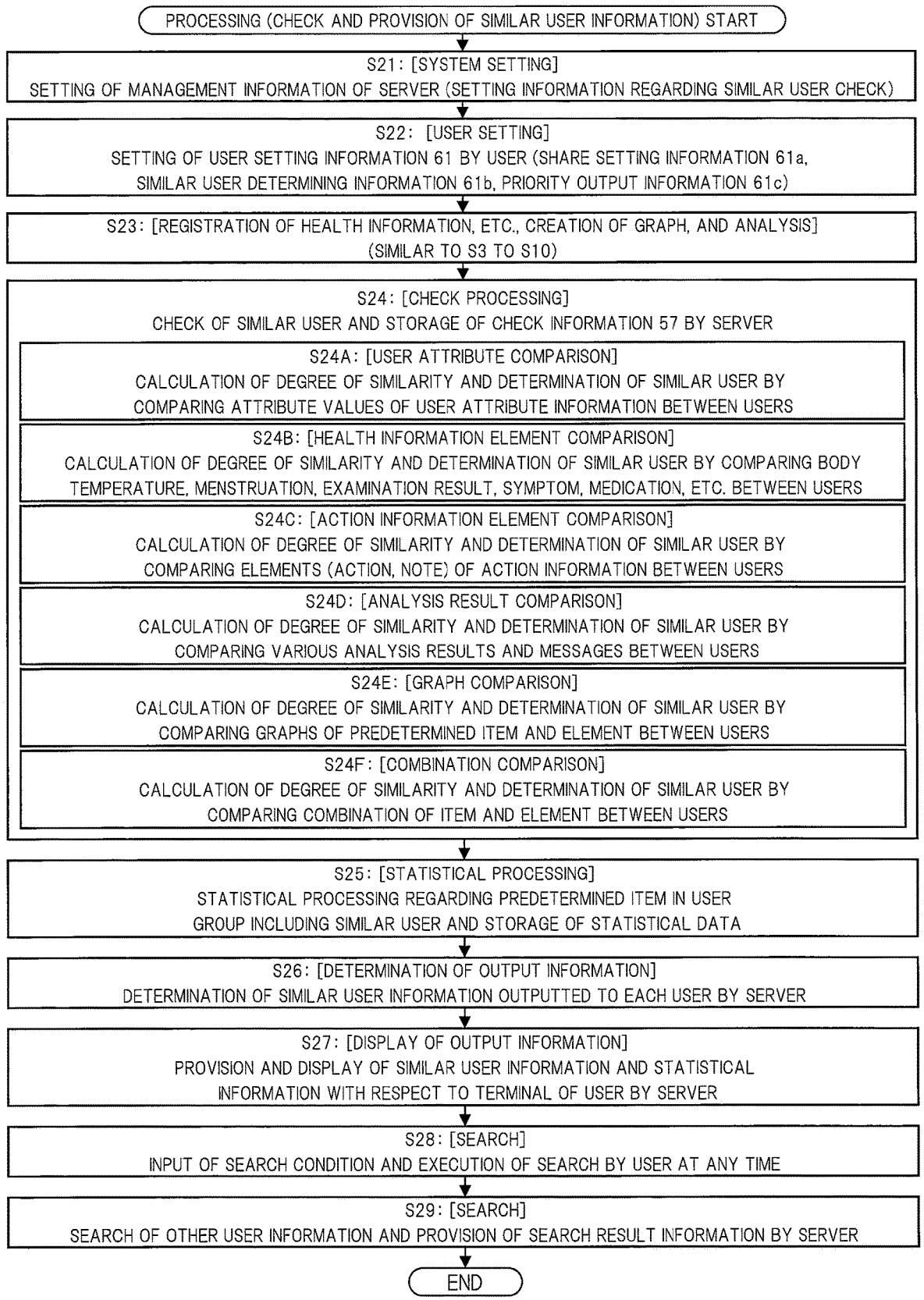
FIG. 4 is a view showing a processing flow of a check of a similar user and provision of similar user information among the major processing of the health care system.

FIG. 4 shows, as the main processing by the application 20 and the server 1, a flow regarding processing that contains check of a similar user by the checking unit 17 and the checking function 203 and provision of the similar user information. Step S21 and the like indicate processing steps.

(S21) In the server 1, the user setting information 61 regarding check of the similar user and provision of the similar user information, which is management information of the present system, is set in advance by the manager. The user setting information 61 (FIG. 6, which will be described later) corresponds to setting information for the service, and is similarly applied to all users who utilize it for each type of service.

(S22) On the basis of an operation of the user, the application 20 of the terminal 2 accesses the service unit 10 of the server 1, and a screen for user setting of each user is provided to the terminal 2. The present screen includes an input field for setting the content of the user setting information 61 himself or herself by the user (FIG. 7 and the like, which will be described later). The user setting unit 11 stores input information on the present screen in the user setting information 61. The user can set the content of the share setting information 61a, the similar user determining information 61b, and the priority output information 61C. Items of a share target are set to the share setting information 61a. Items for determination of the similar user are set to the similar user determining information 61b. Items of a priority output target are set to the priority output information 61C. Each of the items can be selected on the basis of a unit such as a user attribute, a health information element, an action information element, an analysis type.

(S23) Step S23 is similar to Steps S3 to S10 described above, at which various kinds of analysis and the like including registration of the health information and the like for the group of users and creation of a graph are carried out. Thus, data and information that become targets of the check are accumulated in the DB 50 of the present system.

(S24) At Step S24, the checking unit 17 of the server 1 carries out the check processing regarding the similar user with respect to data and information of the group of users in the DB 50 at Step S23, and stores its result information in the check information 57. The checking unit 17 carries out the check processing, for example, on a periodic basis or at timing according to a point of time when data registration by the user occurs or the like, and updates the content of the check information 57. Processing at Step S24 contains each process of the processing at Steps S24A to S24F. Each of the processing is carried out in accordance with the user setting information 61 of each user.

(S24A) Step S24A is similar user check processing based on user attribute comparison. At processing of the user attribute comparison at Step S24A, similarity between the users is checked by comparing attribute values of each attribute, which is a share target item of the user attribute information 51, between two users in the group of users. The checking unit 17 calculates, in the check, the degree of similarity regarding the user attribute between the users, and determines a similar user. The checking unit 17 then stores information in which the user and other user who are similar users on the basis of the degree of similarity are associated with each other in the check information 57.

(S24B) Step S24B is similar user check processing based on health information element comparison. At the processing at Step S24B, similarity between the users is checked by comparing data of an element corresponding to body temperature menstruation data, examination result data, symptom data, medication data or the like, which corresponds to the share target element, between the users in the group of users. The checking unit 17 calculates, in the check, the degree of similarity regarding the element between the users, determines a similar user, and stores it in the check information 57.

In a case of comparison of symptoms, the checking unit 17 compares symptoms of a pair of users as comparison targets, which are registered in a target period. The checking unit 17 obtains or calculates numerical values such as the number of days of registration, an amount to which the degree of symptom is added, frequency, and continuity for each type of symptom such as stomachache and headache in the target period. The checking unit 17 compares the numerical values between the users, and calculates the degree of similarity of the symptom between the users on closeness of the numerical values. Similarly, in a case where medication is compared, the checking unit 17 compares information on the medication registered in the target period between the users, and calculates the degree of similarity of the medication.

(S24C) Step S24C is similar user check processing based on action information element comparison. In processing at Step S24C, similarity between the users is checked by comparing actions or note texts, which are elements of the share target, between the users. The checking unit 17 calculates, in the check, the degree of similarity regarding the action or the note between the users, determines a similar user, and stores it in the check information 57.

In a case where the actions are compared, the checking unit 17 compares the actions registered in the target period or the actions extracted at Step S8 in the pair of users who are the comparison target. The checking unit 17 obtains or calculates an amount such as the number of days of registration and a total time, or numerical values such as frequency and continuity for each type of action such as exercise and diet in the target period. The checking unit 17 compares the numerical values between the users, and calculates the degree of similarity of the action between the users on the basis of closeness of the numerical values.

In a case where texts of notes are compared, the checking unit 17 checks similarity between the users by comparing text data of the notes registered in the calendar, which are elements of the share target, between the users. The checking unit 17 compares the text data of the notes registered in the target period with respect to the pair of users who are the comparison target. The checking unit 17 checks texts of the respective users using a text mining function, extracts words contained in each of the texts, calculates the number of days, the number of appearance or frequency of registration for each of the extracted words. As the text mining function, a known technique can be utilized. The checking unit 17 compares the calculated numerical values between the users, and calculates the degree of similarity in the content of the text of the note between the users on the basis of closeness of the numerical values.

The checking unit 17 may extract only a specific word from the text, and calculate the number of days, the number of appearance, or the like of registration of the specific word. The specific word is information set by the present system, for example. For example, a word "My stomach hurts" is associated with a health state in which there is a symptom of stomachache. By using the specific word, similarity regarding an element of the user attribute, the health information or the action information can be determined.

(S24D) Step S24D is similar user check processing based on analysis result comparison. In processing to compare the analysis results at Step S24D, similarity between the users is checked by comparing various kinds of analysis results or messages, which is an item of the share target, between the users. The checking unit 17 calculates, in the check, the degree of similarity regarding the analysis result or the message between the users, determines a similar user, and stores it in the check information 57. The checking unit 17 compares values of the analysis results or messages stored in the analysis information 56 or the message information 58a in the pair of users who are the comparison target. The checking unit 17 calculates the degree of similarity regarding the analysis result or the message between the users on the basis of closeness of the values.

The checking unit 17 may calculate the degree of similarity of a tendency analysis result. For example, the checking unit 17 refers to and compares values respectively indicating states of tendency in a result of the tendency analysis for the same element between the users. The state of the tendency is a value of a determination result including a state of good or bad of a numerical value in a predetermined item such as a difference in temperature and a menstrual cycle or a state of relative improvement or deterioration, for example. The checking unit 17 compares the states of tendency of the two, and determines closeness of the states of the tendency. In a case where the values of the two are the same or a difference thereof is small, or in a case where they are values belonging to the same group, the checking unit 17 can determine that similarity is high. The same group is information set by the present system.

Similarly, the checking unit 17 can calculate the degree of similarity of each unit with respect to analysis results of various kinds of analysis such as action extraction, disease risk warning, and pregnancy support. For example, in a case where the same or similar action is extracted on the basis of a result of the action extraction, the degree of similarity of the action between the users is high. In a case where a possibility of the same or similar disease is estimated on the basis of a result of the disease risk warning, the degree of similarity regarding the disease is high. In a case where index values of the states concerned with pregnancy are the same or closer on the basis of a result of the pregnancy support processing, the degree of similarity regarding pregnancy is high.

The checking unit 17 may calculate the degree of similarity of the output message. The checking unit 17 refers to the message information 58a of the output information 58, and compares types of the output messages, the number of times of output, texts in the messages or the like in the pair of users who are the comparison target. In a case where the values of the two are the same or a difference thereof is small, or in a case where they are values belonging to the same group, the degree of similarity of the message is high.

(S24E) Step S24E is similar user check processing based on graph comparison. The checking unit 17 uses the graphs of the predetermined item or the element created at Step S6. The checking unit 17 checks similarity between the users by comparing graph patterns of the graphs corresponding to the predetermined item or the element, which is the share target, between the users. The checking unit 17 calculates, in the check, the degree of similarity regarding the graph between the users, determines a similar user, and stores it in the check information 57.

(S24F) Moreover, at Step S24F, the checking unit 17 may comprehensively calculate the degree of similarity between the users by using the results of the degrees of similarity of all of the attribute in the user attribute information 51, the element in the health information 53A, the element in the action information 53B, the graph, and the analysis result described above as the comparison targets. The checking unit 17 calculates the degree of similarity between the users by comparing a predetermined combination of the user information containing the attribute item of the user attribute information, the elements of the health information and the action information, the graph, and the analysis result between the users. For example, the checking unit 17 calculates the degree of similarity for each of the elements and the items that constitute the combination, and obtains the degree of comprehensive similarity between the users by means of predetermined total calculation including addition, multiplication, and the like by using these degrees of similarity. The combination to calculate the degree of similarity can be set in advance in accordance with the management information of the present system and the user setting information 61. An example of the combination to calculate the degree of similarity is as follows.

(1) Combination of at least two of the attribute information, the health information and the action information. The checking unit 17 calculates, on the basis of the settings, the degree of similarity in accordance with a combination of one or more attribute in the attribute information and one or more element in the health information and the action information, for example. For example, the checking unit 17 calculates a degree of first similarity regarding the attribute and a degree of second similarity regarding the elements of the health information and the action information, and calculates the degree of comprehensive similarity by using these degrees of similarity.

As a specific example of the combination described above, the checking unit 17 compares attribute values of an attribute containing at least one of age, treatment, or anamnesis in the attribute information between the users to calculate the degree of first similarity, compares data of at least one element of an examination result, a symptom, or medication in the health information to calculate the degree of second similarity, and calculates the degree of similarity of combination by using the degree of first similarity and the degree of second similarity.

(2) Combination of a graph and at least one of the attribute information, the health information, or the action information. The checking unit 17 calculates, on the basis of the settings, the degree of similarity on the basis of combination of one or more attribute, one or more element in the health information and the action information, and one or more graph regarding a predetermined item or an element, for example.

(3) Combination of an analysis result and at least one of the attribute information, the health information, or the action information. The checking unit 17 calculates, on the basis of the settings, the degree of similarity on the basis of combination of one or more attribute, one or more element of the health information and the action information, and the analysis result or the output message, for example.

(4) Combination of at least one of the attribute information, the health information or the action information, and user information of a partner (will be described later). The data managing function 201 manages the user information of the user and the user information of the partner of the user. The checking unit 17 compares the user information between the partners of the users, and calculates the degree of similarity between the partners by checking similarity of the user information. The checking unit 17 calculates, on the basis of the settings, the degree of comprehensive similarity on the basis of combination of the degree of similarity regarding one or more item or element of the attribute information, the health information and the action information, and the degree of similarity between the partners.

(5) Combination of a pair of the user and his or her partner. The data managing function 201 manages, as users, user information of a first user and user information of a second user who is a partner of the first user. The checking unit 17 compares the user information between the first users, calculates the degree of first similarity between the first users, compares the user information between the second users, and calculates the degree of second similarity between the second users. The user information compared between the first users contains at least one of the attribute information, the health information or the action information, and the user information compared between the second users contains at least one of the attribute information, the health information or the action information. However, the two may be different from each other. The checking unit 17 calculates the degree of similarity of the pair of the first user and the second user by using the degree of first similarity and the degree of second similarity.

(S25) At Step S25, the statistical function 205 of the server 1 carries out the statistical processing that contains aggregation regarding a predetermined item for all users in the group of users registered in the present system or a plurality of users who are respectively similar users of some users. The statistical function 205 organizes statistical data containing the graphs of the result of the statistical processing, and stores them in the DB 50. The users or items that are targets of the statistical processing may be fixed setting information by the present system, or may be one set or specified for each user.

(S26) At Step S26, the server 1 determines the content of the similar user information for being outputted to each of the users on the basis of the check information 57 that is the result at Step S24, and stores the determined information in the output information 58 as the similar user information 58*b*, for example. The information is information for defining when information of which item of which similar user is outputted to which user.

As a first method, determination of the content of the similar user information to be outputted to each of the user described above may be made in advance at a point of time to check it by the server 1, or may be made, as a second method, at a point of time to output it to the individual user. In a processing example of the first method, the certain content of the similar user information, for example, an item such as a specific similar user, and a predetermined attribute or element is determined at a point of time of the check. Then, the similar user information is provided as it is at timing when to access the screen by the individual user or the like.

In a processing example of the second method, the content of the similar user information, for example, the item or the range such as a similar user, an attribute and an element, which are candidates of the output is schematically determined at a point of time of the check. Then, information to be outputted is determined among the candidates described above on the basis of a similarity order and/or the settings of the priority output information 61C at timing to access the screen by the individual user or the like, for example, and is provided. Further, it may be a method of selecting information to be outputted among the candidates at random.

In a case where the priority output information 61C for each user is set, the server 1 determines information to be outputted on the basis of the content of the priority output information 61C when to determine the similar user information to be outputted described above, or when to output the similar user information to the individual user. In a case where an essential item is specified in the priority output information 61C of the user, the server 1 surely outputs the information on the item to the screen of the terminal 2 of the user. In a case where a preferential item is specified in the priority output information 61C of the user, the server 1 outputs information on the item on the screen of the terminal 2 of the user in preference to the other items.

(S27) At Step S27, the outputting unit 18 of the server 1 transmits information containing the similar user information to the terminal 2 of the user at predetermined timing on the basis of the similar user information 58*b* of the output information 58 at Step S26, and causes the terminal 2 to display it on the screen. The outputting unit 18 then stores history information of the similar user information thus outputted in the output information 58. For example, the present system automatically causes the terminal 2 to display the similar user information in a predetermined region within the screen when the user browses a predetermined screen. In another method, a request for the similar user information is transmitted from the terminal 2 in response to an operation of the user, and the server 1 transmits the similar user information to the terminal 2 at timing when the request is received, and causes the terminal 2 to display it.

For example, as shown in FIG. 24 (will be described later), a list of a plurality of similar users is displayed on the screen including the similar user information, and in response to selection of a similar user from the list by the user, detailed information of the similar user is displayed. The user can select a similar user or an item that the user wants to view on the screen to browse its information.

Further, the outputting unit 18 transmits information containing the statistical information to the terminal 2 of the user on the basis of the statistical data in the DB 50 at Step S25, and causes the terminal 2 to display it on the screen. The outputting unit 18 causes the terminal 2 to display the statistical information containing the graph and the like when to display a predetermined screen, when to display the similar user information, or at predetermined timing when a request is received from the user or the like. The user can browse the similar user information and the statistical information described above on the screen of the terminal 2.

(S28) Steps S28 and S29 are a searching process by the searching function 204. At Step S28, the user carries out an operation to select usage of search by the application 20 of the terminal 2 when necessary. The user inputs a search condition for searching information of other user in a field of the displayed screen for search, and carries out the search. Further, in this search, whether a target is all users or a specific similar user can be specified by the user. The application 20 of the terminal 2 transmits the request including the search condition to the server 1.

(S29) At Step S29, the searching unit 19 of the server 1 receives the request including the search condition from the terminal 2 of the user, and searches the information of the other user, which is registered in the DB 50, by using the information on the search condition. The searching unit 19 constitutes search result information, and transmits it to the terminal 2 of the user. The terminal 2 receives the information, and displays a screen including the search result information. For example, a list of other users who correspond to the search condition is displayed on the screen including the search result information, and detailed information of each of the other users is displayed in response to a selection operation of the other user by the user.

For example, in a case where there is no desired information in the similar user information that is automatically displayed on the screen of the terminal 2, the user oneself can specify a condition in more detail by the searching function 204 to search detailed information of the other users, and can browse and obtain it.

[User Attribute Information]

FIG. 5A shows a configuration example of main data items in the user attribute information 51. In the user attribute information 51, information on various kinds of attributes concerned with the health state of the user, that is, attribute values are stored in addition to basic information of the user. In the user attribute information 51 in FIG. 5A, there are, as the items, a user ID, a password, a terminal address, a user name, sex, age, the medical institution, a treatment period, treatment, a disease, anamnesis, pregnancy, a partner, a membership type, and the like.

The user ID, the password, the terminal address, and the like are basic information of the user for control the service. The terminal address is an IP address, a telephone number, a mail address or the like. The basic information may contain an address or the like. The "user name" item is anonymous or a nickname set to the user. The "age" item is age or an age group.

The "medical institution" item contains identification information of each of medical institutions and examination institutions such as a hospital that the user utilizes at present time. The "medical institution" contains management of a history of changing hospital and the like, and contains a hospital name, a period to visit the hospital, and the like, for example. A specific example is "present time: hospital A", "January to December, 2012: hospital B, January, 2013 to: hospital A", and the like. In this regard, "hospital A" and the like indicate identification names abstracted for explanation.

The "treatment period" item indicates a period from start of treatment to present time or end thereof, the number of years thereof, and the like. The treatment stated by this item means overall effort, and individual treatment is managed by the following items. The "treatment" item is information indicating a situation of treatment by the medical institution, and a name and identification information are registered therein. The "treatment" includes practice of therapy by the user. The "treatment" includes management of a history of the treatment. The "treatment" includes a state such as progress of treatment, start and end thereof, and management of information on details of the treatment. A specific example is "present time: treatment X=in-vitro fertilization", "2011: timing method, 2012: artificial insemination, 2013: in-vitro fertilization", and the like.

The "disease" item is information concerned with the above "treatment" item and indicating a current main disease or a medical condition of the user, and a name and identification information are registered therein. The "disease" includes management of a history. The "disease" includes a state such as progress of disease, start and end thereof, and management of information on details of the disease. The "disease" includes a state of potential of a disease and management of a state of health. A specific example is "present time: disease X=infertility" and the like.

The "anamnesis" item stores general information such as a chronic disease, anamnesis, a surgical history, and the like related to the user, which is other than values of the "disease" and "treatment" items described above. Namely, the "anamnesis" item manages information on a secondary illness and treatment. The "anamnesis" includes a disease and treatment in other clinical diagnosis and treatment departments in addition to the obstetrics and gynecology department. A specific example is "2009: disease Y, 2009: treatment Y" and the like. In this regard, the "anamnesis" item may be integrated into the "disease" item or the like.

The "treatment", "disease", and "anamnesis" items can be registered by selection from choices of treatment and diseases set in advance to the present system in addition to registration with text input by the user. Information on names of treatment and diseases, which contains ones that have not been made unification, is set as the management information to the DB 50 of the present system.

The "pregnancy" item stores information regarding a situation of pregnancy or childbirth of the user. Information on the "pregnancy" is success or failure of pregnancy, the number of times thereof, a period of time thereof, age, for example. A specific example is "pregnancy: 0 times", "pregnancy: once: February, 2011 (37 years old)" and the like.

The "partner" item stores information representing a situation of a partner such as a husband and a lover of the user. Information on the "partner" may be configured to store the attribute information such as age, diseases, treatment, and others, for example, or may be configured to store the user ID and the like and refer to another table. The server 1 identifies and associates data of respective users who are partners or a pair of male and female by means of the information on "partner". A specific example is "husband: 38 years old: disease Z" and the like.

The present system may provide different service and functions in accordance with a state of each user such as a membership type and the like. The server 1 manages information in which the user ID or the like, a membership type, service or a function are associated with each other, for example. As the "membership type" item, information on membership types of the users are registered. The membership type is associated with a range of use of the service and the function. As the membership type, there are (a) to (d) described below, for example. A type (a) is a membership type to use related service and function, which contains management of a body temperature, menstruation, and a timing method. A type (b) contains, in addition to those in the type (a), management of the artificial insemination. A type (c) contains, in addition to those in the type (b), management of in-vitro fertilization and microinsemination. A type (d) further indicates that a male spouse is utilized.

The user attribute information 51 provides, as the items of the other attributes, body height, body weight, alcohol drinking, smoking, insurance, a family, a job, an area, an amount of money for treatment, an amount of limit money, limit age, and the like. The amount of limit money is an upper limit of an amount of money spent for treatment, and the limit age is an upper limit of age for continuing the treatment. In the user attribute information 51, items of a predetermined attribute may be an essential input, and the other items may be an optional input. The user may input information given from the medical institution or the like into the user attribute information 51, or may input information by determination of the user himself or herself.

Moreover, the user attribute information 51 in FIG. 5A has share attribute setting items shown in a column 501 as a configuration example of the share setting information 61a. A flag value is set to each of the share attribute setting items 501 for each attribute by share with other user, that is, disclosure or not. A circle mark o (1) indicates "share", and a cross mark x (0) indicates "not share". In the setting of basic service according to the present system, all attributes are set to "share". In the setting of another service, either "share" or "not share" is set to each attribute. In the user attribute information 51, items for setting an attribute for determining a similar user or an attribute of a priority output may be provided similarly.

[Health Information]

FIG. 5B and FIG. 5C show a configuration example of the health information 53A that can be applied to the present embodiment. All items in the health information 53A of FIG. 5B and FIG. 5C can be set as a share target. This table of the health information 53A has "classification", an "item", "description", and a "specific example" as respective columns. The "classification" indicates schematic classification in the health information, and includes (a) body temperature, (b) menstruation, (c) examination result, (d) symptom, (e) medication, (f) others as described above. FIG. 5B shows a portion exclusive of (c) examination result, and FIG. 5C shows a portion of (c) examination result. The "items" are items of the health information, the "description" indicates information and the like that can be registered as explanation of the items, and the "specific example" indicates a specific example of the registered information.

In FIG. 5B, a table of the health information 53A includes, as the "items", a basal body temperature, menstruation, a symptom, medication, a self measurement item, and the like. The "basal body temperature" item contains a temperature measuring date, a body temperature, and the like. A specific example thereof is "Mar. 3, 2014, 36.5° C.". The basal body temperature is one example of the measurement item and measured data. The "menstruation" item contains a start date of this time, an end date of this time, a start date of previous time, an end date of previous time, a menstrual cycle, an estimated ovulation date, and the like. A specific example thereof is, as values of order of the information, "Apr. 1, 2014 to April 5, Mar. 3, 2014 to March 7, 28 days, Apr. 5, 2014".

The "symptom" item contains a symptom regarding a physical condition and the like. A specific example thereof is "a headache, a feeling of fatigue, stress". The "medication" item contains a name of medicine, a start date of taking medicine, an end date of taking medicine, side effects, stop or not of taking medicine, symptom of side effects and the like. A specific example thereof is "Clomid, Mar. 3, 2014 to March 7, presence of side effects, presence of stop of taking medicine, a stomachache".

As the "self measurement item" item, in a case where there is a predetermined measurement item to be measured by the user himself or herself in addition to the body temperature, a measuring date, a measured value and the like are similarly stored for each measurement item as information of a measurement result. As examples of the measurement item, there are a heart rate, a pulse, a blood pressure, breathing, and the like as described above. In this regard, there is a measurement item that can be automatically measured and automatically registered in accordance with the functions of the terminal 2 and the medical apparatus 3.

In FIG. 5C, a table of the health information 53A includes, as the "items", pregnancy support, other medical institution examination item, a self measuring item (self examination item), and the like. As shown in parentheses, the "pregnancy support" includes, as a plurality of more detailed items, a male common examination item, a female common examination item, a timing method, artificial insemination, in-vitro fertilization: egg collection, in-vitro fertilization: transplant, in-vitro fertilization: pregnancy, and the like.

In the "pregnancy support" item, the "male common examination item" contains a sperm collection date, a semen volume, a total sperm number, sperm density, forward motility, high-speed straight motility, a survival rate, a normal morphology rate, and the like. A specific example thereof is, as values in order of the examination items, "Mar. 3, 2014, 2 ml, 40×10^6/ml, 20×10^6/ml, 50%, 25%, 50%, and 50%". The "female common examination item" contains an examination date, LH, FSH, E2, P4, AMH, a size of follicle, an endometrial thickness, and the like. A specific example thereof is, as values in order of the examination items, "Mar. 3, 2014, 2.2 mIU/mL, 6 mIU/mL, 80 pg/mL, 6.5 ng/m, 11 pM, 20 mm, and 8 mm".

The "timing method" contains metrorrhagia, ovulation induction, a width of white vaginal discharge, and the like. A specific example thereof is "absence of metrorrhagia, presence of ovulation induction, a width of white vaginal discharge of 7 cm". The "artificial insemination" contains an LH in urine, presence or absence of artificial insemination, and the like. A specific example thereof is "positive, presence of artificial insemination", and the like. The "in-vitro fertilization: egg collection" contains an anesthesia method, a collection date of eggs, an egg collection number, frozen embryo No-grade, and the like. In this regard, with respect to No-grade of frozen embryo, there are a plurality of frozen embryos, and thus, No (number) is applied to each of the frozen embryos and its grade is registered. A specific example thereof is "intravenous anesthesia, Mar. 21, 2014, 5, {No1-A, No2-A, No3-B, No4-B}". The "in-vitro fertilization: transplant" contains a transplant date, transplanted embryo No-grade-size, presence or absence of assisted hatching, a transplant method, and the like. A specific example thereof is "Mar. 22, 2014, No1-A-48 mm, presence, and microinsemination". The "in-vitro fertilization: pregnancy" contains a determination date of pregnancy, positive determination of pregnancy, a confirmation date of fetal sac, confirmation or not of fetal sac, a confirmation date of heart rate, and the like. A specific example thereof is "Mar. 31, 2014, positive, blank, blank, blank".

Although it is not shown in the drawings, the "other medical institution examination items" item includes examination items concerned with various kinds of examinations in the medical institution and the examination institution.

In the "self measuring item (self examination item)" item, in a case where there is an item that is measured and examined by the user in addition to items by the medical institution or the examination institution among the examination results, information on the item is stored. For example, as information of a result obtained by measuring and examining a predetermined item using a commercially available test drug or the medical apparatus 3 and the like of the user by the user, a measuring date, a measured value and the like are stored. As this "self measuring item (self examination item)" in the (c) examination result, there are a heart rate, a pulse, a blood pressure, breathing, and the like as well as the "self measurement item" in the (f) others. For example, values of a blood pressure (high) and a blood pressure (low), a pulse rate, a breathing rate per minute, and the like are stored. A specific example thereof is "110, 60, 70, 20". Further, as this item, an ovulation test result, a pregnancy test result, the amount of secretion, and the like (will be described later) can be stored.

[Action Information]

FIG. 5D similarly shows a configuration example of the action information 53B that can be applied to the present embodiment. All items in the action information 53B of FIG. 5D can be set as a share target. A table of the action information 53B includes, as classification, an action, timing, a note, an automatic measurement item. The "action" includes, as the items, therapy such as exercise therapy, diet therapy. For example, the exercise therapy contains, as information that can be registered, an implementation period of exercise therapy, and exercise therapy. A specific example thereof is "Jan. 10, 2014 to April 30, swimming". The diet therapy contains, as information that can be registered, an implementation period of diet therapy, and diet therapy. A specific example thereof is "Jan. 10, 2014 to April 30, folic acid". The "timing" item includes, as information that can be registered, a sexual intercourse date, presence or absence of sexual intercourse and the like. A specific example thereof is "Mar. 3, 2014, presence". The "note" item stores, as the notes, free texts or character strings containing a comment, a memo, a feeling and the like. A specific example thereof is "feel strong stress".

The "automatic measurement item" is an item concerned with the action, which can be automatically measured and automatically registered. As examples thereof, there are an exercise time and amount, a sleep time and amount, used calories, a travel distance, the number of steps and the like. In accordance with the function included in the terminal 2 or the medical apparatus 3, for example, a health care function included in a wearable terminal, a predetermined measurement item can be automatically measured and automatically registered. Data of the automatic measurement item may be registered as part of the action information 53B in accordance with the user settings.

In this regard, classification or itemization of various kinds of information contained in the user attribute information 51, the health information 53A, the action information 53B and the like described above is merely one example, and other classification or the like can be made. For example, the information thereof may be centrally managed as health data.

[User Setting Information]

In the share setting information 61a of the user setting information 61, with respect to each attribute in the user attribute information 51 of the user, each element in the health information 53A and the action information 53B, and each item of each analysis, whether to share it for the other users or not, that is, whether to disclose it or not is set.

The similar user determining information 61b is setting information regarding which item such as an attribute, an element and analysis is paid attention to determine a similar user of each user when a similar user is determined by the checking function 203. In other words, the similar user determining information 61b is setting information regarding in which point of view the user wants to view information of other user similar to the user.

The priority output information 61C is setting information regarding information of which item such as an attribute, an element and analysis of the similar user is to be outputted essentially or preferentially to each user when to output the similar user information. In other words, the priority output information 61C is setting information regarding information of which item in the information of the similar user who is the other user the user wants to view essentially or preferentially.

FIG. 6 to FIG. 8 show a configuration example of the user setting information 61. FIG. 6 shows a setting example of each type of service by the present system as a first configuration example of the user setting information. The present system may provide a plurality of types of service as service of business and information processing to be provided to the user, and may provide different service to each user in accordance with a state of the user such as a membership.

Service A setting information in FIG. 6 is setting information regarding a first type of service A that is basic service of the present system. A user group A who uses it, for example, all users are associated with the service A. The service A setting information includes a row of a share item corresponding to the share setting information 61a, a row of an item for determination (determining item) corresponding to the similar user determining information 61b, and a row of a priority output item corresponding to the priority output information 61C.

Each row of the share item, the item for determination, and the priority output item includes rows of an attribute, an element, and analysis. A row of the attribute is setting regarding various kinds of attributes of the user attribute information 51. A row of the element is setting regarding various kinds of elements of the health information 53A and the action information 53B. A row of the analysis is setting regarding various kinds of analysis such as the tendency analysis.

In the service A setting information, the share item is all attributes, all elements, and all analysis. The similar user information to be provided to the user is all information set in the share item. The priority output item includes nothing. Namely, in the similar user information to be provided to the user, all information of the share item is outputted with no priority order. In this regard, in the present example, the priority output item sets preferential information. However, the priority output item may set essential information.

The item for determination is specific attributes, for example, a set of four attributes of {sex, age, disease, treatment}, and includes no element and no analysis. In this regard, in a case of service dedicated to females, the sex attribute can be omitted. In the case of this setting, similarity between users is comprehensively determined by comparing values of the four attributes described above when to check it, the degree of similarity corresponding to each attribute is calculated. Further, a priority order of the attributes that is considered when to determine the similar user is an order of {sex, age, disease, treatment} as it is. Namely, the degree of similarity is first calculated so that the degree of similarity becomes higher as a user has the same sex and his or her age near that of the user. In a case where the priority order is changed, it is set to {treatment, disease, . . . } or the like. In this case, the more similar the situation of treatment is, the higher the degree of similarity becomes. Moreover, a weighting value corresponding to the priority order of each attribute may be set.

Similarly, service B setting information shows a setting example of a second type of service B and a user group B. In the service B setting information, each of share items is all, and the priority output item is nothing. Thus, illustration thereof is omitted. An item for determination (determining item) is a set of three elements {body temperature, menstruation, examination result} in the health information 53A. In this case, the degree of similarity between the users is comprehensively calculated by comparing data containing graphs of the three elements when to check it.

In this regard, in the present setting example, the graph associated with each item of the attribute, the element and the analysis is automatically included. However, the item and the graph thereof may be set by separating them from each other. For example, in a case where one element is set as the item for determination, data on the one element (which is not a graph, but registered data), a graph of the one element, or both of them can be set.

Similarly, service C setting information shows a setting example of a third type of service C and a user group C. In the service C setting information, an item for determination (determining item) is tendency analysis in a type of analysis. In this case, the degree of similarity between the users is comprehensively calculated by comparing information containing an analysis result and a message of the tendency analysis processing when to check it.

In another example of the service setting information, as an item for determination (determining item), the attribute is at least one of age, treatment, or anamnesis, and the element is at least one of an examination result, a symptom, or medication. The checking unit 17 calculates the degree of first similarity regarding the attribute of the item for determination, calculates the degree of second similarity regarding the element, and calculates the degree of comprehensive similarity of a combination of the attribute and the element by using the degree of first similarity and the degree of second similarity.

FIG. 7 shows a setting example different for each individual user as a second configuration example of the user setting information 61. The present system allows an individual user to carry out user setting as service of an option according to a state of the user such as a membership, for example. The user can set each item of a share item, an item for determination (determining item), and a priority output item in the user setting information 61 of the user to either a target or a non-target.

User A setting information is setting information for a user A that is set by the user A. In the user A setting information, a share item is all. An item for determination (determining item) includes two attributes of {medical institution, the examination institution} in addition to the four attributes of {sex, age, disease, treatment} the same as the service A. In a case of this setting, the degree of similarity is calculated to be higher as the medical institution or the examination institution thus used is the same.

In a priority output item, a user attribute is nothing, elements in the health information 53A and the action information 53B are {examination result, menstruation}, and analysis is {tendency analysis, disease risk warning}. In this case, as the similar user information to be displayed on the screen of the terminal 2 of the user A, examination result data and menstruation data containing graphs thereof and information of results of the tendency analysis and disease risk warning thereof are preferentially displayed among all items in the share information of the similar user.

The output information described above contains a numerical value and a message of a predetermined item that is calculated and determined as the time of analysis, such as a numerical value of a female hormone of an examination result, its variation amount, a state of its tendency and a possibility of a disease that is estimated from the tendency, for example. The user A can preferentially browse a graph of the examination result and an analysis result of other user whose medical institution and the like are similar to those of the user A. In a case where the amount of the similar user information to be provided to the user is large, information content is reduced by means of setting of the priority output item, whereby the user can view it easily.

In user B setting information, a share item is all. In an item for determination (determining item), elements in the health information 53A and the action information 53B include an element {action} in addition to the three elements of {body temperature, menstruation, examination result} the same as those of the service B. In this case, similarity between the users is comprehensively determined by comparison of data on the four elements. Namely, the degree of similarity becomes higher as the registered action is similar to that of the user.

Further, a priority output item includes two attributes of {pregnancy, partner} and two types of analysis of {action extraction, pregnancy support}. In this case, as the similar user information, information on a situation of pregnancy and a situation of a partner, and information on results of action extraction and pregnancy support among all of the information of the similar user are preferentially outputted to a user B. The user B can preferentially browse information on the action, pregnancy and the partner of the other user whose action and the like are similar to those of the user B.

In user C setting information, a share item includes all attributes, three elements of {body temperature, menstruation, examination result}, and two types of analysis of {tendency analysis, disease risk warning}. Namely, a user C registers and shares data on the three elements, uses the tendency analysis of the element and a function of disease risk warning, and shares a result of the analysis. Like the present embodiment, the user may use only a function of specific analysis, and as the share item, a specific type of analysis is set.

An item for determination (determining item) includes attributes of {sex, age}, elements of {body temperature, menstruation, examination result}, and types of analysis of {tendency analysis, disease risk warning}. Namely, the degree of similarity between the users is comprehensively calculated by comparison of a combination of the plurality of these items.

A priority output item includes attributes of {disease, treatment}, an examination result, and types of analysis of {tendency analysis, disease risk warning}. The user C can preferentially browse information regarding the other user whose content of the item for determination is similar to that of the user C, such as diseases, treatment, examination results, and tendencies. The user C can know information of a user to whom a warning of a possibility of the same disease is outputted, for example. In this regard, a priority order can similarly be set with respect to a combination of a plurality of items.

FIG. 8 shows a setting example different for each individual user as a third configuration example of the user setting information 61. In user D setting information, user attributes of a share item are all attributes except for attributes of {pregnancy, partner}, for example, which are specific attributes for which "not share" is selected. Elements of the health information and the action information are all elements except for {note}, for example, which is a specific element to which "not share" is similarly set. Types of analysis are all types of analysis except for {pregnancy support}, for example, which is specific analysis to which "not share" is similarly set. As the similar user information, information except for all items to each of which "not share" is set in the share item is provided to a user D.

In the present embodiment, the share item and the items in the similar user information are basically associated with each other so as to become the same. Namely, information on items to each of which "share" is set is provided as the similar user information, but information on items to each of which "not share" is set is not provided as the similar user information. In a case where the number of share items is large, the amount of the similar user information to be provided increases to that extent. In a case where the number of share items is small, the similar user information is limited to that extent. In this regard, in another embodiment, the share item described above may be different from the items of the similar user information.

An item for determination (determining item) includes attributes of {sex, age, anamnesis}, elements of {action}, and types of analysis of {tendency analysis, action extraction}. A priority output item is analysis of {action extraction}. The user D can preferentially browse an action regarding the other user similar to the user D in any point of view of the item for determination (that is, an action estimated to contribute improvement of a health state). The user D can know similarity and difference of the actions between the user D and the other user. In another setting example, in a case of similarly setting with a focus on a symptom and medication, the user can know similarity and difference of the symptom or the medication between the user and the other user.

In user E setting information, a share item is all. An item for determination (determining item) includes attributes of {sex, age, pregnancy, partner}, elements of {examination result}, and types of analysis of {pregnancy support}. A priority output item includes attributes of {disease, treatment, medical institution}, elements of {symptom, note}, and types of analysis of {pregnancy support}. A user E can preferentially browse information regarding the other user whose pregnancy or situation of a partner is similar to that of the user E, such as medical institutions, symptoms and notes, and pregnancy support information.

In user F setting information, a share item is all. An item for determination (determining item) includes, in addition to attributes of {sex, age, disease, treatment}, {pregnancy=success} as specification of an attribute value of {pregnancy}. In a case where the attribute value is specified, the degree of similarity is calculated so that the degree of similarity of the user corresponding to the attribute value becomes higher when to determine the similarity. In this case, a user F can obtain and browse information of other user whose situation such as age and diseases are close to each other and for whom pregnancy is succeeded as a situation of pregnancy. For example, in a case where the user F is in a situation of no experience or failure of pregnancy and wants to know information from a person who succeeded pregnancy, the user F obtains the information on the person who succeeded pregnancy by means of the setting described above.

Like the setting example of the item for determination described above, the user can specify a different attribute or a dissimilar attribute between the users. Specification of the attribute value described above is not limited to the user attribute, but is similarly possible with respect to the element of the health information and the action information, or the analysis result. The checking unit 17 may narrow down similar users so as to extract only a user corresponding to a condition as the similar users when to determine the similar users by specifying the condition such as the attribute value described above.

As described above, the user setting information 61 can set a variety of conditions for each service and each user. Further, in the searching function 204 (will be described later), in similar to the setting example of the item for determination of the user setting information 61 described above, a search condition can be specified to search information of other user.

[Medical Examination Information]

FIG. 9 shows a configuration example of the medical examination information 52. A table of the medical examination information 52 shown in FIG. 9 contains, as items, medical institutions, treatment, treatment methods, achievement, examination institutions, examinations, examination types, examination items, examination methods, reference information, and the like. The medical examination information 52 contains management of the content of treatment and examination provided by each of the medical institution and the examination institution. The present system allows check of a similar user based on comparison of user information of a group of users by means of information management including the medical examination information 52.

As a "medical institution" item, identification information and a name of a medical institution are stored, and is "medical institution A (hospital A), for example". As a "treatment" item, identification information and a name of one or more medical treatment adopted by the medical institution are stored, and is "treatment A", for example. As a "treatment method" item, information on a treatment method, a treatment type and the like concerned with the treatment are stored, and is a "treatment method A" and the like, for example. As an "achievement" item, information on the number of cases of treatment, the number of cases of surgery and the like is stored. As the information, for example, there are the number of cases of a timing method per one year, the number of cases of artificial insemination per one year, a parameter, the number of pregnancy, a pregnancy rate, and the like.

As an "examination institution" item, identification information and a name of an examination institution that is an examination subject, which are associated with the medical institution are stored, and is an "examination company A", for example. In a case where the examination institution is the same as the medical institution, the information can be omitted. As an "examination" item, identification information and a name of one or more medical examination adopted by the examination institution are stored, and is an "examination A", for example. An "examination type" item is information indicating a type of examination such as a blood examination, a urine examination, an ultrasonic waves examination, palpation, is a "blood examination", for example. An "examination item" item is an item of a target for an examination or measurement, is an "LH (luteinizing hormone)" or an "FSH (follicle stimulating hormone)", for example, and includes the examination items as shown in FIG. 5C. As an "examination method" item, identification information and a name of an examination method associated with the examination are stored, and is "examination method A=EIA method (enzyme immunometric assay)" and the like, for example.

A "reference information" item is information such as a numerical value and a range that becomes reference (or criteria) of determination in the treatment or the examination, and corresponds to a value called a so-called reference value. The number range is "A=numerical value A1 to numerical value A2", for example. The numerical value A1 is a lower limit, and the numerical value A2 is an upper limit. For example, in a case where an LH value that is an examination item value is within a range A, it is determined to be normal or good. In a case where it is outside the range A, it is determined to be abnormal or bad, caution needed, and the like. The number range of the reference information indicates only threshold values, or a representative value within the range may be provided. The number range may be set for each period, like a range a in a follicular phase, and a range b in an ovulatory phase. The number range may be defined by a predetermined function (or mathematical scheme). Further, it is not limited to binary determination such as good or bad, and it may be determined with a plurality of levels using a plurality of numerical values.

The examination methods, the examination items, the reference information, and the like described above contains management of information on units. The units include various kinds such as [mol/L], [ng/mL], [mIU/mL], for example. The present system appropriately carries out conversion of units on the basis of the management information.

The information described above such as the reference information of the medical examination information 52 is set by the present system by using information that is provided or disclosed (or published) by the medical institution or the examination institution. Further, in a case where a plurality of treatment and examinations exists even in one medical institution or one examination institution, each treatment and information of each examination are managed so as to be associated with each other. The number range and the unit of the reference information is different from each other in accordance with the medical institution, the examination institution and the like. The reference information is set so that a plurality of users, a plurality of medical institutions and the like can deal with them individually and inclusively. The present system may individually set reference information different from each of the medical institutions and the examination institutions as it is. The present system may set a number range of unique and gradual reference information obtained by making unification in view of a number range of each of plural kinds of reference information provided from the plurality of medical institutions and the like.

As an example of setting of the unique reference information, in a case where there are an original number range of first reference information and a number range of second reference information, a logical "OR" condition thereof, a logical "AND" condition thereof or a statistical value and the like is adopted. Thus, a wider number range or a narrower number range than the original, or a unique number range is set as the number range unique to the present system. Otherwise, explanatory information about the medical institution, the examination institution, the treatment and the examination, related medical information, or link information for their reference, and the like may be stored in the medical examination information 52.

The analyzing unit 16 refers to the user attribute information 51 and the medical examination information 52, applies reference information associated with the medical institution and the examination institution of each user thereto, and determines a health state of each user. Further, as a first method regarding check of the similar user, the checking unit 17 refers to the medical examination information 52, determines an examination method and reference information according to the medical institution and the examination institution utilized by each user, and checks the similar user by using a plurality of users whose examination method, reference information and the like are the same as a comparison target.

Further, when to analyze a plurality of users, the analyzing unit 16 may apply the same reference information unique to the present system, which is set to the medical examination information 52, to them, and determine a health state of each of the plurality of users. As a second method regarding check of the similar user, the checking unit 17 utilizes users whose examination method, reference information and the like are different from each other as a comparison target. In the second method, in order to allow schematic comparison between the users whose examination method, reference information and the like are different from each other, information organized in a form of capable of comparing information on a plurality of medical institutions and examination institutions and the like is set to the medical examination information 52.

As an example of the information described above, a conversion equation unique to the present system is set to the medical examination information 52. The checking unit 17 refers to the conversion equation unique to the present system in the medical examination information 52, applies the conversion equation unique to the present system according to the medical institution and the examination institution utilized by each user to the information, and converts the information of each of the plurality of users to a form to be capable of schematically comparing them. The checking unit 17 then compares the information after conversion between the users, and checks the similar user.

In the conversion equation unique to the present system described above, for example, a numerical value is converted by means of a predetermined function or the like so as to match one examination method or a specific examination method. The processing for conversion unique to the present system described above may be carried out at the time of data registration by the user, or may be carried out at the time of check of the similar user. Even though it is not strict conversion, the conversion unique to the present system described above is useful to determine the similar user.

[Body Temperature Menstruation Data and Body Temperature-Menstruation Graph]

Although it is not illustrated, in the health information 53A, for example, information on body temperature and menstruation is managed on a table including items such as a user, a time and date, a body temperature numerical value, presence or absence of menstruation.

FIG. 10 shows an example of the body temperature-menstruation graph created on the basis of time series data of the body temperature and the menstruation in the health information 53A. A horizontal axis thereof represents the number of days, and a vertical axis thereof represents values of the basal body temperature. Reference numeral a1 denotes a menstruation period that is a menstruation date (so-called menstrual period) and its period. Reference numeral a2 denotes a menstrual cycle that is the number of days from a previous menstruation date a1 to a next menstruation date a1. Reference numeral a3 denotes an estimated ovulation day. Reference numeral t1 denotes a low temperature phase or a low temperature period in which a basal body temperature is relatively low. Reference numeral t2 denotes a high temperature phase or a high temperature period in which the basal body temperature is relatively high. Reference numeral a4 denotes a difference in temperature $\Delta T$ between the low temperature phase t1 and the high temperature phase t2. The difference in temperature $\Delta T$ is a value to unique to the present system, which is obtained by calculating it using a difference between the maximum value of the body temperature in the high temperature phase t2 and the minimum value of the body temperature in the low temperature phase t1, for example.

In the menstrual cycle a2, the respective phases including a follicular phase t3, an ovulatory phase t4, and a luteal phase t5 are shown. The vicinity of the ovulatory phase t4 and the predicted ovulation date a3 is a period when to be easy to get pregnancy. In this regard, when to display the body temperature-menstruation graph, information regarding internal secretion of female hormones and the like in each period, and information of influence on her mind and body may be displayed.

[Examination Result Data and Examination Result Graph]

FIG. 11 shows a table that is an example of the examination result data of each user in the health information 53A. The body temperature menstruation data and the examination result data are managed in association with the user attribute information 51 and the medical examination information 52. The table of the examination result data in FIG. 11 includes, as the items, a user, a medical institution, an examination institution, an examination method, examination time and date, a type, an item, a unit, and a numerical value. The "user" is a user ID or a user name. The "medical institution" indicates a hospital and the like used by the user. The "examination institution" indicates an examination company and the like used by the user. In a case where the medical institution is the same as the examination institution, the numeral value can be omitted. The "examination method" is information that indicates an examination method adopted for the examination by the examination institution. The "examination time and date" is time and date on which the examination was carried out. The "type" is a type of the examination, such as a blood examination, an ultrasonic waves examination, a semen examination, and the like. The "item" is the examination item described above, and is a specific female hormone, for example. As a plurality of types of the female hormones, there are an LH, an FSH, and the like (will be described later). The "unit" is a unit of the value of the examination item. In this regard, as the unit, two types or more units may exist. The "numerical value" is a numerical value of the examination item.

For example, a first row shows that the user A is concerned with treatment in the hospital A and has undergone an examination with the examination method A by the examination company A, a blood examination was carried out on July 1, for example, and LH=n1, FSH=n2, and the like as the numerical values of the plurality of types of endocrinological examinations.

FIG. 12 shows a graph of the LH and FSH in the female hormones, which are examination items for the blood examination of a healthy person, as a first example of the examination result graph created on the basis of the examination result data. A horizontal axis thereof represents the number of days, and a vertical axis thereof represents a female hormone value. In this regard, FIG. 12 shows a relationship of each period of t4 to t6 in FIG. 10. As ones that are deeply involved in diseases and pregnancy peculiar to females and the like, LH, FSH, E2, P4, AMH and the like are recited. The present system deals with a plurality of these types of examination results individually and inclusively.

An LH (luteinizing hormone) is a hormone which promotes ovulation and corpus luteum formation and thus can be used for ovulation prediction. Reference numeral 141 is a polygonal line of the LH value. As shown in FIG. 12, the LH becomes a temporary peak in the vicinity of the ovulatory phase t4, that is, the maximum value thereof occurs. The vicinity of the peak day of the LH corresponds to the ovulatory phase t4.

An FSH (follicle stimulating hormone) is a hormone that promotes follicle development. As the age gets older, the value of the FSH tends to be higher. Therefore, the FSH can be information for making a decision of continuation of in-vitro fertilization, for example. Reference numeral 142 is a polygonal line of the FSH values. The FSH similarly has its peak in the vicinity of an LH peak. The unit of LH and FSH is [mIU/mL], for example.

FIG. 13 shows an examination result graph of E2 and P4 in the female hormones as a second example of the examination result graph created on the basis of the examination result data. An E2 (estradiol) is a kind of estrogen (follicle hormone), and has functions such as maintenance of reproductive function, maturation of follicle, stimulation of ovulation, and proliferation of endometrium. The value of the E2 rises when the follicle grows up. When the value of the E2 reaches a certain value, the value of LH rises because E2 acts on the pituitary gland. For that reason, since the E2 allows an earlier grasp of ovulation tendency than observation of the LH, the E2 is useful for prediction of ovulation. Reference numeral 151 is a polygonal line of the E2 values. The E2 becomes higher before the vicinity of the LH peak in the ovulatory phase t4, and in the luteal phase t5. A unit of the E2 is [pg/mL], for example.

P4 (progesterone) is also called a corpus luteum hormone. The P4 has a function to suppress follicular growth, a function to thicken the endometrium, and a function to maintain pregnancy. Reference numeral 152 is a polygonal line of the P4 values. The P4 becomes higher in the luteal phase t5. A unit of the P4 is [ng/mL], for example.

An AMH (anti-Mullerian hormone) is a female hormone secreted from the follicle, and it is said that the function of the ovary can be estimated from the AMH value. A graph for the AMH is also created similarly. The female hormones are not limited to the above five types, and various types of other female hormones such as prolactin (PRL), testosterone, for example, are also applicable similarly. The examination results can similarly be applied not only to the above female hormones, including the examination items in FIG. 5C, but also to other chemical substances and index values.

The values of the body temperature, the menstruation, the female hormone and the like described above and variation thereof are medically related to each other. The present system analyzes the health state including relevance and tendency of each element by using reference information regarding values of the plurality of elements, which includes a body temperature, menstruation, female hormones, and the like described above. The user can browse the states of his or her body temperature, menstruation, female hormones, and the like together with the analysis results on the screen.

[Calendar Input Information]

FIG. 14 shows an example of management of the calendar input information 55. A table of the calendar input information 55 in FIG. 14 includes time and date, a type, and user input information as the items. The time and date are time and date corresponding to a date of the calendar and to which the user input information is registered. The type indicates a rough type of the user input information, and corresponds to a user attribute, and an element of the health information and the action information. The user input information indicates a text inputted by the user, selected identification information of choices and marks, and the like.

In the example of FIG. 14, a menstruation date, that is, having menstruation is registered on November 1. A "feel good" representing a feeling or the like as a text of a note, and a face mark A are registered on November 2. "having severe stomachache" as a symptom is registered on November 4. An "exercise A" as an action, particularly, as exercise therapy is registered on November 6. "treatment A" as treatment is registered on November 8. An "examination item, examination numerical value, examination company A" and the like as an examination result are registered on November 9. "medicine A, period, and amount" as medication are registered on November 10. A "hospital A, treatment A" as treatment (hospital visit) are registered on November 11. Further, as texts of notes, thoughts of the treatment A in a hospital A and comments of evaluation and the like, for example, "I got treatment A in hospital A. Dealing was kind. Waiting time was long." are registered on November 11.

The symptoms, the actions and the like of the user described above can be inputted by means of the choices, marks or the like prepared and set in advance in the present system, or can be inputted by a free text. The present system may set a typical action, a typical symptom, and the like as the choices. For example, in a case where a symptom or an action is registered by a text of a note, it includes "feel stress", "disappointed", and the like.

[Analysis Information]

Although it is not illustrated, the analysis information 56 is managed on a table including items such as a time and date of analysis and ID, an analysis target user, an analysis type, an analysis item, an analysis result, for example. The analysis type is a type such as tendency analysis. The analysis item is an attribute or an element of an analysis target. The analysis result is analysis result data themselves or identification information for reference thereof. In this regard, as the analysis processing, various kinds of processing other than the analysis processing shown in the present embodiment are available.

[Check Information]

FIG. 15 shows an example of a check result by comparing user attributes as a configuration example of the check information 57. A table of the check information 57 in (a) of FIG. 15 is an example of a list of similar users of each user, and shows a case of a list of similar users regarding a user X. The table of the check information 57 in (a) includes, as columns, a similarity order indicating #, the degree of similarity, a user, a similar attribute, and a dissimilar attribute. In this list, the other users are associated with each user as similar users in order of the degree of similarity.

The "similarity order" indicates a descending order of the degrees of similarity regarding a plurality of other users. The "degree of similarity" indicates a value of the degree of similarity that is an index value representing similarity between the users, and in the present embodiment, it indicates the degree of similarity regarding the user attribute. The "user" indicates a user name, a user ID, and the like of other user who is a similar user. The "similar attribute" indicates an attribute which of the user is similar to that of the other user. The "dissimilar attribute" indicates an attribute which of the user is not similar to that of the other user.

The "degree of similarity" indicates any of two types of degrees of similarity, that is, R and L in the present embodiment. The degree of similarity R is a numerical value, for example, is a numerical value normalized in a range of 0 to 100. The degree of similarity R represents higher similarity as the numerical value becomes larger. For example, the degree of similarity with the user A is R1, and the degree of similarity with the user B is R2, herein R1>R2. The degree of similarity R may be calculated on the basis of a differential value or the like. In that case, it represents higher similarity as its numerical value is smaller. The degree of similarity L is one of a plurality of levels that is rougher than the degree of similarity R. For example, the degree of similarity R with a fine numerical value is calculated when to check, and the degree of similarity L is further obtained by sectioning the degree of similarity R by intervals of a predetermined threshold value. For example, the degree of similarity with the user A is L1, and the degree of similarity with the user B is L2. It represents that L1 has higher similarity than L2.

The items of the "similar attribute" and the "dissimilar attribute" indicate information obtained by determining and organizing information on similar parts and information on dissimilar part with respect to the user attribute. In the present example, in a first row between the user X and the user A, each attribute value of attributes A to D is similar, and each attribute value of attribute E to H is dissimilar. In a second row between the user X and the user B, that of the attributes A to C is similar, and that of the attributes D to H is dissimilar. In a third row between the user X and the user C, that of the attributes A, B is similar, and that of the attributes C to H is dissimilar. A list of similar users is similarly managed with respect to a unit of each of the other users.

The present system refers to the check information 57, determines similar users in order described in the list, determines the similar user information to be provided for each user, and describes them in the output information 58. For example, in the similar user information to be provided to the user X, similar users are preferentially determined from the list described above in order of the users A, B, C and the like, which is the similarity order, and it is determines as share information of the similar user.

The check information 57 in (b) of FIG. 15 corresponds to the table in (a), and shows an example of a table in which information on comparison of each attribute between the users is stored. This table includes, as columns, an attribute, an attribute value of the user X, an attribute value of the user A, and the degree of similarity of the attribute. For example, the checking unit 17 compares attribute values of each attribute such as an attribute A, B, or C between the user X and the user A, calculates the degree of similarity (hereinafter, referred to as "r") of the attribute unit, and stores them in the "the degree of similarity of the attribute" item. For example, the degree of similarity r1 regarding the attribute A (example: age) is calculated from a differential value or the like obtained by comparing an attribute value a1 of the attribute A of the user X with an attribute value a2 of the attribute A of the user A. The present system manages definition information on calculation of the degree of similarity for each attribute. The last row of the table in (b) described above indicates the degree of comprehensive similarity regarding the user attributes by comparison of all attributes. The checking unit 17 calculates the degree of comprehensive similarity by means of predetermined calculation using the degrees of similarity r1, r2 and the like of the respective attributes. This degree of similarity corresponds to a value of the degree of similarity (R1) of the table shown in (a). As an example of the calculation of the degree of comprehensive similarity (R), a total sum of the degrees of similarity (r) of the attributes is divided by the number of attributes (n). Namely, it is "R={r1+r2+ . . . +rn}/n". As another example of the calculation, a weighting value regarding preferential order of attributes is multiplied to the degree of similarity of each of the attributes. The weighting values for the respective attributes are w1, and the like. Namely, it is "R={r1×w1+r2×w2+ . . . +rn×wn}".

As still another example of the calculation, the degree of comprehensive similarity may be calculated by extracting the highest one of the degrees of similarity of the attributes from the attributes as a representative to set to the degree of comprehensive similarity, or extracting ones whose degree of similarity is a predetermined threshold value or more from the attributes. The present system manages definition information on calculation of the degree of comprehensive similarity.

In a case where the check is element comparison of the health information and action information or analysis result comparison, the table is also managed in the similar manner described above. For example, in a case of the element comparison of the health information, information on "the degree of comprehensive similarity regarding the health information", "the degree of similarity of an element unit", "the degree of similarity of each predetermined item of the element", "similar element", "dissimilar element" and the like is managed in the table described above. Similarly, in a case of the analysis result comparison, information on "the degree of comprehensive similarity regarding analysis results", "the degree of similarity of an analysis result of each analysis type", "the degree of similarity of each predetermined item of the analysis result", and the like is managed in the table described above. The "the degree of similarity of each predetermined item" is the degree of similarity of the difference in temperature $\Delta T$ or the degree of similarity of the tendency of the menstrual cycle a2, for example.

Moreover, in a case where the degree of similarity (R) between the users is comprehensively calculated on the basis of four items of the user attribute, the health information, the action information, and the analysis result, the degree of similarity (for example, RA, RB, RC, RD) regarding each item and the degree of similarity (R) obtained by total calculation thereof are managed in the check information 57. As an example of the calculation of the degree of comprehensive similarity (R), it is "R={RA×WA+RB×WB+RC×WC+RD×WD}" or the like by using weighting values of the respective items (for example, WA and the like).

A table of the check information 57 in (c) of FIG. 15 is a list of the similar users regarding the attribute A in response to the tables of (a) and (b) as an example of information organized with an attribute unit. The checking unit 17 and the statistical function 205 (will be described later) may manage such information. The table in (c) includes, as items, person number order indicated by #, an attribute value, a user, and the number of persons. In this table, information on corresponding users and the number of users, and the like is stored for each attribute value of the attribute. For example, with respect to the attribute A, there are users A, D, G, J and the like as similar users corresponding to the same attribute value a1, and the number of users is N1. Similar users corresponding to the similarly attribute value a2 are users B, E, H and the like, and the number of users is N2.

[Check Processing (1)—User Attribute Comparison]

FIG. 16 shows an example of a case where of the user attribute comparison at Step S24A as an example of similar user determination by the check processing at Step S24 in FIG. 4. The checking unit 17 compares attribute values of the plurality of attributes in the user attribute information 51 between the users, and determines similarity between the users. The example of FIG. 16 is the case where the user X is compared with the users A, B, C who are the other users. The attributes A to H and the like are attributes in the user attribute information 51, and all attributes are share items and items for determination. For example, an attribute A is age, an attribute B is a disease, and an attribute C is treatment.

The checking unit 17 refers to attributes, which is the item for determination in the user attribute information 51, of a pair of the user X and the user A who is a comparison target user, for example, and compares the attribute values of the respective attributes. The checking unit 17 first determines similarity of each attribute, that is, calculates the degree of similarity (r) of the attribute in FIG. 15. For example, the checking unit 17 determines "similar" in a case where the attribute values are the same as or closer than each other. Otherwise, the checking unit 17 determines "dissimilar". Namely, the degree of similarity (r) of the attribute is calculated by binary of "similar (1)"/"dissimilar (0)". For example, in a case where the attribute value a1 and the attribute value a2 of the attribute A between the user X and the user A are compared with each other and these are the same or closer values, the degree of similarity (r) of the attribute is "similar". Otherwise, the degree of similarity (r) of the attribute is "dissimilar".

The calculation of the degree of similarity (r) of the attribute described above may be a method of taking a difference of the attribute values. For example, a difference between numerical values of the "age" attribute. The degree of similarity of the attributes is calculated as higher value as the differential value is smaller. Further, with respect to an attribute in which simple comparison is impossible by the difference or the like, a group for determination of similarity regarding the attribute value may be set as management information by the present system, the similarity may be determined by using the setting information, and the degree of similarity may be calculated. For example, the groups are set so that the attribute values a1 to a3 regarding the attribute A is set to the same first group, and the attribute values a3 to a6 is set to the same second group, and the like. For example, the checking unit 17 compares the attribute value a1 of the attribute A of the user X with the attribute value a2 of the user A. In a case where they are the same value, it is determined to be L1 that is a level with high similarity. In a case where they are different values but belong to the same group, it is determined to be L2 that is a level with medium similarity. In a case where they are different values and do not belong to the same group, it is determined to be L3 that is a level with low similarity.

Further, in a case where the attribute value is a text, it can be determined by using a group of setting information according to similarity of words in the similar manner as described above. For example, with respect to the "disease" attribute, {disease a, disease b, disease c} are set to the same group for high similarity.

The checking unit 17 calculates the degree of comprehensive similarity (R1) regarding the user attributes between the users X and A on the basis of the degrees of similarity of the respective attributes A to H (which are referred to as "rA to rH"). A calculation example of the degree of similarity (R) is calculation according to the number of attributes with "similar". In the pairs of the users X and A, reference numeral 161 denotes the attributes A to C with "similar", and reference numeral 162 denotes the attributes D to H with "dissimilar". Reference numeral 163 denotes the attributes A, B with similar between the users X and B. Reference numeral 164 denotes the attribute A with similar between the users X and C. The degree of similarity R1 between the users X and A is "R1=3", for example. Similarly, it is calculated so that the degree of similarity R2 between the users X and B is "2" and the degree of similarity R3 between the users X and C is "1". The number of similar attributes between the users X and A is three of all of the attributes, which is the largest number. Therefore, the degree of similarity R1 relatively becomes higher.

Another calculation example of the degree of similarity (R) is calculation such as a total sum of the degrees of similarity (r) of the attributes as described above. In a case where the number of items for determination is three of attributes A to C, an example of a calculation formula is R={rA+rB+rC}/3. In a case where there is a priority order of the attributes, it is R={rA×wA+rB×wB+rC×wC} and the like. The checking unit 17 similarly calculates the degree of similarity (R) with respect of a pair of the users.

The checking unit 17 may compare the degree of similarity (R) described above with a predetermined threshold value (example: h1, h2) to section it, and obtain the degree of similarity (L) by the level. For example, in a case where R is a first threshold value h1 or more (R≥h1), the degree of similarity (L) is L1. In a case where R falls within a range between the first threshold value and a second threshold value (Th1>R≥Th2), the degree of similarity (L) is L2. In a case where R is smaller than the second threshold value (Th2>R), the degree of similarity (L) is L3.

As a result of the above check, the degrees of similarity of the user X against each of the users A, B, C become "R1>R2>R3", and "L1>L2>L3". Namely, a plurality of similar users of the user X is associated with the user X in order of the users A, B, C, for example. Further, the checking unit 17 may associate only other users whose degree of similarity (L) is a predetermined level or higher with the user X as the similar users.

Reference numeral 165 is an example of output of the similar user information based on the result of the check, and indicates that the user attribute information, which is the share information of the user A who is the first similar user against the user X, for example, is provided to the user X. At this time, the outputting unit 18 may provide, to the user X, information with a format obtained by organizing and comparing the similar information part (the attribute A to C) indicated by the reference numeral 161 and the dissimilar information part (attributes D to H) indicated by the reference numeral 162 between the users X and A.

[Check Processing (2)—Health Information Element Comparison]

An example of similar user determination in a case of comparing elements of the health information at Step S24B and the like in the check processing at Step S24 is as follows. This processing can basically be realized in the similar manner (thinking) to the case of the user attribute comparison. The checking unit 17 compares data of various kinds of elements in the health information 53A between the users for each element, calculates the degree of similarity (hereinafter, referred to as "f") of each element unit, and calculates the degrees of comprehensive similarity (R, L) between the users regarding the health information by means of predetermined calculation using the degree of similarity (f) of each element unit. Here, target elements are five types of (a) body temperature, (b) menstruation, (c) examination result, (d) symptom, and (e) medication, which have been described above.

An example of a calculation formula for the degree of similarity (R) is "R={[degree of similarity fa of element a]+[degree of similarity fb of element b]+ . . . +[degree of similarity fe of element e]}/[the number of elements (n=5)]". In a case where there are weighting values for priority order of each element (for example, wa and the like), it is "R={fa×wa+fb×wb+ . . . +fe×we}" or the like.

The checking unit 17 reads out data in a target period of data of elements in the item for determination of the health information of the user X and the user A, who are comparison target users, for example, the body temperature and the menstruation, from the DB 50. For example, the target period is a range of the same time and date (example: December, 2013), or a range in which the time and date is different, but time lengths are the same (example: 30 days), or a period by one or more menstrual cycle of each user, or the like. The present system sets the target period for each processing.

The checking unit 17 compares time series values of data of the element of the comparison target users for the target period, and calculates the degree of similarity (f) of the element unit on the basis of closeness of the both.

Further, the checking unit 17 may calculate the degree of similarity regarding a predetermined item in the element during comparison of the data of the elements such as the body temperature and the menstruation, and calculate the degree of similarity (f) of the element by using the degree of similarity of each item. The predetermined item is the difference in temperature ΔT in a case of the body temperature data, the menstrual cycle a2 in a case of the menstruation data, or the like, for example. For example, the checking unit 17 compares the numerical values of the difference in temperature ΔT between the users, and calculates the degree of similarity of the difference in temperature ΔT by means of a method of taking a differential value or the like. The checking unit 17 obtains the degree of similarity (fa) of the body temperature unit by means of the predetermined total calculation similar to the above using the degree of similarity calculated of each item such as the difference in temperature ΔT.

In a case of comparison of the examination result data, it is also possible in the similar manner to the above. The checking unit 17 reads out data of a plurality of types of female hormones (LH, FSH, E2, P4) for the target period from the examination result data of the comparison target user, for example. The checking unit 17 compares time series values of each of the female hormones as the examination items, and calculates the degree of similarity of the examination item unit. For example, the degree of similarity of the LH can be obtained from comparison of numerical values of the LH. The checking unit 17 obtains the degree of similarity (fc) of the examination result unit by means of the predetermined total calculation using the degree of similarity of each examination item. An example of a calculation formula is "fc={[degree of similarity of LH]+[degree of similarity of FSH]+[degree of similarity of E2]+[degree of similarity of P4]}/[number of examination items (n=4)]".

[Check Processing (3)—Graph Comparison]

FIG. 17 shows processing in a case of graph comparison at Step S24B particularly as processing for similar user determination as an example using an examination result graph. The checking unit 17 calculates the degree of similarity (R) between the users by comparing and matching a graph of the user X who is one comparison target and a graph of the user A who is the other comparison target.

(a) in FIG. 17 shows an example of the examination result graph of a specific examination item (example: P4) of the user X by one cycle of a menstrual cycle. Similarly, (b) shows an example of the examination result graph of the same examination item of the user A by one cycle of the menstrual cycle. Points such as a point 171 and a point 172 show values of the examination item based on examination result data thus inputted and according to dates of the examination and registration. The checking unit 17 reads out data of a target period, for example, for one cycle of the menstrual cycle currently immediate from the body temperature-menstruation graphs of the users X and A.

(c) in FIG. 17 shows a state where the graph of the user X in (a) is compared with the graph of the user A in (b). The checking unit 17 superimposes the graph of the user X in (a) in the target period onto the graph of the user A in (b) as shown in (c). In this regard, in a case where lengths of the period such as the menstrual cycle of both graphs is different from each other, the period may be adjusted so as to make up the same. For example, this adjustment may be a method in which the period of data of one user is expanded and contracted, or a method in which edges of the data of the one user is cut down or omitted.

As shown in (c), the checking unit 17 compares the numerical values of both graphs, and calculates the degree of similarity of the female hormone unit in the examination item on the basis of closeness of the both graphs. The checking unit 17 compares, as shown with arrows in (c), numerical values of each of a plurality of time points that correspond to the both graphs in time series. The checking unit 17 takes a differential value between the numerical values at each time point as shown at an arrow 173. The time points at each of which the differential value is taken may be arranged at regular intervals, or may be all time points at each of which the examination item value is registered.

In this regard, examination, time and date of registration, and presence or absence of the registration of the examination item values are different from the other users. Thus, the checking unit 17 may interpolate numerical values of a graph so as to allow both graphs to be compared with each other. In interpolating processing, the checking unit 17 connects numerical values of the examination item values at the time of registration dates by a straight line or a curve line to constitute an interpolated value at the time of a date on which the value has not been registered. The graph after the interpolating processing becomes a graph by a polygonal line or a curve line. The interpolating processing may be achieved by utilizing a known technique such as a Bezier curve. Further, the interpolating processing may use a reference graph that is set in advance.

The checking unit 17 takes a total sum of the respective differential values of the arrows 173 in the target period of (c) described above, and divides the total sum by the number of time points or the number of days in the target period, thereby obtaining the degree of similarity at a graph unit of the examination item. Similarly, the checking unit 17 calculates the degree of similarity of a graph of each of other examination items.

The target period may be a period by menstrual cycles continuing plural times, or a specific period such as the follicular phase t3. The checking unit 17 may determine similarity with respect to tendency of periodic variation of a body temperature, menstruation, a female hormone or the like in a period by a plurality of the menstrual cycles. The outputting unit 18 may provide information on graph comparison like (c) when to output the similar user information to the user.

Further, the present system may utilize a reference graph in the processing for graph comparison described above. The reference graph is set for each element such as the body temperature. The reference graph is a graph by statistical data of healthy person samples provided by the medical institution or the like, for example. The reference graph may be a graph uniquely set by the present system in view of the medical information. The reference graph is a graph by a curve line or a polygonal line, which is set so as to correspond to a number range of reference information in the medical examination information 52.

(d) in FIG. 17 shows an example of the reference graph regarding a graph of a predetermined examination item (example: P4). The reference graph in (d) is constituted by a smooth curve. For example, the checking unit 17 reads out the reference graph in (d) corresponding to the graph of the examination item of the user X in (a) from the DB 50. The checking unit 17 superimposes the graph of the user X in (a) on the reference graph in (d), compares them with each other, and calculates an index value that represents closeness of the graph of the user X with respect to the reference graph. The index value can be calculated by means of calculation of differential values or the like in the similar manner to that in (c) described above. The checking unit 17 compares each of various kinds of graphs of the users with a corresponding reference graph, and calculates the index value thereof. The checking unit 17 may compare the index values calculated as described above between the respective users, and calculate the degree of similarity (R) regarding the element between the users on the basis of these differential values and the like.

The above function to compare the graphs allows a similar user whose graph is similar to that of the user to be determined and extracted. The user can browse information containing a graph of other user that is similar to the graph of the user. Further, the more the user records data, the larger data of the comparison target including the graph comparison described above becomes. Thus, it becomes easy to extract a similar user. Therefore, it is possible to heighten a willingness to record data of the user.

[Check Processing (4)—Action Comparison and Symptom Comparison]

FIG. 18 shows an example of similar user determination in a case of the action comparison at Step S24C and the symptom comparison at Step S24B in the check processing at Step S24. (a) in FIG. 18 shows examination result graphs in a period of a menstrual cycle Ga of the user X and information on actions and symptoms registered in the period. Examination items are various kinds of female hormones {LH, FSH, E2, P4}. Similarly, (b) in FIG. 18 shows examination result graphs in a period of a menstrual cycle Gb of the user A and information on actions and symptoms in the period. The menstrual cycles Ga, Gb each of which is a target period is one cycle of the last menstrual cycle from a current date, for example.

In registered data of the user X in the period of the menstrual cycle Ga in (a), the actions are {exercise a, exercise b, diet a, diet b} and the like, and the symptoms are {symptom a, symptom b, symptom c, symptom d} and the like. In registered data of the user A in the period of the menstrual cycle Gb in (b), the actions are {exercise a, exercise c, diet a, diet c} and the like, and the symptoms are {symptom a, symptom b, symptom e, symptom f} and the like.

The checking unit 17 compares action data of a pair of users X and A who is a comparison target in the target period, for example. The actions of {exercise a, diet a} are the same and common in the comparison. Further, the actions of {exercise b, diet b} of the user X are different from the actions of {exercise c, diet c} of the user A.

The checking unit 17 determines similarity of each action type such as the exercise a between the users X and A, and calculates a score that is an index value of the similarity, for example. For example, in a case where values of the actions are the same as each other like the exercise a, the checking unit 17 adds three to the score like "+3". Further, in a case where the values of the actions are different from each other and it is determined to be "similar", the checking unit 17 adds one to the score like "+1". Further, in a case where the values of the action are different from each other and it is determined to be "dissimilar", the checking unit 17 does not add anything to the score or subtracts one from the score like "–1".

Determination of "similar" or "dissimilar" of the actions or the like is possible by setting or the like of an action group for determining similarity in the similar manner to the user attribute comparison or the like described above. For example, a group of {exercise b, exercise c, and the like}, a group of {diet b, and the like}, and a group of {diet c, and the like} are set. In this case, since the exercise b of the user X and the exercise c of the user A belong to the same group, it is determined that they are "similar" actions. Further, since the diet b of the user X and the diet c of the user A respectively belong to different groups, it is determined that they are "dissimilar" actions.

The checking unit 17 calculates the degree of comprehensive similarity (R) regarding the actions between the users on the basis of the result of the comparison of the actions between the users. For example, the checking unit 17 obtains the degree of similarity by calculating a total sum of scores of the respective actions described above regarding all of the registered actions. The more the same actions or the similar actions are registered, the higher the degree of similarity becomes.

The checking unit 17 may calculate the degree of similarity described above in view of an amount, frequency, continuity and the like of each action type. By registration of the action data and the function of the tendency analysis, information on the action amount such as the number of days of registration and a total time, frequency, a period of duration and the like is stored in the analysis information 56 for each user and each action type. For example, the number of days of registration regarding the exercise a of the user X for one month is 10 days, and the number of days of registration regarding the exercise a of the user A for one month is 12 days. The checking unit 17 calculates, by using the information, the degree of similarity of the exercise a between the users X and A on the basis of a differential value of the number of days of registration, for example.

The symptom comparison is also possible in the similar manner to the above. The checking unit 17 compares information of the symptoms between the user X and the user A, and determines that {symptom a, symptom b} are the same and common, but {symptom c, symptom d} of the user X are different from {symptom e, symptom f} of the user A. It is determined that the symptom c and the symptom e are "similar" to each other, and it is determined that the symptom d and the symptom f are "dissimilar" to each other. For example, the checking unit 17 determines that the number of the same symptoms is two, the number of similar symptoms is one, and the number of dissimilar symptoms is one. The checking unit 17 obtains the degree of similarity of the symptoms by calculating a total sum of scores of all symptoms. The score is an index value of similarity for each type of symptom.

Further, the checking unit 17 reflects not only the type of symptom but also the number of days of registration of the symptom, the degree of symptom and the like when to calculate the degree of similarity of the symptom. For example, with respect to "having a stomachache" as the symptom a, the number of days of registration for one month is 6 days, and there are three values of heavy, medium and light as the degree of the symptom a for each registration date. In order to calculate the amount of symptom, for example, "+3", "+2" and "+1" are set to "heavy", "medium" and "light", respectively. For example, in a case where there are one heavy day, two medium days, and three light days, then the amount of the symptom a of the user X for one month is ten of "1×3+2×2+3×1=10". Similarly, the amount of the symptom a of the user A is calculated, and is 12, for example. The checking unit 17 obtains the degree of similarity of the symptom a as "12−10=2" on the basis of the differential value of the amounts of symptom a of the users.

The functions of the action comparison and the symptom comparison described above allow the similar user to be determined by means of similarity of actions and/or symptoms between the users. The user can browse information containing actions and symptoms of other users, which are similar to the actions and symptoms of the user.

[Check Processing (5)—Text Comparison]

An example of the similar user determination in a case of comparing texts of the notes at Step S24C in the check processing at Step S24 is as follows. In a case where text data such as notes are compared between the users, the checking unit 17 checks words included in a text by the text mining function to extract each of the words or a specific word. The checking unit 17 calculates, for each of the extracted words, the number of days of registration, the number of appearance, frequency, continuity and the like. The checking unit 17 calculates the degree of similarity regarding the text of the note between the users by using the calculated values.

The checking unit 17 reads out text data of notes in a target period of a calendar of a comparison target user. The checking unit 17 checks the text data, and extracts words the same as or similar to those between the users. Extraction of the similar words may carry out by using the group of setting information according to the similarity described above, for example. The checking unit 17 calculates the number of the same or similar words thus extracted, and calculates amounts such as the number of days of registration and the number of appearance for each word. The checking unit 17 calculates the degree of similarity regarding the content of the texts of the notes between the users on the basis of information on the calculated words.

For example, with respect to registration by the user X for one month, there are three days for a "word a", four days for a "word b" and the like. With respect to registration by the user A for one month, there are two days for the "word a", two days for a "word c" and the like. The "word b" and the "word c" belong to a similar group. There are one same word and one similar word between the users X and A. For example, the checking unit 17 adopts three days, which is smaller one of the number of days of registration of the same "word a", and two days, which is smaller one of the number of days of registration of the similar "words b, c", and calculates the degree of similarity as "1×3+1×2=5".

The function of comparing the texts of the notes described above allows the similar user to be determined by means of similarity of the content of the texts of the notes between the users. The user can browse information containing notes of other users, the content of which is similar to the content of the notes of the user.

[Check Processing (6)—Analysis Result Comparison]

An example of the similar user determination in a case of comparing the analysis results at Step S24D in the check processing at Step S24 is as follows. The checking unit 17 refers to the analysis information 56 or the message information 58a of the output information 58 regarding the comparison target user, compares values of analysis results of the analysis types, which are the item for determination, or values of the messages, and calculates the degree of similarity regarding the analysis result.

For example, in a case where results of the tendency analysis for the body temperature and the menstruation are compared, the checking unit 17 refers to a value indicating a state of tendency of a difference in temperature ΔT in a target period including a plurality of menstrual cycles of the users X and A who are comparison targets. For example, the user X has {g1, g2} as values of the menstrual cycle a2 and {ΔT1, ΔT2} as values of the difference in temperature ΔT previous two times. Both g1 and g2 of the menstrual cycle a2 were 32 days, and a variation amount (g2-g1) was 0 days. Further, a variation amount of ΔT was (ΔT2−ΔT1), All was less than 0.3° C., and ΔT2 was 0.3° C. or higher, whereby it was a good state (a state of a so-called two-phase pattern). Namely, in the period, a2 was maintained and ΔT was improved.

As a result of the tendency analysis, a value of the state of the tendency regarding the body temperature of the user X was {improvement of the difference in temperature ΔT}. The checking unit 17 compares the variation amounts or the values of the state of the tendency regarding the items such as the difference in temperature ΔT described above between the users X and A, and calculates the degree of similarity of each of the items on the basis of closeness of the values. For example, in a case where the values of the state of the tendency of the body temperature of the users X and A are the same as each other, the degree of similarity of the difference in temperature ΔT becomes a high value.

The checking unit 17 calculates, by predetermined total calculation using the degree of similarity of each of the items described above, the degree of similarity of the analysis type unit between the users, for example, the degree of similarity of the results of the tendency analysis of the body temperature and the menstruation. With respect to analysis results of the other analysis types such as action extraction, the degree of similarity thereof can be calculated in the similar manner as described above. Moreover, the checking unit 17 can calculate the degree of similarity regarding a comprehensive analysis result between the users by means of predetermined total calculation using the degree of similarity of each analysis type unit thus calculated as described above.

[Check Processing (7)—Comparison Between Partners and Comparison Between Pairs]

The check processing described above is check of similarity by comparing various kinds of items or elements in the user information. However, in the similar to this, check of similarity by comparing them between the partners described above, and check of similarity by comparing a pair unit are possible. The checking unit 17 compares data on the attributes, the elements in the health information and the action information, the graphs, one or more predetermined item or element of the analysis result between the partners of the users, calculates the degree of similarity between the partners, and makes the connection between the similar users of each user in accordance with the degree of similarity. Further, the checking unit 17 compares data on the attributes, the elements in the health information and the action information, the graphs, one or more predetermined item or element of the analysis result between a pair unit of the first user and the second user, calculates the degree of similarity between the pair, and makes the connection between the similar users of each first user in accordance with the degree of similarity.

[Output Information]

FIG. 19 shows a configuration example of the output information 58. (a) in FIG. 19 shows a configuration example of the message information 58a. The message information 58a is managed in time series so that a history of information that will be outputted now and information that has been outputted in the past are contained. A table of the message information 58a in (a) includes, as items, time and date (or a date), an output ID, a user, and a message. The "time and date" indicates time and date when a message is outputted or time and date when a message was outputted. The "output ID" is identification information of the output. The "user" indicates a user name, a user ID or the like that is an output destination of the message. The "message" is a text of the content of an output message or identification information for reference thereof. In the message information 58a, a type of message may be managed. The type is "tendency analysis", "disease risk warning", and "data analysis", for example.

In the present example, output ID "001" indicates November 1, and "Difference in temperature has become 0.3° C. or higher." as a tendency analysis message that is a notice message to the user A. This is an example of the tendency analysis of the body temperature. Similarly, output ID "002" indicates that "An LH value has been improved in this examination result compared with the last (or previous) examination result." as an output example of the tendency analysis of the examination result.

Output ID "003" indicates that "There is a possibility of a disease A. Consultation is recommended." as an output example of a disease risk warning and consultation recommendation message. This is an example of warning (or alert) of a possibility of a disease and consultation recommendation (or recommendation for consultation). The consultation recommendation is consultation recommendation such as specific treatment or examination and a medical institution that are thought to be effective as handling of the disease A.

Output ID 004 indicates an output example of action extraction according to a tendency analysis result, "The LH value has been improved compared with a previous menstrual cycle. An action A is recited as past actions that are likely to be relevant to this." as a data analysis message that is a notice message. Similarly, output ID 005 indicates an output example of action tendency analysis and action extraction, "Exercise A has been done xx days last month. Diet A has been done yy days this month". Similarly, output ID 006 indicates an output example of symptom tendency analysis and symptom extraction, "Symptom A has appeared for xx days last month. Symptom B has appeared for yy days this month".

Output ID 007 indicates an output example of pregnancy support, "Ease of pregnancy is xx. YY is recommended to the partner." as a data analysis message that is a notice message. This is an example of notification of a state such as ease of pregnancy of the user, and advice or recommendation such as an action regarding a pregnancy activity with a partner.

A link such as a URL may be attached to the output message. The URL to be attached is not limited to a static URL, but may be a URL that is dynamically collected. For example, in a case of warning of a possibility of a disease, the URL is linked to a page for explanatory information of the disease. For example, it is a URL that exists on the Internet and is collected by a certain word. Further, in a case of consultation recommendation, the URL is linked to information provision of treatment and examination against a target of the recommendation, or search and information of a medical institution and the like.

(b) in FIG. 19 shows a configuration example of the similar user information 58b in the output information 58. A table of the similar user information 58b in (b) includes, as items, time and date, an output ID, a user, a similar user, and provided information. The "time and date" are time and date when the similar user information is outputted or time and date when the similar user information was outputted. The "user" is identification information of a user who is an output destination. The "similar user" is identification information of a similar user in the similar user information to be provided. The "provided information" is the content of the similar user information to be provided, and contains identification information of a share item or data on the share item themselves.

[Screen Including Information of Each User]

FIG. 20 shows, as one example of a screen for a service in the present system, a screen on which information of each user is displayed as "MY medical record". This MY medical record is comprehensive information that represents a health state and the like of each user as information peculiar to the present service. The present screen includes a field 101 for the user attribute information, a field 102 for the body temperature-menstruation graph, a field 103 for the examination result graph, a field 104 for the calendar, a field 105 for the output message of the analysis result, and the like.

Information of each attribute of the user based on the user attribute information 51 thus registered is displayed in the field 101. A right side thereof is an example in which [treatment history] and [action] are displayed. The [treatment history] indicates a display example based on the value of the "treatment" attribute described above. The [action] indicates a display example of main exercise, diet and the like of the user based on the calendar input information 55 and the action extracting function.

The body temperature-menstruation graph of the user is displayed in the field 102 on the basis of the health information 53A and the graph data 54 in the DB 50 like the example of FIG. 10. Further, the result information of the tendency analysis of the body temperature and the menstruation may also be displayed in the field 102. Further, a button for "registration of body temperature" causes a field for registration of body temperature data to be displayed by a pop-up or the like, or causes the screen to transition to another screen. The user can directly input a value of the body temperature or select it from choices in the field to register it. Further, the body temperature can be registered by plotting the value in the graph. Similarly, a button for "registration of menstruation" allows information such as a menstruation date to be registered.

A graph of the female hormone or the like of the blood examination result of the user is displayed in the field 103 on the basis of the health information 53A and the graph data 54 in the DB 50 as shown in FIG. 12 or the like. Further, the result information of the tendency analysis of the examination result may also be displayed in the field 103. Further, a button for "registration of examination result" causes a field for registering examination result data to be displayed. The user can directly input a value of the examination result or select it from choices in the field to register it. Further, a selection field in a case where there is a plurality of types of examination items is provided in the field 103, and a graph according to the examination item selected by the user is displayed.

Various kinds of information such as a basal body temperature, menstruation, an examination result, a symptom, medication, an action, a note, treatment (hospital visit), and the like can be inputted and recorded in the field 104 for each date of the calendar, and the user can browse various kinds of information registered in the calendar input information 55. In a case where a portion in which information has already been registered is selected by the user in the dates of the calendar, the content of the registered information is displayed in a balloon or another field, for example. Information on a period including a current date is displayed in the field 104. The user can confirm, look back on, and remember the registered information described above by mean of the calendar, and can enter and schedule plans such as various kinds of actions, visiting of a hospital and the like.

The latest message information regarding analysis results of the various kinds of analysis described above is displayed in the field 105. Messages may be displayed in another field or on another screen.

Each of the fields or each of the items on the screen described above can set whether to display it or not, a position thereof, timing and the like by user setting. For example, a predetermined field is in a folded state when it is not displayed. In a case where the user wants to view it or carry out a selection operation or it becomes specific timing, it is automatically switched to display it. Further, information of each field such as a graph may be displayed in parallel so as to match a time axis such as a date. Since a history of the information of each field is managed, the user can specify and browse the information of the past. In the calendar and the graph, the user is allowed to specify a period to be displayed thereon. The user can take a look of each information regarding a health state of the user through the screen described above, and can browse the individual information, whereby the user can recognize his or her health state intelligibly.

[Screen Including Calendar]

A screen example including a calendar is as follows. As items of information registered to and displayed on the calendar, there are various kinds of items as described above. As the information of each of the items, choices, numerical values, texts, marks and the like can be registered. As the choices, there are choices set by the present system, and choices set by the user. As selection of a date, a current date is selected automatically by default. Forms of the calendar and the information input are recited as follows.

In a calendar in a first form, as the example of the field 104 in FIG. 20, dates are arranged in a horizontal axis, and a plurality of information items is arranged in a vertical axis. When the user selects a date and an information item as input targets, information is inputted at an intersection between the date and the information item. As another form, information items may be arranged in a horizontal axis, and dates may be arranged in a vertical axis.

Figure 21:
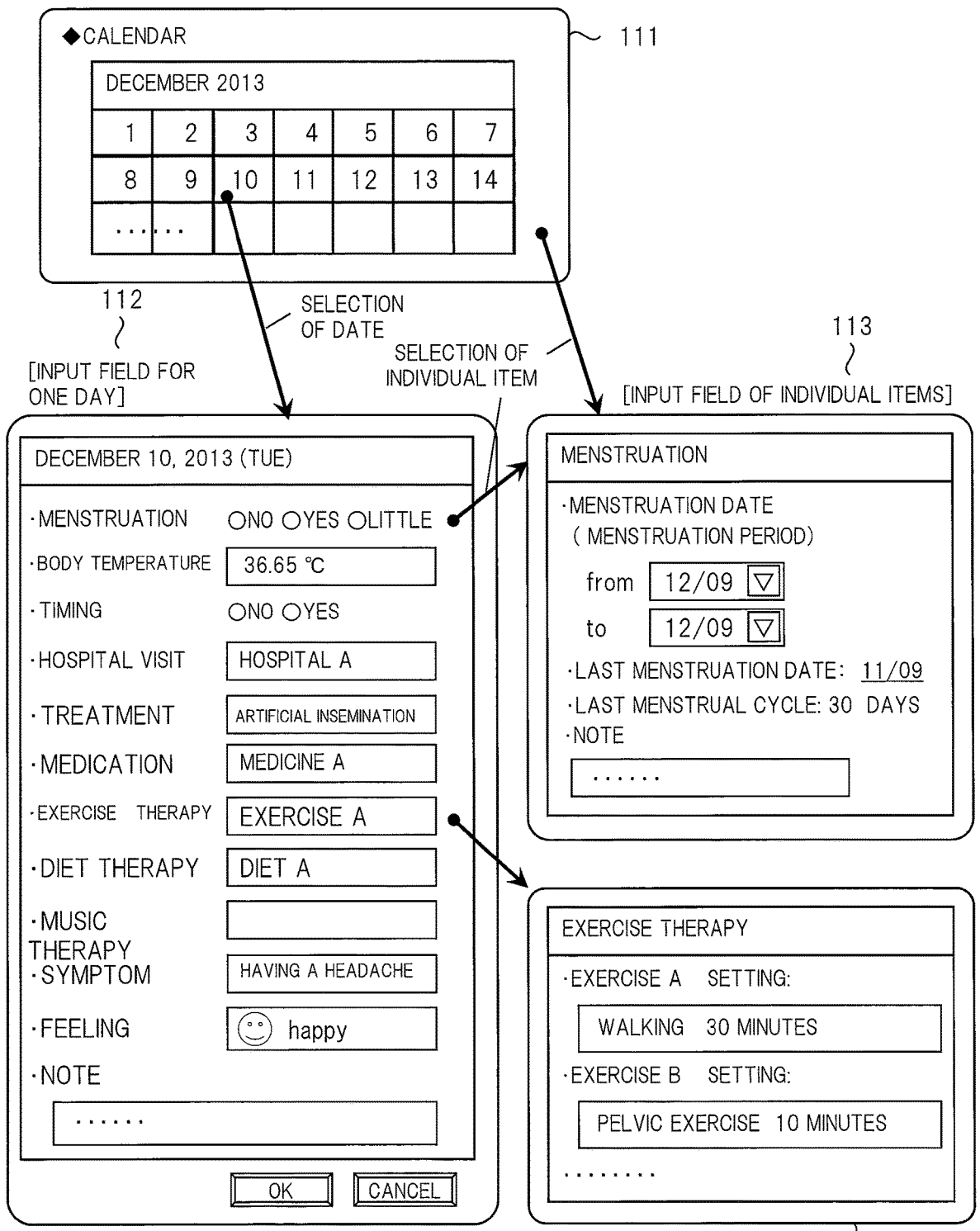
FIG. 21 is a view showing a screen example of a calendar and an input for unit of one day.

In the calendar of a second form, as an example of reference numeral 111 in FIG. 21, dates are arranged horizontally and vertically, and various kinds of information items are provided in the date on a daily basis. The user selects a date of an input target, whereby an input field or a screen of each date is displayed. As an example of reference numeral 112 in FIG. 21, the input field for one date has a plurality of information items, and the user inputs information into each item. The user can input information for an arbitrary date all at once.

A calendar of a third form is not a form to select a date like the first form or the second form. In the third form, a field for information for one day of the current date is automatically enlarged and displayed on the screen of the terminal 2 of the user. A plurality of information items is contained in the field for one date. The field for one date can be transitioned into a field for one month or the like.

FIG. 21 shows a screen example and an input example for one day in a case of a calendar in a second form. Reference numeral 111 is an example of the calendar in which each week is arranged vertically and horizontally. The user selects a desired date, for example, a date of today from the calendar. An input field for the selected date is displayed by a pop-up or the like. The reference numeral 112 is an example of an input field for one date. The input field for one date includes, as information items, menstruation, body temperature, timing (the timing method), hospital visit, treatment, medication, an action (exercise therapy, diet therapy and the like), a symptom, a feeling, a note and the like, for example. Information can be inputted in each of the items by choices, a text or the like. As each of the items in this field, a current date is registered by default.

A menstruation date and presence or absence of menstruation can be registered in the "menstruation" item. A body temperature numerical value can be registered in the "body temperature" item. For example, a value of the body temperature can be selected from choices in a list box. A medical institution or the like of a visiting hospital by the user can be registered in the "hospital visit" item. Treatment received in the visiting hospital can be registered in the "treatment" item. A name of medicine (or a trade name) prescribed and taken, an amount thereof and the like can be registered in the "medication" item. Exercise carried out by the user, and information on diet and food can be registered in the "action" item. Various kinds of symptoms, presence or absence of stress, and the like can be registered in the "symptom" item.

A text of an arbitrary note such as feelings, emotions, symptoms, actions, memos, and comments of the user can be registered in the "note" item. The user can input a text of a note in an input form, and register it by means of a registration button. Further, when to input the text, the user can specify a date (example: December 1) in a predetermined form like "#1201#". Further, the user may be allowed to register the basal body temperature (example: 36.65° C.) or the like in a predetermined form like "#3665#". Further, the user may be allowed to register voice data by providing a voice input button, or the user may be allowed to register image data by means of photographing of a camera by providing an image registering button.

The present system may separately provide a field or a screen for each individual item regarding the plurality of information items described above. The user can confirm and input detailed information in the field or on the screen for each individual item. Reference numeral 113 in FIG. 21 is an input field for the "menstruation" item as an example of the input field of an individual item. The calendar 111 or the input field 112 can be transitioned into the input field for the individual item like the reference numeral 113 in response to a selection operation of the user.

In the input field 113 for the "menstruation" item, a menstruation date and a menstruation period can be inputted by specifying a date range. Information such as a previous menstruation date, a previous menstruation period, a menstrual cycle this time, and an estimated ovulation day may be displayed in this field on the basis of the menstruation data and the analysis result thus registered. Further, a link of the displayed information may be transitioned into a screen of the corresponding graph. An input item of a text of a note regarding the menstruation may be provided in this field.

Reference numeral 114 indicates an example of an input field for the "exercise therapy" item. A name and a type of exercise, a date, an arbitrary text and the like can be inputted in this field.

This field can present a plurality of choices for exercise, and exercise of a choice selected among the choices by the user can be registered therein. The present system sets common action choices. Further, the user can set the exercise that the user often carries out in this field. For example, "walking for 30 minutes" or the like can be set by a text as setting of the exercise A. Thus, since the exercise A and the like are presented to the user as the choices when to register information on daily exercise, it is possible to register it easily. The user can also set information that the user input frequently in the input field for the other item.

As another example, a name, a type, details, a date, an arbitrary text and the like of treatment can be inputted in the input field of the "treatment" item. For example, in a case where the treatment is "artificial insemination", information such as positive or negative of LH, a size of follicle, an endometrium thickness can be inputted. In a case where the treatment is "in-vitro fertilization", information such as a method of in-vitro fertilization, an egg collection method, an egg collection date, an egg collection number, a size of follicle, a grade, and an endometrium thickness can be inputted. Further, in a case of sperm collection of a male user, information such as a date, an amount, density, and motility can be inputted. These pieces of information can be registered as the examination result described above.

[Screen Example of Input Field for One Date]

FIG. 22 shows an example of the input field for one date as a screen example of the terminal 2 of the user. The terminal 2 may be a smartphone or the like. A field for recording health data for one date is displayed on this screen. In this regard, the health information, the action information and the like are generically referred to as the health data in this screen. This screen includes, as information items, an ovulation test, a pregnancy test, a timing method, the amount of secretion, an examination result, and the like.

Positive or negative of a result of the ovulation test can be inputted in the "ovulation test" item. Positive or negative of a result of the pregnancy test can be inputted in the "pregnancy test" item. The ovulation test and the pregnancy test may be inputted by self measuring (self examination) of the user, or a predetermined examination result may be inputted by the medical institution or the examination institution. Input data such as the ovulation test and secretion is stored in the health information 53A. Presence or absence of sexual intercourse can be inputted in the "timing method" item. These input data are stored in the action information 53B. The amount of secretion can be selected and inputted in the "amount of secretion" item. The input information described above is used during the analysis processing such as the pregnancy support.

Information on results of various kinds of examinations can be inputted in detail in the "examination result" item. Although it is not illustrated, information on an examination type such as a blood examination, a date of the examination, an examination institution, an examination method, and the like can be inputted in the "examination result" item by means of choices or a text, for example. Values of various kinds of female hormones described above, and a value such as an endometrial thickness and a size of follicle can be inputted in the "examination result" item as the examination item.

FIG. 23 shows an input field of symptoms and stress as an example of the input field for one date. Information on various kinds of symptoms, stress and the like, which is concerned with the analysis such as tendency analysis of a symptom, disease risk warning, and pregnancy support can be inputted in this input field. In the symptom item, presence or absence, and the degree of each type of symptom can be selected and inputted in this input field. As examples of the symptom, there are a headache, a stomachache, a backache, depression, irritability, lethargy, and the like. Further, as items of stress, presence or absence of stress, the degree thereof and the like can be selected and inputted.

Input examples indicate "the user has a headache, but the degree thereof is light", "the user is in depression and the degree thereof is heavy", and "the user has high stress". The degree of the symptom or stress is a plurality of values, for example, light/medium/heavy, and the like. Further, a text representing a symptom, a mood and the like can freely be inputted in this input field. The input field described above is an example in which various kinds of symptoms can exhaustively be inputted for general check regarding a plurality of diseases, but it is not limited to this. A screen for check may be provided for each of specific diseases.

[Screen Example Containing Similar User Information]

FIG. 24 shows a screen example in which the similar user information is displayed in the terminal 2 of the user (example: the user X). A screen of FIG. 24 includes a "information on other user similar to you" field as a field in which the similar user information is displayed. The content of the similar user information described above is displayed in this field. This field may be displayed in the screen for MY medical record in FIG. 20 or in another screen.

The fields in FIG. 24 includes a field 241 for conditions, and a field 242 for a list of similar users. The field 241 for conditions displays information on conditions for determination of similar users. In the present example, in a case where the conditions are a similar attribute, the field 241 includes information on attributes and attribute values, for example, three of {age, disease, treatment}. In the present embodiment, sex is supposed to be a female, and the conditions are four attributes including the sex. A display example is "a person about (age) 35 years old, (disease) infertility, (treatment) in-vitro fertilization similar to you". Another display example is "a person of late thirties, who is diagnosed to be endometriosis, and considers in-vitro fertilization" and the like.

The conditions in the field 241 are determined and displayed in accordance with settings of the similar user determining information 61b. An attribute value of an attribute of the condition corresponds to a set value of an attribute item in the user attribute information 51 of the user X. A similar attribute of the condition uses one or more attribute value. The condition may be only an attribute of a disease, for example, and attributes such as medical institutions, anamnesis, pregnancy, partners can be added thereto.

Further, the conditions in the field 241 can similarly be set to actions of the health information, elements of information, and items of various kinds of analysis by the user setting information 61 described above. For example, as similar element or similar analysis, menstruation data, menstrual cycles, tendency of variation in the menstrual cycles, illness concerned with menstruation and the like can also be set. For example, in a case where the similar element is body temperature and menstruation, a display example thereof is "a person whose body temperature-menstruation graph is similar" and the like. Another display example is "a person whose action is similar", "a person having a possibility of the same disease", and the like. Further, as the conditions, "a person whose partner male is similar", "a person whose pair is similar", or the like can be selected.

As display of the similar user information on the screen in FIG. 24, all information or part of information of share items that are the content of the similar user information of an output target may be displayed directly. However, in a case where the amount of the similar user information is large, all of it cannot be displayed all at once. Thus, the list of the similar users in the field 242 is first displayed. In the list of the similar users in the field 242, information of one or more similar user is displayed in descending order of similarity in accordance with the content of the check information 57. As display of a field for information of one similar user, a part of the content of the similar user information of the output target may be displayed, or outline information may be displayed. The outline information contains a user name, share items and the like. The share items indicate items that are disclosed (or published) and can be browsed. As the outline information, the degree of similarity and a reference degree (will be described later) may be displayed.

In the list of the similar users in the field 242, detailed information of the similar users is displayed by a pop-up or on another screen and the like in response to a selection operation of the similar user or the share item desired by the user. Display of the detailed information is similar display to the screen of MY medical record in FIG. 20, for example, and each piece of information such as the similar user and the share item is displayed. In the outline information and the detailed information, in a case where there are settings of the priority output information 61C described above, only information on essential items is displayed, or information on preferential items is display in preferential order in accordance with the content of the settings. By the display of the list of the similar users described above or display based on priority output items, the user can easily browse the content of the similar user information, and can preferentially browse information that the user want to view.

Reference numeral 243 is a display example of information on one similar user, more particularly, an example in which items desired by the user X are displayed in a form so that information part of the user and information part of the similar user are compared with each other. The item of comparison may be an item that is selected arbitrarily by the user, or an item that is set in advance. When the outputting unit 18 outputs the similar user information to the user, the outputting unit 18 creates information for comparison, in which the same portions and different portions are organized so that they can be viewed easily between the users like the example of the reference numeral 243, on the basis of the check information 57, and causes the terminal 2 of the user to display it on the screen.

As an example of the reference numeral 243, treatment attributes that are items for comparison are displayed in a form so as to compare information indicating a situation of treatment containing a treatment history between the user X and the user C who is the similar user. As examples of the information indicating the situation of the treatment, age, a period of time, treatment name, the number of times of treatment, detailed content and the like are shown. Underlined portions are highlighted portions of different information between the user X and the user C, and the other portions are portions of the same information. As the display thereof, the same portions may be highlighted. The display of comparison information like the reference numeral 243 allows the user to intelligibly confirm and understand the same portions and the different portions between the user and the similar user, whereby it is easy to utilize the information. As another example, in a case where the user specifies an attribute of the medical institution, it is possible to browse comparison information on hospitals containing visiting of hospital and changing of hospitals. As a still another example, in a case where the user specifies an "action (exercise therapy)" as an element, it is possible to browse comparison information on exercise.

As another example, the outputting unit 18 may create information for comparison, in which similar items and dissimilar items are organized between the user and the similar user, on the basis of the check information 57, and similarly provide it. For example, information indicating that similar attributes are A and B and dissimilar attributes are C to H between the user X and the user C is provided in accordance with the content of the check information 57 in (a) of FIG. 15.

As still another example, display of only the same information part described above, display of only the different part, display of only the similar part, display of only the dissimilar part, and the like are possible. As still another example, data such as graphs of the respective users may be displayed so as to be arranged, or may be displayed so as to be superimposed.

As still another example, a display field for messages regarding the similar user information may be provided in the screen for MY medical record and the like in FIG. 20. Display examples are "Other users similar to you is the user A and the user B.", "An examination result graph of the user A is similar.", and the like. Thus, it is possible to browse detailed information of the similar user information from a link of the word in the messages.

As still another example, a button for evaluation of the similar user information may be provided. The user browses the similar user information described above. In a case where the user thinks that it is useful, the user presses the corresponding button. The server 1 reflects information of this button to evaluation of the similar user information. For example, the server 1 aggregates the information of the button described above for each of the similar user information, and calculates a reference degree that is an index value indicating usefulness and evaluation of the user by five-grade evaluation or the like. The reference degree is displayed in the list of the field 242 by means of asterisks or the like. The server 1 may reflect the reference degree to display order of a plurality of similar users in the list of the field 242. In that case, the user can preferentially browse information on other user whose evaluation is high.

Reference numeral 244 indicates an item by which display order regarding information on a plurality of similar user of the list in the field 242 can be rearranged on the basis of the degree of similarity, the reference degree, or other point of view by the user. Reference numeral 245 indicates a button for advanced search (will be described later). Reference numeral 246 indicates a button for displaying statistical information (will be described later).

Since the similar user information is automatically displayed on the screen described above, the user can easily browse and obtain the information of the similar users, and this makes it possible to reduce time and effort to search or seek such information by himself or herself. Further, in a case where the user cannot find useful information in the similar user information thus displayed, the user can change the condition by the user settings, and it is possible to search such useful information by utilizing the searching function 204 (will be described later).

[Screen Example of User Settings]

FIG. 25 shows a screen example of user settings regarding the user setting information 61 for each user. The user is allowed to set the content of the user setting information 61 regarding himself or herself via the present screen. The present screen includes a field 251 for setting a share item, a field 252 for setting a condition to determine a similar user, and a field 253 for setting a priority output item.

The field 251 corresponds to setting of the share setting information 61*a*. Although illustration thereof is omitted, in the field 251, whether to share the user attribute, the element of the health information and the action information, and the analysis result or not on the detailed item basis can be set by the user. The share of the user attribute is also possible even by the settings of the user attribute information 51 in FIG. 5A.

The field 252 corresponds to setting of the similar user determining information 61*b*. The field 252 includes a field 252*a* for selection of a target item, a field 252*b* for a user attribute, a field 252*c* for an element of the health information, a field 252*d* for an element of the action information, and a field 252*e* for an analysis result. In the field 252*a*, at least one of the user attribute, the element of the health information, the element of the action information, and the analysis result can be selected by means of a check button or the like as the item that is the condition for similar user determination. Detailed settings of the selected item are carried out in the field 252*b* or the like.

In the field 252*b*, one or more of various kinds of user attributes can be selected. In the field 252*b*, priority order of a plurality of attributes can be set. For example, first priority is age, second priority is a disease, and third priority is treatment. Moreover, a weighting value regarding the priority order may be set to each of the attributes. In the field 252*c*, one or more of various kinds of elements in the health information can be selected. Further, in a case where each classification such as the examination result contains a plurality of more detailed items, each of the more detailed items can be selected. Similarly, in the field 252*d*, one or more of various kinds of elements in the action information can be selected. In the field 252*e*, one or more of analysis results of various kinds of analysis types can be selected. In each of the field 252*c*, the field 252*d* and the field 252*e*, priority order of the like for a plurality of elements or analysis can be set in the similar manner to the user attribute. Further, although it is not illustrated, in the field 252, whether to apply a graph thereto or not scan be selected and set for each of the attributes and the elements. The field 252 allows the user to set the setting of a combination like the example in FIG. 7 or the like. As the condition for similar user determination, a logical condition such as AND, OR can be set by user settings.

The field 253 corresponds to settings of the priority output information 61C. In the field 253, one or more of the priority output items can be selected, and priority order of the items can be set. In the field 253, an item can be selected from choices in a list box, for example. In the field 253, either essential ones or preferential ones can be set.

As another form regarding the user settings, the user may set a pattern of the user setting information on the screen to save it, and the user may be allowed to select and use it. Further, the pattern of the user setting information by the present system may be presented as choices, and the user may be allowed to select and use it.

[Screen Example of Searching Function]

FIG. 26 shows a screen example regarding the searching function 204. The present screen is displayed in a case where usage of search is specified by the user. Information for searching information of other user in detail as the advanced search by the searching function 204 by means of specification of the condition by the user is displayed on the present screen. The present screen includes a field 261 for a search condition, and a field 262 for a search result. The present screen shows a case where search is carried out by using information of all users in the DB 50 as a target. However, a case where search is carried out by using a specific similar user as a target can also be realized similarly. For example, the advanced search button 245 on the screen in FIG. 24 allows the screen to be transitioned into the present screen, and the advanced search for the similar user information in FIG. 24 is possible.

The field 261 for the search condition includes a field 261*a* for selecting and inputting each attribute and its attribute value of the user attribute, a field 261*b* for selecting and inputting each element of the health information and the action information, and a value of its analysis result, and an input field 261*c* for free keywords.

In the field 261*a*, an attribute value of each attribute corresponding to the user attribute information 51 can be inputted by using choices of a list box, a text of the like. In the field 261*b*, a value or a state before analysis or after analysis can be selected and inputted for each element of the health information and the action information. For example, in the item of the body temperature, a value of a state such as a basal body temperature, a difference in temperature $\Delta T$, and tendency of a difference in temperature $\Delta T$ can be specified. For example, "a difference in temperature $\Delta T$ 0.3° C.", "improvement of the difference in temperature $\Delta T$" or the like can be selected. In the item of the exercise, specific exercise can be specified. In the item of the symptom, a specific symptom can be specified. In the input field 261c, a keyword that is a search condition can freely be inputted with a text.

In the field 262 for the search result, search result information by the search condition in the field 261 is displayed. As display of the search result information in the field 262, a list of the other users may be displayed in similarity order or the like in the similar manner to the field 242 in FIG. 24, for example. The display is transitioned into display of detailed information of the other users in response to a selection operation of other users desired by the user. The searching function 204 allows the user to search, browse and obtain information of the other user by using a variety of and detail conditions, and this makes it possible to search useful information.

[Screen Example of Statistical Information]

FIG. 27 shows a screen example including display of the statistical information by the statistical function 205. The present screen includes a field 271 for displaying statistical information regarding a similar user, and a field 272 for displaying statistical information regarding all users. A button 246 for the statistical information displayed on the screen in FIG. 24 allows to transition to the present screen, for example. Only one of the field 271 and the field 272 may be displayed.

The content of statistical data containing aggregate results regarding a predetermined item in share information of a similar user to one user is displayed in the field 271. Information of a predetermined item of interest is displayed in reference numeral 271a. The item of interest may be fixed settings by the present system, or may be selected by the user. The present embodiment shows the case of exercise of the actions in the elements of the action information. With respect to the item in the reference numeral 271a, information on various kinds of exercise that is registered for a plurality of users who is similar users is displayed as a list in descending order of the number of corresponding users in reference numeral 271b, for example. For example, this example shows that the number of users who carry out the exercise is larger in order of exercise A, B, C. Further, user names of the corresponding users can be displayed in each row for the exercise, and the user can browse detailed information thereof from a link. The user can understand and consult the exercise that the other users whose attribute such as age and disease is similar to that of the user carry out.

In the field 272, the content of statistical data containing aggregate results regarding a predetermined item in the share information of all users is displayed. In reference numeral 272a, information on a predetermined item to be paid attention to is displayed, and the present embodiment shows a case of a medical institution of the user attributes. With respect to the item in the reference numeral 272a, information on various kinds of medical institutions of attribute values of attributes of medical institutions of all users is displayed as a list in descending order of the number of corresponding users in reference numeral 272b, for example. For example, this example shows that the number of users who visit a hospital is larger in order of hospital A, B. Information on hospital names is displayed in each row for the medical institution in the reference numeral 272b, and information on treatment and examinations that the medical institution provides is displayed on the basis of the medical examination information 52. The present page can be transitioned into a page of detailed information from a link of a word such as the medical institution and the treatment in the reference numeral 272b. The user can understand which medical institution the other user utilizes, and what kind of treatment or examination the medical institution provides and the like.

Further, the user names of the corresponding users may be displayed in each row for the medical institution in the reference numeral 272b, or the content of the text of the note by the corresponding user may be picked up and displayed. For example, frequent words may be extracted in the text of the note and displayed. The user can know impression and comments of evaluation of the other user regarding the medical institution, and can consult it for selection of a hospital to be visited.

Reference numeral 272d is an example of the item to which other users pay attention, and shows a case of age when to receive treatment A and a situation of pregnancy as the user attributes. Statistical information regarding the item in the reference numeral 272d is displayed in reference numeral 272e. A graph of age when to receive the treatment A and the number of persons is displayed in a left side thereof, thereby displaying a statistical value such as average age. A graph of a success rate of pregnancy on the basis of results by receiving the treatment A is displayed in a right side thereof. The user can know and consult the age and the number of the other users who received the treatment A, and the success rate of pregnancy on the basis of the results by receiving the treatment A.

In the list of the statistical information such as the reference numerals 271b and 272b, display order of the information in the plurality of rows can be selected and rearranged by the user in a point of view of the number of corresponding users. Further, a button for evaluation may be provided for each row of the list for the statistical information. In a case where the user consulted information in the row or evaluates exercise, a hospital or the like in the row, the user presses the button. The server 1 aggregates information of the button, and calculates an evaluation point, which is an index value, for each piece of information of each row. The server 1 may cause the terminal 2 to display the evaluation point of information in each row of the list, or may reflect it to the display order. The server 1 may calculate the evaluation point of the information in each row on the basis of a check of the content of the text of the note. In this case, the user can preferentially browse information with high evaluation.

As another display example, the server 1 may graphically associate the items of the attributes in the statistical information described above as an aggregation target with a group of extracted words of the check result for the text of the note in each unit of the list such as the attribute value, and may cause the terminal 2 to display them. For example, each of the words may be used as nodes, and a graph in which a size of each node is changed in accordance with the number of appearance thereof may be displayed.

As described above, the user can intelligibly browse various kinds of statistical information on the screen of the terminal 2 in addition to the similar user information, the user can consult them for his or her activities such as treatment. Another display example by the statistical function 205 is statistical information such as a time or a period of start and end of treatment, impressions and feelings of the treatment, experiences of various kinds of examinations, a situation of a disease and treatment concerned with clinical diagnosis and treatment departments other than obstetrics and gynecology departments, medicine for medication, a situation of the partner, and an amount of money for treatment in the group of users who has the same disease or the same symptom. It is easy for the user to select specific treatment, an examination and the like, and determine start and end of the treatment or examination.

[Other Screen Example]

Figure 28:
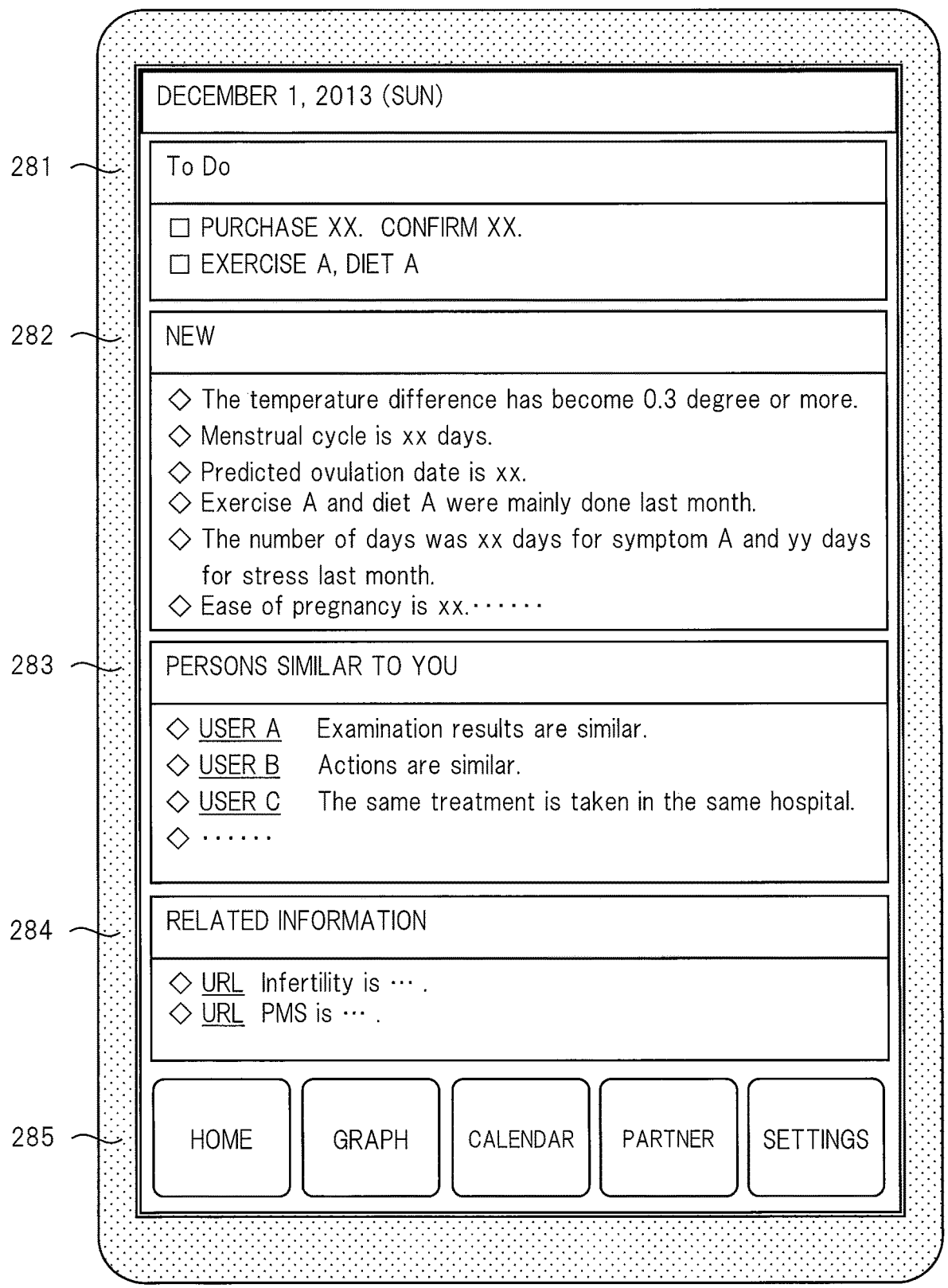
FIG. 28 is a view showing another screen example.

FIG. 28 shows a display example of information for one day (today) in the terminal 2 of a female user as another screen example. The present screen includes a "To Do" field 281, a "NEW" field 282, a "person similar to you" field 283, a "related information" field 284, and a menu 285.

"To Do" for one day (today), that is, list information to be done today is displayed in the "To Do" field 281. For example, the user can select a date on the screen of the calendar, and can register the "To Do" information by a text or choices. The information hereby registered is displayed in the "To Do" field 281. As examples of the "To Do" information, there are purchase of test drug, visiting of a hospital, an examination, and a schedule of an action such as exercise and diet.

The latest output message information according to a health state of the user is displayed in the "NEW" field 282. The output message information contains the various kinds of analysis results described above.

The similar user information is automatically displayed in the "person similar to you" field 283. For example, the similar users are picked up in similarity order, and information indicating which point of view the user is similar to the similar user on the basis of is displayed. The display is transitioned into display of detailed information in response to selection of the similar user by the user.

The content of the related search information provided by the related information searching function is automatically displayed in the "related information" field 284. The related information searching function automatically searches, from the Internet, related information concerned with a health state and output messages of each user, and the similar user information, and the related search information is displayed in the "related information" field 284. A processing example of the related information searching function is as follows.

The analyzing function 202 of the server 1 determines and detects tendency of the health state and a possibility of a disease of the user. The related information searching function automatically searches, from an external communication network such as the Internet and an external server, related information at timing of the detection on the basis of a keyword described in processing logics of the analysis described above, a keyword included in a message of the analysis result, or a keyword contained in the similar user information.

The related information searching function stores index information or published information itself such as a URL, which is search result information, in the DB 50 as the related search information. The outputting unit 18 displays the content of the related search information in the "related information" field 284 or the like on the screen of the terminal 2 of the user. In a case where the content of the related search information is a URL, it is possible to transition the page into a detailed Webpage. In another method of displaying the related search information, the page may be displayed by a link from a word in the output message or the similar user information.

As the related search information described above, published information and the like of a Web site closely related to the keyword are obtained. For example, in a case where there is 'PMS' or 'infertility' as the keyword included in the analysis result of the health state of the user, medical information related to the keyword is obtained. The user can easily browse, obtain and consult the related information concerned with the health state and the like of the user.

The menu 285 indicates button for an operation to select a function, and there are "HOME", "graph", "calendar", "partner", "settings" and the like, for example. The "HOME" button allows to transition to a screen for HOME of the service or the like. The "graph" button allows to transition to a screen of a graph such as the body temperature-menstruation graph. The "calendar" button allows to transition to a screen of the calendar. The "partner" button allows to transition to a screen on which information on a partner such as a husband is displayed. The "settings" button allows the screen to be transitioned into a screen for user settings. A screen of information on partners includes an input field for the user attributes, the health information and the action information of the partner, for example, whereby examination result data such as a semen examination can be inputted, for example. In this regard, in a case where a female user mainly utilizes this system, or in a case where a male user mainly utilizes this system, it is possible to realize various kinds of functions of the present service similarly.

[Analysis Example—Tendency Analysis]

An example of the analysis processing by the analyzing function 202 will be described briefly. An example of processing of tendency analysis is as follows. In a case of the tendency analysis of the body temperature and the menstruation, the analyzing unit 16 calculates a value of a predetermined item such as the menstrual cycle a2 and the difference in temperature ΔT from the registered data of the user. the analyzing unit 16 determines and detects, for each item, good or bad of the absolute value and tendency of relative improvement or deterioration or maintenance on the basis of comparison with the numerical value of predetermined reference information. The analyzing unit 16 calculates, for each item, a variation amount in time series for a target period, and records it in the analysis information 56. The variation amount is a differential value between the menstrual cycle a2 previous time and the menstrual cycle a2 this time, for example. The analyzing unit 16 compares the variation amount of the item with a predetermined numerical value, and determines a state of tendency thereof.

The analyzing unit 16 determines and detects periodic stability and pattern in the variation of time series values of data of the user described above on the basis of comparison with a number range of the reference information or a reference graph. For example, the analyzing unit 16 refers to the variation in values such as the menstrual cycle a2 of the user for the past target period. In a case where the variation is small, the analyzing unit 16 determines that the periodic stability is high and the state is good. In a case where the variation is large, the analyzing unit 16 determines that the periodic stability is low and the state is bad.

In a case of the tendency analysis of the examination result, the analyzing unit 16 refers to the reference information of time series values of plural types of female hormones, which are examination items of examination result data, in each individual female hormone, and determines and detects a state of the tendency. The analyzing unit 16 refers to the reference information on a combination of a plurality of female hormones, and comprehensively determines the state of the tendency. The analyzing unit 16 comprehensively determines the state by including a relationship among the female hormones described above, the values of the body temperature and the menstruation, and the values of the menstrual cycle a2 and the like.

The present system provides the user with the information such as the value of the state of the tendency, the variation amount, the periodic stability, the pattern, and the index value of the closeness of the reference by the result of the tendency analysis described above.

[Analysis Example—Disease Risk Warning]

A processing example of the disease risk warning is as follows. The analyzing unit 16 estimates and checks a possibility of each of the various kinds of diseases peculiar to females in conjunction with the results of the tendency analysis and the like of the combination of the elements of the user described above. Processing logics and reference information according to the disease and the like of the check target are set to the processing defining information 59. In this regard, the present analysis is merely unique and gradual estimation, is not medical diagnosis by the medical institution, but the output is helpful information. The user is notified of this intention. Hereinafter, as an example of the specific disease, it is that the disease A=PMS (premenstrual syndrome).

Specific symptoms and values of the action that are estimated to be medically associated with the disease A, reference information regarding values such as body temperature, menstruation, and female hormones in a case of the disease A, and a target period and the like are set to the processing defining information 59 regarding check of the disease A, for example.

The analyzing unit 16 refers to the values of the "disease" and the "anamnesis" in the user attribute information 51 of the user, and confirms the correspondence in current or past states of the disease A and the like and the correspondence of a state of the other diseases related to the disease A. The analyzing unit 16 refers to symptom data of the user in the target period, and determines and detects good or bad of the symptom, and tendency of improvement or deterioration on the basis of the tendency analysis of the symptom. The analyzing unit 16 extracts the specific symptom and stress that are considered to be related to the disease A from the symptom data of the user on the basis of the processing defining information 59 regarding the disease A. For example, a symptom a with a mild headache, a symptom b with a deep depression, high stress, and the like are extracted.

The analyzing unit 16 refers to data on the body temperature, the menstruation and the female hormone, which are considered to be related to the disease A, in the target period, and grasps tendency thereof from the result of the tendency analysis. For example, the analyzing unit 16 refers to information such as feelings among a menstruation date, a menstrual cycle, a difference in temperature, female hormones, exercise, diet, and notes.

The analyzing unit 16 uses the processing defining information 59 and the reference information described above to estimate a possibility that the user falls under the disease A on the basis of the health state containing the tendency of the symptom of the user. The analyzing unit 16 determines a possibility of the disease A in a form of presence or absence, three or more levels, percentage (%) or the like. For example, in a case where all of a plurality of specific symptoms is extracted, the analyzing unit 16 determines that there is a possibility of the disease A or the possibility is high and the like. For example, in a case where the number of specific symptoms thus extracted is a reference number or more, the analyzing unit 16 may determine that there is a possibility of the disease A and the like. In a case where the degree of the specific symptom exceeds a reference degree, the analyzing unit 16 may determine that there is a possibility of the disease A and the like.

In another example, in a case where a value of a predetermined item such as the menstrual cycle a2 or its variation amount exceeds a predetermined reference value, the analyzing unit 16 determines that there is a possibility of the specific disease. For example, in a case where a value of a combination of plural types of female hormones satisfies a predetermined reference condition, the analyzing unit 16 determines that there is a possibility of the specific disease.

In a case where a text of a note is used to analyze disease risk warning or a symptom, the analyzing unit 16 extracts words representing symptoms, feelings and the like contained in the text by means of text mining. For example, there are a positive word such as "feel good", a negative word "mood is bad", and the like. The analyzing unit 16 determines the health state on the basis of the number of extracted words.

[Analysis Example—Action Extraction]

An analysis example and a check example related to the action extraction are as follows. The analyzing unit 16 extracts actions including diet and exercise as actions that are useful to improve the health state of each user on the basis of the processing defining information 59 as the action extraction processing. The analyzing unit 16 generates the action support information containing the extracted actions. For example, with respect to the PMS, unrefined grains, vitamins A and C, marine plants, vitamins B6, nuts, vegetable oils, and processed soy products are recited as examples of diet that is generally useful for improvement. Further, as examples of the exercise, bathing, sleeping, moderate exercise before one to two weeks of menstruation are recited. The analyzing unit 16 analyzes a correlation between a symptom of the PMS of the user from an ovulation day to a starting date of menstruation and the actions like the examples described above. Namely, the analyzing unit 16 extracts diet and exercise that may influence on a result that the symptom of the PMS of the user is improved or deteriorated, and accumulate data in time series.

The checking unit 17 checks similarity of a predetermined combination between the users, and make the connection between similar users. For example, the checking unit 17 makes the connection between the first user and the second user or the like who is a similar user so that a predetermined attribute is similar. Here, the first user is in a situation that the symptom of the PMS is not improved, and the second user is in a situation that the symptom of the PMS is improved. The first user is interested in the disease and symptom of the PMS and actions that influence thereon, whereby the disease and symptom of the PMS and the actions are specified as the priority output items.

The checking unit 17 picks up the second user for whom the symptom of the PMS is improved and the action that is estimated to be useful for improvement of the symptom of the PMS of the second user among similar users of the first user on the basis of a result of the action extraction processing. The checking unit 17 picks up an action that is different from the action of the first user among actions of the second user, and adds information on the action to the action support information to be provided to the first user as part thereof. The checking unit 17 adds the action support information containing the second user and the action to the similar user information as part thereof, and reflects it to the check information 57 and the output information 58.

The outputting unit 18 outputs the share information of the second user and the action support information to the screen of the terminal 2 of the first user on the basis of the output information 58 described above and the priority output item of the first user. The outputting unit 18 compares similar part and dissimilar part regarding the actions between the first user and the second user in the similar manner to the example of the reference numeral 243 in FIG. 24, and displays it on the screen. The similar part is a predetermined attribute and the like. The outputting unit 18 preferentially displays, as the dissimilar information part, the action that is estimated to be useful for improvement of the symptom of the PMS of the second user, in particular, the action that the first user has not carried out but the second user has carries out. This makes it possible for the first user to try the action for improving the symptom of the PMS by reference to the action of the second user.

[Analysis Example—Pregnancy Support]

The pregnancy support function supports spontaneous pregnancy and childbirth of a female, and supports pregnancy activities with a relationship of partners between the female user and a male user. The pregnancy activities include treatment, actions and the like. The pregnancy support function cares a health state of each user of the partners of the male and the female, and provides the pregnancy support information, which contains advice regarding the pregnancy activities and the message information such as recommendation, in conformity with the health state. This causes the health states of the partners of the male and the female to become good, and causes fertility and activity to become a high state, whereby they stimulate the pregnancy activity of the male and female and this makes it possible to comprehensively heighten a possibility and a success rage of pregnancy.

The pregnancy support function grasps and analyzes a state of the female user concerned with fertility containing body temperature, menstruation, female hormones, uterus, ovarian and the like. The pregnancy support function grasps and analyzes a state of the male user concerned with fertility containing hormones, testis and the like. The pregnancy support function analyzes a cause of infertility or the like with respect to both of partners of the male and the female. The pregnancy support function improves the health state of the male and female, generates the pregnancy support information containing an analysis result of the cause of infertility and advice about the analysis result so as to become a state that it is easy to achieve spontaneous pregnancy, and provide the reference information to the user.

A processing example of the pregnancy support function by the analyzing unit 16 is as follows. The analyzing unit 16 determines the health state concerned with fertility, pregnancy and infertility of the user on the basis of the predetermined processing defining information 59 by using the user attribute information 51 of the user, various kinds of health information and action information, and the analysis results such as the tendency analysis. The analyzing unit 16 generates the pregnancy support information in accordance with the health state, transmits it to the terminal 2 of the user, and causes the terminal 2 to display it on the screen. The pregnancy support information contains the advice of actions and the like for activating the pregnancy activities of the partners of the male and the female, and information such as recommendation.

The pregnancy support function carries out processing to presume an ovulation day that is largely concerned with realization of pregnancy, for example. The analyzing unit 16 presumes the ovulation day by using various kinds of user input data, and accumulates information on a result of presumption of the ovulation day in the DB 50. The pregnancy support function provides the pregnancy support information containing the information on the presumed ovulation day to the user. Various kinds of methods for processing to presume the ovulation day are available.

The analyzing unit 16 may calculate a state of a single user such as ease of spontaneous pregnancy as a unique index value. Further, the analyzing unit 16 may calculate, as an index value unique to the present system, the state of the pair of the female user and the male user who are partners, such as ease of pregnancy of the pair unit on the basis of the analysis results of the health states of both users. The pregnancy support function may provide the user with the pregnancy support information containing the index value such as ease of pregnancy described above.

[Effects and the Like]

As explained above, according to the health care system of the present embodiment, it is possible to realize support of obtainment regarding a health state and medical information of a user, which contain body temperature and examination results of the user, enhancement and advancement of the provided information, such as advice, regarding the health state and the medical information of the user, reduction of time and effort to input data by the user, securement of motivation and a willingness, and the like. This makes it possible to comprehensively care for the health state of the user and support of treatment and examinations.

The present system shares information such as the user attributes, the health information, the action information, and the analysis result with the group of users, and automatically provide share information for the similar users to each of the users. The present system automatically checks the similar users by using the share information concerned with the health states of the group of users, and provide the similar user information. The user can easily browse and obtain various kinds of information containing a health state of other user whose situation and the like are similar to those of the user. Each of the users can know what kind of treatment, examinations and actions the other user similar to the user carries out in what kind of attribute and health state. Further, the user can know feelings, thoughts, experiences, handling and the like of each of the other users.

In the conventional service, the user consciously has to search other users whose situation is similar to that of the user, whereby it takes large time and effort to obtain useful information that the other user has, and it is difficult to obtain useful information. The present system can significantly reduce the time and effort to obtain and share medical information and the like between the users compared with the conventional service. The user can search the other users as a comparison target by himself or herself via the Internet and the like, whereby it is possible to reduce time and effort to obtain useful information, and the user can easily find the useful information with a small time and effort.

The user can obtain awareness regarding his or her own health state by viewing the similar user information. Since the useful information can be obtained automatically in the form of the similar user information, the user can easily obtain awareness about points that the user is not aware of by alone by comparing the user with the other users. Further, the user can recognize similar information parts, different information parts and the like between the user and the other user by viewing the similar user information, whereby it is easy for the user to understand them.

The user can view the similar user information, and consult useful information therein. It is easy for the user to determine what kind of treatment, examinations, medical institutions, and actions the user is to select in order to maintain and improve the health state of the user, and it is easy for the user to utilize such information for seeking actual diagnosis, pregnancy activity and the like. The user can recognize a possibility of his or her own disease or infertility to deal with it early. For example, the user can know a case example that the other user who has the same medical condition as the user carries out treatment, examinations, actions and the like that are different from those carried out by the user, and can consult such a case example.

The present system provides the user with the similar user information, the advanced search information, the statistical information, the related search information and the like, and supports activities of the user including treatment and examinations. The user refers to a variety of provided information, whereby the user can easily understand and determine the medical information such as an examination result. Further, the user can obtain information such as plural kinds of treatment and examinations, and a plurality of actions from the variety of provided information, and can make a comparative review of the information as candidates for selection. The user can obtain not only information of specific persons, but also information of a variety of persons, whereby it is possible to avoid only biased information from being obtained.

The user can obtain information of the similar user and/or other user in accordance with selection of service and user settings by using various desired conditions. The user shares information of a desired item with other users (in particular, the similar users), whereby it is possible to obtain the information of the item as the similar user information. Further, the user can obtain, as the similar user information, information of other user who is similar to the user in a desired point of view, such as the attributes, the health information, the action information and the analysis results. Further, the user can effectively browse the similar user information of the desired item essentially or preferentially.

The present system provides, by the analyzing function 202, information such as analysis results and messages of each user to each user. Each user can intelligibly recognize his or her own health state from the information such as his or her own analysis results and messages. The present system automatically provides, by the checking function 203, the similar user information to each user. Therefore, the user can easily obtain awareness regarding the health state and the like by comparing the user and the other users.

The present system inclusively and individually manages information on a plurality of the medical institutions and examinations by using the medical examination information 52, provides support suitable for treatment and examinations of each user, and utilizes it to check a similar user of the group of users. The present system organizes the share information of the group of users in a comparable manner by using the medical examination information 52 and the like, automatically carries out the check processing for a similar user in the background, and determines the user and the data of a comparison target. This makes it possible for each user to reduce difficulty to determine a similar user and information thereof by himself or herself.

The user can browse various kinds of attributes such as his or her age, diseases, treatment, pregnancy and a partner while comparing them with those of the similar user. Therefore, the user can obtain awareness regarding his or her own situation. For example, the user can obtain information on a person who experienced treatment or an examination, a person who succeeded pregnancy, a person who stopped treatment, a person who gave up pregnancy, and the like.

The user can easily determine continuation or termination of treatment and the like in view of his or her age, a time, an amount of money and the like. The user can also obtain information such as details of treatment of each of other users. Therefore, it is possible to determine the continuation or termination easily.

The user can browse his or her own body temperature, menstruation, female hormones, actions, symptoms, notes, and a state of their tendency while comparing them with those of the similar user. Therefore, the user can obtain awareness regarding his or her own health state. The user can compare time series data and information between the user and the other user in addition to comparison of graphs. The user can easily search an action suitable for the user himself or herself by means of comparison with the other users, whereby the user easily has a willingness to work on actions, treatment and the like. The user can easily determine treatment, a medical institution or the like by referring to comments of notes of the other users.

The user can browse a possibility of disease of the user, a health state concerned with pregnancy and infertility, and a state concerned with pregnancy activities on the basis of the analysis result while comparing them with those of other user. Therefore, the user can obtain awareness regarding diseases and pregnancy, whereby the user easily has a willingness to work on treatment and pregnancy activities.

The present service includes functions to manage and analyze time series data of the user like the tendency analysis and the action extraction. Therefore, the content of the similar user information contains information regarding variation in a state of other user in time series. The user can also observe variation in a state of other user in time series by means of the similar user information. For example, the user can also know transition and conclusion of treatment, actions and the like, which can be used as reference for determination.

The present system includes the input auxiliary function, and includes a mechanism to reduce a load of data input and facilitate the data input. Therefore, it requires small time and effort to input the respective data, and the user can easily have a willingness to continuously register data. As there is much and accurate share information by user input, the similar user information to be provided is enriched, thereby increasing the amount of information that can be referred to. Therefore, the user can easily have a willingness to continuously input data every day.

The present system can continuously support the user in the middle of activities such as treatment, examination, and pregnancy of the user in clinical diagnosis and treatment departments including the obstetrics and gynecology department and before and after the activities. A plurality of users participates in the service according to the present system, and shares information with the other users. Therefore, each user can know the existence of the other users who are similar to the user, and have a feeling to work on the activities such as treatment and pregnancy together with the other users. The user can partially share feelings including anxiety and pleasure with the other users.

The present system can widely support users, medical care, and the like by means of a mechanism including share, accumulation, and check of information regarding the medical care and the like among the users. The present system can be applied without a premise of existence of population data, that is, data of specimens of a large number of people.

The present invention is not limited to the embodiment described above, and may be modified in various ways without departing from the substance of the present invention. Another embodiment can be recited as follows. The present system counts the amount of data inputted by the user via the application 20 of the terminal 2 of the user, the number of days to input data, especially the amount of share information and the like, and manages them as index values. The server 1 stores the index values described above, and causes the terminal 2 to display them on the screen of the application 20. The present system may give privilege or the like on the service to the user in accordance with the index values described above. This further motivates the user to input data.

The examination result data described above may contain information on determination results of the health state by the medical institution or the examination institution, for example, information on good or bad of the female hormones and a possibility of a disease. The server 1 may register, for each user, the information of the determination results in the examination result data described above, and utilize them for check of a similar user by the checking unit 17. Namely, the server 1 may register analysis result information for predetermined analysis from the outside, and utilize the analysis result information for check of similarity between the users.

In the present system, the provided information such as various kinds of registered data by the group of users and the similar user information is accumulated in the DB 50 as a history, and each user can utilize the accumulated information. The present system may provide the share information and the statistical information thus accumulated not only to the user but also to the medical institutions and the like. For example, by providing data on the group of users regarding diseases and symptoms, it is possible to contribute development of the medical care.

The present invention is applicable to a field of medical care and health care including obstetrics and gynecology department and reproductive medicine.

(Appendix)

The explanation of the embodiment described above has been described so that the following inventions can be at least realized by a person having an ordinary skill in the art to which the present invention belongs.

(1) A health care system, comprising:
a server apparatus configured to provide service for caring for a health state of each of users; and
terminals of the users,
wherein the server apparatus includes:
a data managing unit configured to register and manage user information containing at least one of attribute information, health information, or action information as share information of a group of users in response to an operation from the terminal of the user, the attribute information containing at least one of sex, age, diseases, treatment, medical institutions, examination institutions, or anamneses of the user, the health information containing time series data of at least one element containing measurement items that include a body temperature of the user, menstruation, examination results, medication, or symptoms, the action information containing at least one of time series data of actions or arbitrary texts;
a checking unit configured to check similarity between the users in the share information, determine a similar user of each of the users, and store a determination result as check information; and
an outputting unit configured to output share information of the similar user of the user to the terminal of the user on the basis of the check information.

(2) The health care system according to claim (1),
wherein the server apparatus further includes an analyzing unit,
wherein the analyzing unit is configured to analyze the user information of the user, determine a health state of each user on the basis of a result obtained by comparing time series values of data on the element with a number range of reference information, and store an analysis result including the health state as analysis information,
wherein the outputting unit is configured to output message information according to the health state of each of the users to the terminal of the user on the basis of the analysis information, and
wherein the data managing unit is configured to register and manage the analysis result or the message information as share information of the group of users.

(3) The health care system according to claim (1),
wherein the checking unit is configured to compare attribute values in the attribute information between the users, calculate a degree of similarity between the users by means of a check of similarity of the attribute values, and make connection between each of the users and the similar user in accordance with the degree of similarity.

(4) The health care system according to claim (3),
wherein the checking unit is configured to calculate an index value of similarity between the users among the respective attribute values of one or more specific attributes of the attribute information, and calculate the degree of similarity between the users regarding the attribute information by means of total calculation of the index value.

(5) The health care system according to claim (3),
wherein the data managing unit is configured to manage an attribute value in a situation of pregnancy or childbirth as the attribute information of the user, and
wherein the checking unit is configured to compare the attribute values in the situation of the pregnancy or the childbirth, and calculate the degree of similarity between the users.

(6) The health care system according to claim (3),
wherein the data managing unit is configured to manage an attribute value in a situation of a partner as the attribute information of the user, and
wherein the checking unit is configured to compare the attribute values in the situation of the partner, and calculate the degree of similarity between the users.

(7) The health care system according to claim (1),
wherein the checking unit is configured to compare data on the elements in the health information between the users, calculate a degree of similarity between the users by means of a check of similarity of the data on the elements, and make connection between each of the users and the similar user in accordance with the degree of similarity.

(8) The health care system according to claim (7),
wherein the checking unit is configured to calculate an index value of similarity between data on the elements in data on one or more specific elements in the health information between the users, and calculate the degree of similarity between the users regarding the health information by means of total calculation of the index value.

(9) The health care system according to claim (7),
wherein the data managing unit is configured to manage data on the symptoms, and
wherein the checking unit is configured to compare the data on the symptoms between the users, calculate a degree of similarity between the users by means of a check of similarity of the symptoms, and make connection between each of the users and the similar user in accordance with the degree of similarity.

(10) The health care system according to claim (7),
wherein the data managing unit is configured to manage data on the medication, and
wherein the checking unit is configured to compare the data on the medication between the users, calculate a degree of similarity between the users by means of a check of similarity of the medication, and make connection between each of the users and the similar user in accordance with the degree of similarity.

(11) The health care system according to claim (1),
wherein the checking unit is configured to compare data on the elements in the action information between the users, calculate a degree of similarity between the users by means of a check of similarity of the data on the elements, and make connection between each of the users and the similar user in accordance with the degree of similarity.

(12) The health care system according to claim (11),
wherein the checking unit is configured to calculate an index value of similarity between data on the elements in data on one or more specific elements in the action information between the users, and calculate the degree of similarity between the users regarding the action information by means of total calculation of the index value.

(13) The health care system according to claim (11),
wherein the data managing unit is configured to manage data on an arbitrary text of the user, the arbitrary text being inputted with respect to date of a calendar, and
wherein the checking unit is configured to compare the data on the texts between the users, calculate the degree of similarity between the users by means of a check of similarity of the data on words of the texts, and make connection between each of the users and the similar user in accordance with the degree of similarity.

(14) The health care system according to claim (1),
wherein the data managing unit is configured to create and manage a graph of specific data in the user information, and
wherein the checking unit is configured to compare the graphs between the users, calculate a degree of similarity between the users by means of a check of similarity of the graphs, and make connection between each of the users and the similar user in accordance with the degree of similarity.

(15) The health care system according to claim (14),
wherein the data managing unit is configured to create and manage the graph of data in the examination results, and
wherein the checking unit is configured to compare the graphs between the users, calculate a degree of similarity between the users by means of a check of similarity of the graphs of the examination results, and make connection between each of the users and the similar user in accordance with the degree of similarity.

(16) The health care system according to claim (14),
wherein the data managing unit is configured to create and manage a graph of data on the body temperature and the menstruation, and
wherein the checking unit is configured to compare the graphs of the body temperature and the menstruation between the users, calculate a degree of similarity between the users by means of a check of similarity of the graphs, and make connection between each of the users and the similar user in accordance with the degree of similarity.

(17) The health care system according to claim (1),
wherein the data managing unit is configured to manage the user information of a partner of the user, and
wherein the checking unit is configured to compare the user information between partners of the users, calculate a degree of similarity between the partners by means of a check of similarity of the user information, and make connection between each of the users and the similar user in accordance with the degree of similarity.

(18) The health care system according to claim (2),
wherein the checking unit is configured to check the similarity between the users in the analysis result or the message information, determine the similar user of each of the users, and store the determination result as the check information.

(19) The health care system according to claim (18),
wherein the checking unit is configured to check similarity between partners in the analysis result or the message information of the partner of each of the users, determine the similar user of each of the users, and store the determination result as the check information.

(20) The health care system according to claim (1),
wherein the checking unit is configured to:
compare attribute values of at least one attribute in the attribute information between the users, and calculate a degree of first similarity regarding the attribute information between the users by means of a check of the similarity of the attribute values;
compare data of at least one element in the health information between the users, and calculate a degree of second similarity regarding the health information between the users by means of a check of the similarity of the data of the element;
compare data of at least one element in the action information between the users, and calculate a degree of third similarity regarding the action information between the users by means of a check of the similarity of the data of the element;
calculate the degree of similarity of a combination by using two or more degrees of similarity among the degrees of first to third similarity; and
make connection between each of the users and the similar user in accordance with the degree of similarity of the combination.

(21) The health care system according to claim (1),
wherein the data managing unit is configured to create and manage a graph of data on the user information,
wherein the checking unit is configured to:
compare attribute values of at least one attribute in the attribute information between the users, and calculate a degree of first similarity regarding the attribute information between the users by means of a check of the similarity of the attribute values;

compare data of at least one element in the health information between the users, and calculate a degree of second similarity regarding the health information between the users by means of a check of the similarity of the data of the element;

compare data of at least one element in the action information between the users, and calculate a degree of third similarity regarding the action information between the users by means of a check of the similarity of the data of the element;

compare the graphs between the users, and calculate a degree of similarity regarding the graphs between the users by means of a check of similarity of the graphs;

calculate the degree of similarity of a combination by using one or more degree of similarity among the degrees of first to third similarity and the degree of similarity regarding the graphs; and make connection between each of the users and the similar user in accordance with the degree of similarity of the combination.

(22)

The health care system according to claim (2), wherein the checking unit is configured to:

compare attribute values of at least one attribute in the attribute information between the users, and calculate a degree of first similarity regarding the attribute information between the users by means of a check of the similarity of the attribute values;

compare data of at least one element in the health information between the users, and calculate a degree of second similarity regarding the health information between the users by means of a check of the similarity of the data of the element;

compare data of at least one element in the action information between the users, and calculate a degree of third similarity regarding the action information between the users by means of a check of the similarity of the data of the element;

compare data in the analysis result or the message information between the users, and calculate a degree of similarity regarding the analysis result or the message information between the users by means of a check of similarity of the data;

calculate the degree of similarity of a combination by using one or more degree of similarity among the degrees of first to third similarity and the degree of similarity regarding the analysis result or the message information; and make connection between each of the users and the similar user in accordance with the degree of similarity of the combination.

(23)

The health care system according to claim (20), wherein the data managing unit is configured to manage user information of a partner of the user, and wherein the checking unit is configured to:

compare attribute values of at least one attribute in the attribute information between the users, and calculate a degree of first similarity regarding the attribute information between the users by means of a check of the similarity of the attribute values;

compare data of at least one element in the health information between the users, and calculate a degree of second similarity regarding the health information between the users by means of a check of the similarity of the data of the element;

compare data of at least one element in the action information between the users, and calculate a degree of third similarity regarding the action information between the users by means of a check of the similarity of the data of the element;

compare the user information between the partners of the users, and calculate a degree of similarity between the partners by means of a check of similarity of the user information;

calculate the degree of similarity of the combination by using one or more degree of similarity among the degrees of first to third similarity and the degree of similarity between the partners; and make connection between each of the users and the similar user in accordance with the degree of similarity of the combination.

(24)

The health care system according to claim (1), wherein the data managing unit is configured to manage user information of a second user who is a partner of a first user as the user, wherein the checking unit is configured to:

compare the user information between the first users, and calculate a degree of first similarity between the first users by means of a check of similarity of the user information;

compare the user information between the second users, and calculate a degree of second similarity between the second users by means of a check of similarity of the user information;

calculate a degree of similarity of a pair of the first user and the second user by using the degree of first similarity and the degree of second similarity; and make connection between each of the users and the similar user in accordance with the degree of similarity of the pair.

(25)

The health care system according to claim (20), wherein the checking unit is configured to:

compare attribute values of attributes including at least one of the age, the treatment, or the anamnesis in the attribute information between the users, and calculate the degree of first similarity;

compare data of at least one element of the examination results, the symptoms, or the medication in the health information between the users, and calculate the degree of second similarity; and calculate the degree of similarity of the combination by using the degree of first similarity and the degree of second similarity.

(26)

The health care system according to claim (2), wherein the server apparatus further includes a setting unit configured to set, for each of the users, whether at least one item of an attribute value of each attribute in the attribute information, data of each element in the health information, data of each element in the action information, or the analysis result or the message information by specific analysis is contained in the share information of the group of users or not.

(27)

The health care system according to claim (2), wherein the server apparatus further includes a setting unit configured to set, for each of the users, whether at least one item of a specific attribute value in the attribute information, data of a specific element in the health information, data of a specific element in the action information, or the analysis result or the message information by specific analysis is included in subjects for comparison or not as a condition when the checking unit determines a similar user of each of the users.

(28)

The health care system according to claim (2), wherein the server apparatus further includes a setting unit configured to set, for each of the users, at least one item of a specific attribute value in the attribute information, data of a specific element in the health information, data of a specific element in the action information, or the analysis result or the message information by specific analysis as an item to be essentially or preferentially outputted when the outputting unit outputs the share information of the similar user of the user.

(29)

The health care system according to claim (1), wherein the outputting unit is configured to display a list of a plurality of similar users in order according to the similarity when the outputting unit outputs the share information of the similar user of the user to the terminal of the user, and display detailed information of the share information of the similar user in response to designation of the similar user from the list.

(30)

The health care system according to claim (1), wherein the outputting unit is configured to display information obtained by comparing information part the same as or similar to between the user and the similar user with information part different from or dissimilar to between the user and the similar user when the outputting unit outputs the share information of the similar user of the user to the terminal of the user.

(31)

The health care system according to claim (2), wherein the server apparatus further includes a searching unit, and wherein the searching unit is configured to search the share information of the group of users on the basis of a search condition, and provide search result information to the terminal of the user, the search condition containing at least one of an attribute value in the attribute information, a value of data of an element in the health information, a value of data of an element in the action information, a value of the analysis result or the message information, or an arbitrary keyword, which is designated from the terminal of the user.

(32)

The health care system according to claim (2), wherein the server apparatus further includes a statistical unit, and wherein the statistical unit is configured to create statistical information, and output the statistical information to the terminal of the user, the statistical information containing aggregate results and statistical values of at least one item of an attribute value in the attribute information, data of an element in the health information, data of an element in the action information, or the analysis result or the message information.

(33)

The health care system according to claim (2), wherein the server apparatus further includes a related information searching unit, and wherein the related information searching unit is configured to automatically search related information via an external communication network including the Internet by using, as a search condition, a specific word contained in at least one item of an attribute value in the attribute information, data of an element in the health information, data of an element in the action information, or the analysis result or the message information in the user information of the user, and provide related information to the terminal of the user, the related information being a search result.

(34)

The health care system according to claim (2), wherein the data managing unit is configured to manage data on the examination results, the data containing hormones including a female hormone as an examination item, wherein the analyzing unit is configured to determine the health state of each of the users on the basis of comparison between a past value and a current value in the time series values of the data on the examination results of the user and on the basis of a result obtained by comparing the time series values of the data on the examination results with the number range of the reference information corresponding to the examination item, the health state containing a tendency of variation in a value of the examination item, and wherein the checking unit is configured to compare the tendencies between the users, and determine the similar user of each of the users.

(35)

The health care system according to claim (2), wherein the data managing unit is configured to manage data on the body temperature and the menstruation, wherein the analyzing unit is configured to determine the health state of each of the users on the basis of comparison between a past value and a current value in the time series values of the data on the body temperature and the menstruation of the user and on the basis of a result obtained by comparing the time series values of the data on the body temperature and the menstruation with the number range of the reference information corresponding to the body temperature and the menstruation, the health state containing a tendency of variation in the body temperature and the menstruation, and wherein the checking unit is configured to compare the tendencies between the users, and determine the similar user of each of the users.

(36)

The health care system according to claim (2), wherein the data managing unit is configured to manage data in the action information, the data being inputted to a date of a calendar and containing exercise or diet of the user, wherein the analyzing unit is configured to extract a past action from the time series data in the action information of the user, the past action being estimated to be related to the health state of the user, and wherein the checking unit is configured to compare the actions between the users, and determine the similar user of each of the users.

(37)

The health care system according to claim (2), wherein the analyzing unit is configured to determine, as the health state of each of the users, a possibility of a disease from a plurality of diseases on the basis of a result obtained by comparing a value in the user information of the user with the number range of the reference information, the user information containing the health information, and wherein the checking unit is configured to compare the possibilities of the disease between the users, and determine the similar user of each of the users.

(38)

The health care system according to claim (36), wherein the analyzing unit is configured to extract an action estimated to be useful for improvement of the health state of each of the users from a group of actions set in advance or the time series data in the action information of the user, and generate action support information containing the extracted action, and wherein the outputting unit is configured to output the action support information to the terminal of the user. (39)

The health care system according to claim (38), wherein the checking unit is configured to extract, for the user and the similar user, an action that the user has never carried out from actions estimated to be useful for improvement of the health state of the similar user, and store the extracted action in the check information, and wherein the outputting unit is configured to display the action that the user has never carried out among the actions estimated to be useful for improvement of the health state of the similar user as information part different from or dissimilar to between the user and the similar user when the outputting unit outputs the share information of the similar user of the user to the terminal of the user.

The invention claimed is:

1. A health care system, comprising:
terminals of users; and
a server apparatus configured to
provide service for caring for a health state of each of the users,
register and manage, at any time, user information of each user containing attribute information, health information, action information and share information of a group of the users in response to operations from the terminals of the users, the attribute information containing partner information representing, for each of the users having a partner, attributes of the partner including a situation of the partner relative to the user, and at least one of sex, age, diseases, treatment, medical institutions, examination institutions, and anamneses of each user, the health information containing time series data of at least one element containing measurement items that include a body temperature of the user, menstruation, examination results, medication, and symptoms, the action information containing at least one of time series data of actions and arbitrary texts, and the share information indicating which of the attribute information, the health information and the action information is shared with other users,
manage the user information of partners of the users,
compare, in response to an inquiry received at any time from an inquiring user input via an inquiring terminal, attribute values in the attribute information shared with other users, the attribute values being compared including partner attribute values in the partner information and the user information between the partners of the users,
calculate a degree of the similarity between the users based on at least a partner similarity of the user information of the partners,
make a connection between each of the users and the at least one similar user thereof in accordance with the degree of similarity,
determine, based on the degree of similarity between the users, at least one similar user among the users, and
display, at the inquiring terminal, at least some of the user information of the at least one similar user shared with other users with similar and different portions of the user information of the inquiring user and the at least one similar user organized for comparison by the inquiring user.

2. A health care system, comprising:
terminals of users; and
a server apparatus configured to
provide service for caring for a health state of each of the users,
register and manage, at any time, user information of each user containing attribute information, health information, action information and share information of a group of the users in response to operations from the terminals of the users, the attribute information containing partner information representing, for each of the users having a partner, attributes of the partner including a situation of the partner relative to the user, and at least one of sex, age, diseases, treatment, medical institutions, examination institutions, and anamneses of each user, the health information containing time series data of at least one element containing measurement items that include a body temperature of the user, menstruation, examination results, medication, and symptoms, the action information containing at least one of time series data of actions and arbitrary texts, and the share information indicating which of the attribute information, the health information and the action information is shared with other users,
manage user information of partners of the users,
compare, in response to an inquiry received at any time from an inquiring user input via an inquiring terminal, attribute values of at least one attribute in the attribute information shared between the users, the attribute values being compared including partner attribute values in the partner information,
calculate a first degree of first similarity regarding the attribute information between the users based on the first similarity of the attribute values;
compare health data of at least one health element in the health information between the users,
calculate a second degree of second similarity regarding the health information between the users based on the second similarity of the health data of the at least one health element;
compare action data of at least one action element in the action information between the users,
calculate a third degree of third similarity regarding the action information between the users based on the third similarity of the action data of the at least one action element;
calculate a partner degree of partner similarity between the partners based on the partner similarity of the user information of the partners of the users,
calculate a combined degree of combined similarity of a combination by using at least two degrees among the first degree of the first similarity, the second degree of the second similarity, the third degree of the third similarity and the partner degree of the partner similarity between the partners,
make a connection between the users in accordance with the combined degree of combined similarity of the combination,
determine, based on the combined degree of combined similarity of the combination, at least one similar user among the users, and
display, at the inquiring terminal, at least some of the user information of the at least one similar user shared with other users with similar and different portions of the user information of the inquiring user and the at least one similar user organized for comparison by the inquiring user.

3. A health care system, comprising:

terminals of users; and a server apparatus configured to provide service for caring for a health state of each of the users, register and manage, at any time, user information of each user containing attribute information, health information, action information and share information of a group of the users in response to operations from the terminals of the users, the attribute information containing partner information representing, for each of the users having a partner, attributes of the partner including a situation of the partner relative to the user, and at least one of sex, age, diseases, treatment, medical institutions, examination institutions, and anamneses of each user, the health information containing time series data of at least one element containing measurement items that include a body temperature of the user, menstruation, examination results, medication, and symptoms, the action information containing at least one of time series data of actions and arbitrary texts, and the share information indicating which of the attribute information, the health information and the action information is shared with other users, manage the user information of first and second users who are in partner relationships, respectively, compare, in response to an inquiry received at any time from an inquiring user input via an inquiring terminal, attribute values in the attribute information shared with other users, the attribute values being compared including partner attribute values in the partner information and the user information between the first users, calculate a first degree of first similarity between the first users based on the first similarity of the user information of the first users, compare the user information between the second users, calculate a second degree of second similarity between the second users based on the second similarity of the user information or the second users, calculate a combined degree of combined similarity of pairs of the first users and the second users, based on the first degree of the first similarity and the second degree of the second similarity;

make a connection between the users in accordance with the combined degree of similarity, determine, based on the combined degree of combined similarity between the pairs of the first users and the second users, at least one similar user among the first and second users, and display, at the inquiring terminal, at least some of the user information of the at least one similar user shared with other users with similar and different portions of the user information of the inquiring user and the at least one similar user organized for comparison by the inquiring user.

* * * * *